(12) United States Patent
Wakefield et al.

(10) Patent No.: US 8,933,047 B2
(45) Date of Patent: Jan. 13, 2015

(54) POLY(ACRYLATE) POLYMERS FOR IN VIVO NUCLEIC ACID DELIVERY

(75) Inventors: Darren H. Wakefield, Fitchburg, WI (US); David B. Rozema, Middleton, WI (US); Nicholas Rossi, Madison, WI (US); Lauren Almeida, Madison, WI (US); Anthony L. Perillo-Nicholas, Madison, WI (US)

(73) Assignee: Arrowhead Madison Inc., Madison, WI (US)

( * ) Notice: Subject to any disclaimer, the term of this patent is extended or adjusted under 35 U.S.C. 154(b) by 168 days.

(21) Appl. No.: 13/592,403

(22) Filed: Aug. 23, 2012

(65) Prior Publication Data

US 2013/0317079 A1 Nov. 28, 2013

Related U.S. Application Data

(60) Provisional application No. 61/625,955, filed on Apr. 18, 2012.

(51) Int. Cl.
| | | |
|---|---|---|
| *C12N 15/11* | (2006.01) | |
| *C08F 20/10* | (2006.01) | |
| *C08F 120/10* | (2006.01) | |
| *C08F 220/10* | (2006.01) | |
| *A61K 47/32* | (2006.01) | |
| *C08F 220/00* | (2006.01) | |
| *C08F 220/36* | (2006.01) | |

(52) U.S. Cl.
CPC .............. *A61K 47/32* (2013.01); *C08F 220/00* (2013.01); *C08F 220/36* (2013.01)
USPC ..................................... 514/44 A; 525/330.3

(58) Field of Classification Search
CPC ..... A61K 9/0017; A61K 9/146; A61K 47/32; A61K 47/48176; C08F 220/00
See application file for complete search history.

(56) References Cited

U.S. PATENT DOCUMENTS

| | | |
|---|---|---|
| 2009/0048410 A1 | 2/2009 | Wakefield |
| 2011/0009571 A1 | 1/2011 | Taft |
| 2011/0143434 A1 | 6/2011 | Stayton |
| 2011/0207799 A1 | 8/2011 | Rozema |
| 2011/0224377 A1 | 9/2011 | Mahanthappa |
| 2011/0286957 A1 | 11/2011 | Prieve |
| 2013/0121954 A1 * | 5/2013 | Wakefield et al. ......... 424/78.17 |

FOREIGN PATENT DOCUMENTS

| | | |
|---|---|---|
| WO | WO2011112911 A2 | 9/2011 |
| WO | WO2011115641 A1 | 9/2011 |
| WO | WO2011163121 A1 | 12/2011 |

OTHER PUBLICATIONS

Ahmed M, Bhuchar N, Ishihara K, Narain R. "Well-controlled cationic water-soluble phospholipid polymer-DNA nanocomplexes for gene delivery." Bioconjugate Chem. 2011, vol. 22, p. 1228-1238.

Boyer C, Bulmus V, Davis TP, Ladmiral V, Liu J, Perrier S "Bioapplications of RAFT Polymerization" Chem. Rev. 2009 vol. 109, No. 11, p. 5402-5436.

Chiefari J et al. "Living Free-Radical Polymerization by Reversible Addition-Fragmentation Chain Transfer: The RAFT Process" Macromolecules (1998), vol. 31, No. 16, p. 5559-5562.

Chu DS et al. "Application of Living Free Radical Polymerization for Nucleic Acid Delivery" Accounts of Chemical Research 2012 vol. 45, No. 7, p. 1089-1099.

Convertine AJ et al. "Development of a novel endosomolytic diblock copolymer for siRNA delivery" Journal of Controlled Release (2009) vol. 133, p. 221-229.

De Smedt SC, Demeester J, Hennink WE. "Cationic polymer based gene delivery systems" Pharm. Res. 2000, vol. 17, p. 113-126.

Duvall CL et al. "Intracellular Delivery of a Proapoptotic Peptide via Conjugation to a RAFT Synthesized Endosomolytic Polymer" Molecular Pharmaceutics (2009).

Kuroda K et al. "The Role of Hydrophobicity in the Antimicrobial and Hemolytic Activities of Polymethacrylate Derivatives" Chem. Eur. J. (2009) vol. 15, p. 1123-1133.

Lee SB, Russell AJ, Matyjaszewski, K. ATRP synthesis of amphiphilic random, gradient, and block copolymers of 2-(dimethylamino)ethyl methacrylate and n-butyl methacrylate in aqueous media, Biomacromolecules (2003) vol. 4, No. 5, p. 1386-1393.

Lipscomb CE, Mahanthappa, MK. "Poly(vinyl ester) Block Copolymers Synthesized by Reversible Addition-Fragmentation Chain Transfer Polymerizations" Macromolecules (2009), vol. 42. No. 13, p. 4571-4579.

Liu Y et al. "Bionanoparticles of amphiphilic copolymers polyacrylate bearing cholesterol and ascorbate for drug delivery" Journal of Colloid and Interface Science (2012), vol. 377, No. 1, p. 197-206.

Lowe AB, McCormick CL. "Homogeneous Controlled Free Radical Polymerization in Aqueous Media" Australian Journal of Chemistry (2002), vol. 55, p. 367-379.

Moad G et al "Living Radical Polymerization by the RAFT Process—A Second Update." Aust. J. Chem. 2009, vol. 62, p. 1402-1472.

Moad G, Rizzardo E, Thang SH. "Toward Living Radical Polymerization." Acc. Chem. Res. 2008, vol. 41, p. 1133-1142.

Sumerlin BS et al. "Block copolymerization of vinyl ester monomers via RAFT/MADIX under microwave irradiation" Polymer (2011), vol. 52, No. 14, p. 3038-3045.

Wolfert MA, Dash PR, Nazarova O, Oupicky D, Seymour LW, Smart S, Strohalm J, Ulbrich K. "Polyelectrolyte vectors for gene delivery: influence of cationic polymer on biophysical properties of complexes formed with DNA" Bioconjugate Chem. 1999, vol. 10, p. 993-1004.

Xu FJ, Yang WT. "Polymer vectors via controlled/living radical polymerization for gene delivery" Progress in Polymer Science 2011, vol. 36, p. 1099-1131.

* cited by examiner

*Primary Examiner* — Robert M Kelly
(74) *Attorney, Agent, or Firm* — Kirk Ekena

(57) ABSTRACT

The present invention is directed membrane active poly(acrylate) polymers and compositions for targeted delivery of RNA interference (RNAi) polynucleotides cells in vivo. RNAi polynucleotides are conjugated to the poly(acrylate) polymers and the polymers are reversibly modified to enable in vivo targeted delivery. Membrane activity of the poly(acrylate) provides for movement of the RNAi polynucleotides from outside the cell to inside the cell. Reversible modification provides physiological responsiveness.

20 Claims, 21 Drawing Sheets amphipathic poly(acrylate) random copolymer

Amine Deprotection of Polymers

A.
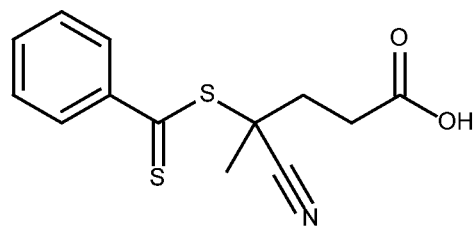
B.
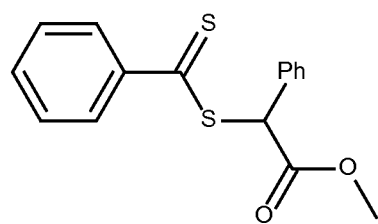
C.
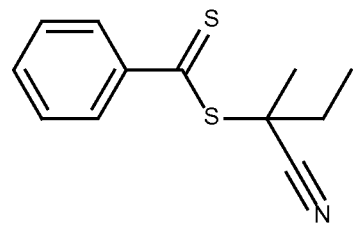
D.
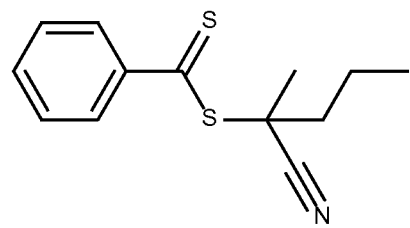
exemplary RAFT Reagents
FIG. 4 amine protected LAU 41648-140-B-fr1 m = 72%, n = 28% amine protected LAU 42101-23-D-fr1 amine protected NAR 42020-117A-fr1 amine protected NAR 41439-141B-fr1 amine protected NAR 41439-71B-fr1

A.
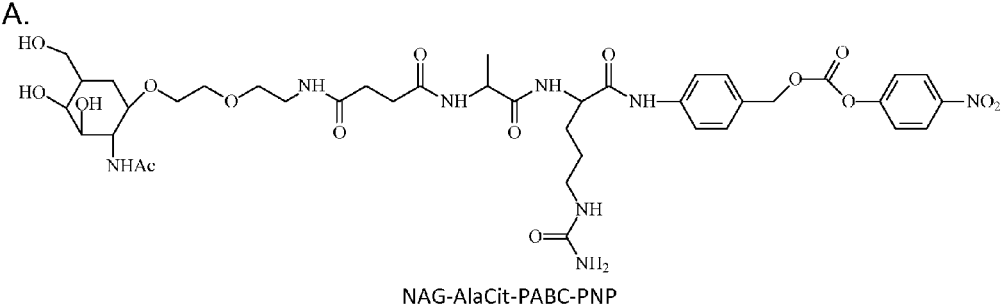
NAG-AlaCit-PABC-PNP
B.
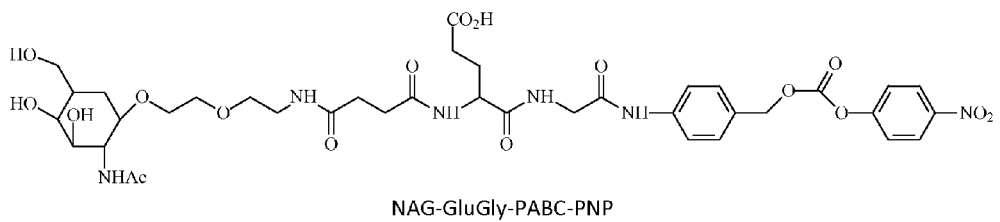
NAG-GluGly-PABC-PNP
C.
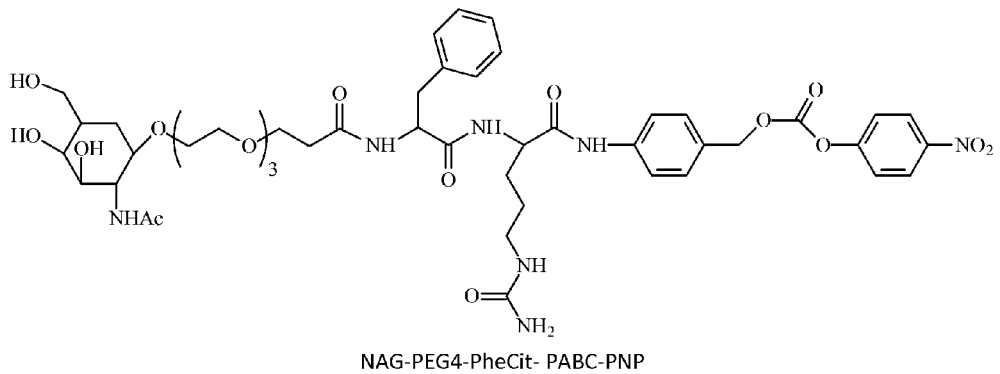
NAG-PEG4-PheCit- PABC-PNP
FIG. 10

D.
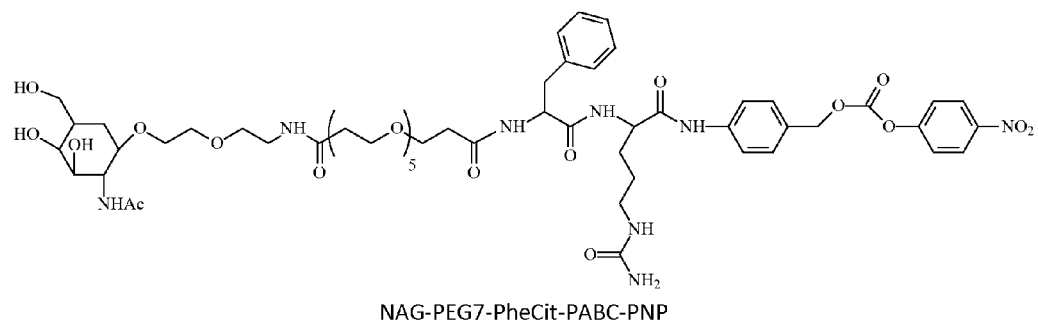
NAG-PEG7-PheCit-PABC-PNP
E.
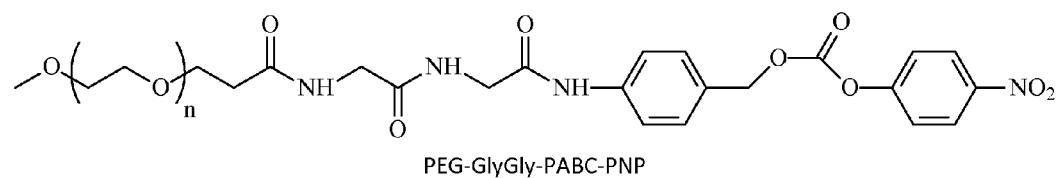
PEG-GlyGly-PABC-PNP
F.
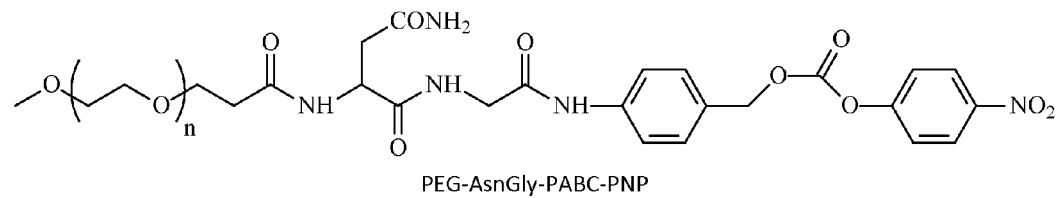
PEG-AsnGly-PABC-PNP
G.
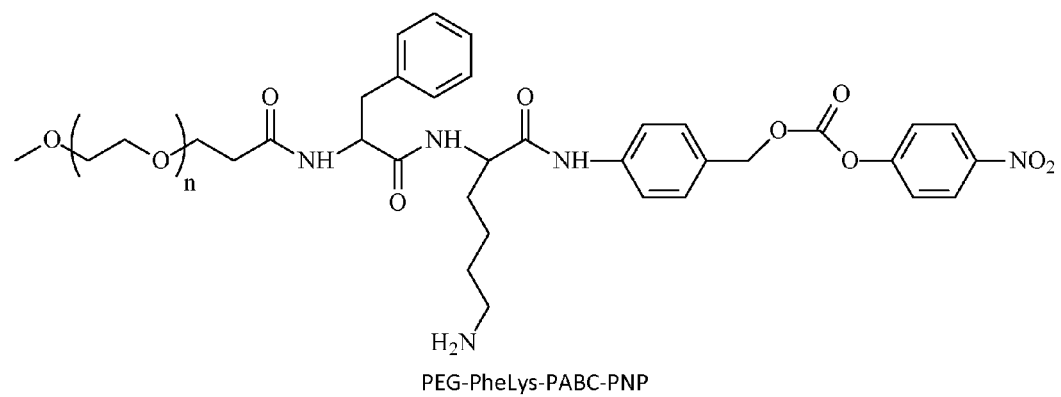
PEG-PheLys-PABC-PNP
FIG. 10 (cont.)

H.
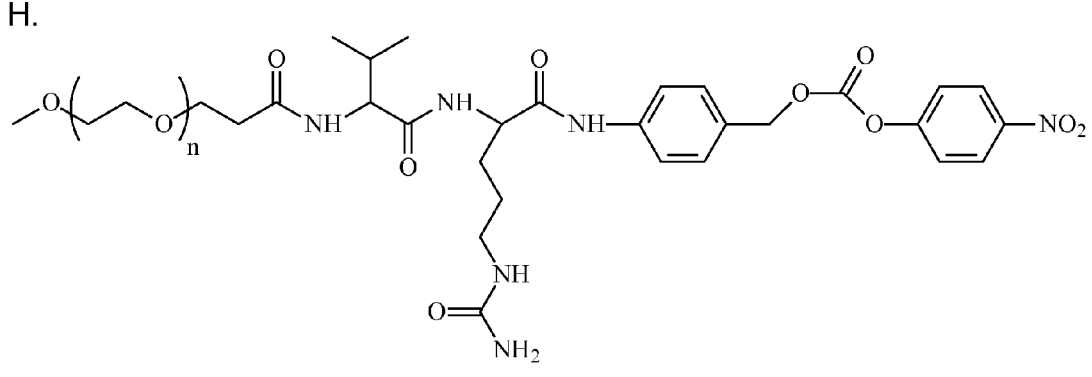
PEG-ValCit-PABC-PNP
I.
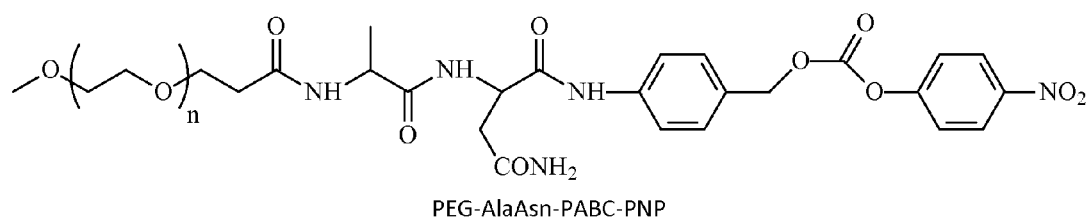
PEG-AlaAsn-PABC-PNP
J.
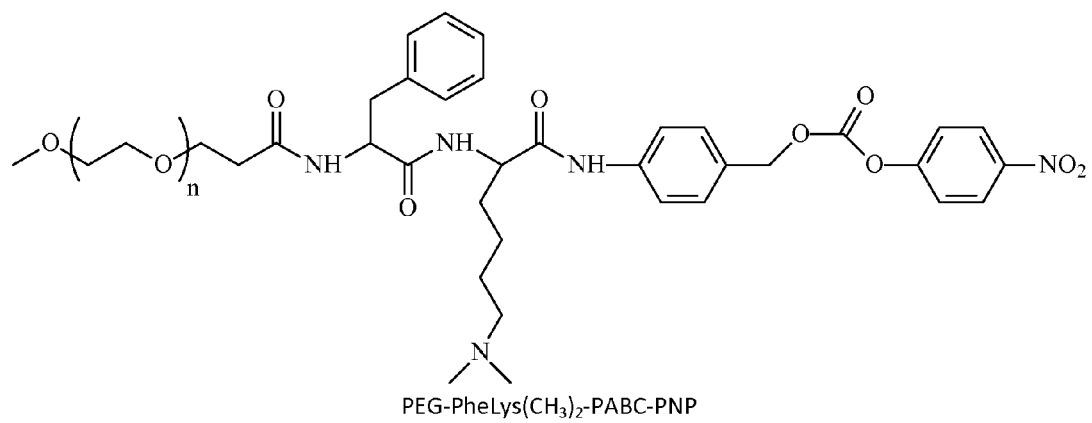
PEG-PheLys(CH₃)₂-PABC-PNP
FIG. 10 (cont.)

K.

PEG₁₂-Phe-Cit-PABC-PNP

Dipeptide masking agents

Percent Aha1 knockdown *in vitro* following delivery of 500 ng/mL Aha1 siRNA with 3.0 or 1.5 μg/ml ethylaminoacrylate + butyl methacrylate (EAA-BuMA) copolymers.

| polymer | | cell type | | | | | | | | |
|---|---|---|---|---|---|---|---|---|---|---|
| | | Hep3B-SEAP | | MCF7 | | HT29 | | HepG2-SEAP | | A375 | |
| % Amine | MW | 3.0 μg/ml | 1.5 μg/ml | 3.0 μg/ml | 1.5 μg/ml | 3.0 μg/ml | 1.5 μg/ml | 3.0 μg/ml | 1.5 μg/ml | 3.0 μg/ml | 1.5 μg/ml |
| 45% | 54.4 | 87% | 85% | 87% | 51% | 87% | 51% | 81% | 65% | 89% | 68% |
| 46% | 41.7 | 81% | 85% | 83% | 54% | 80% | 59% | 73% | 72% | 92% | 81% |
| 47% | 29.9 | 79% | 85% | 60% | 46% | 50% | 24% | 69% | 65% | 48% | 40% |
| 58% | 34.4 | 87% | 90% | 81% | 83% | 69% | 72% | 66% | 52% | 93% | 91% |
| 70% | 27.3 | 82% | 83% | 51% | 51% | 25% | 20% | 56% | 36% | 87% | 77% |
| 72% | 46.5 | 78% | 81% | 41% | 41% | 8% | 19% | 53% | 31% | 82% | 63% |
| 84% | 25.6 | 47% | 32% | | | | | | | | |
| 86% | 47.5 | 32% | 23% | | | | | | | | |

FIG. 11

Percent Aha1 knockdown *in vitro* following delivery of 500 ng/mL Aha1 siRNA with 3.0 or 1.5 μg/ml ethoxyethylaminoacrylate + sec-butyl acrylate (EEAA-SecBuA) copolymers.

| polymer | | cell type | | | | | | | | |
|---|---|---|---|---|---|---|---|---|---|---|
| | | Hep3B-SEAP | | MCF7 | | HT29 | | HepG2-SEAP | | A375 | |
| % Amine | MW | 3.0 μg/ml | 1.5 μg/ml | 3.0 μg/ml | 1.5 μg/ml | 3.0 μg/ml | 1.5 μg/ml | 3.0 μg/ml | 1.5 μg/ml | 3.0 μg/ml | 1.5 μg/ml |
| 53% | 24.5 | 57% | 65% | 26% | 23% | | | 32% | 28% | 41% | 31% |
| 53% | 40.5 | 57% | 75% | 21% | 19% | | | 41% | 10% | 64% | 52% |
| 53% | 59.4 | 75% | 85% | 43% | 38% | | | 52% | 31% | 68% | 74% |
| 59% | 24.8 | 55% | 53% | 24% | 19% | | | 31% | 26% | 39% | 32% |
| 58% | 56.3 | 74% | 78% | 51% | 29% | | | 50% | 21% | 66% | 70% |
| 64% | 24.0 | 43% | 41% | 24% | 15% | | | 25% | 17% | 29% | 19% |
| 64% | 47.2 | 54% | 57% | 42% | 26% | | | 30% | 20% | 68% | 65% |
| 68% | 24.5 | 29% | 30% | 17% | 11% | | | | | 17% | 12% |
| 69% | 58.8 | 49% | 49% | 39% | 21% | | | | | 57% | 57% |

FIG. 12

Percent Aha1 knockdown *in vitro* following delivery of 500 ng/mL Aha1 siRNA with 3.0 or 1.5 μg/ml ethoxyethylaminoacrylate + butyl acrylate (EEAA-BuA) copolymers.

| polymer | | cell type | | | | | | | | |
|---|---|---|---|---|---|---|---|---|---|---|
| | | Hep3B-SEAP | | MCF7 | | HT29 | | HepG2-SEAP | | A375 | |
| % Amine | MW | 3.0 μg/ml | 1.5 μg/ml | 3.0 μg/ml | 1.5 μg/ml | 3.0 μg/ml | 1.5 μg/ml | 3.0 μg/ml | 1.5 μg/ml | 3.0 μg/ml | 1.5 μg/ml |
| 42% | 30.2 | 81% | 80% | 56% | 56% | | | 71% | 48% | 74% | 75% |
| 42% | 63.0 | 90% | 87% | 75% | 68% | | | 62% | 44% | 85% | 72% |
| 42% | 87.6 | 89% | 75% | 64% | 56% | | | 59% | 33% | 81% | 71% |
| 53% | 26.6 | 54% | 79% | 14% | 20% | | | 42% | 27% | 38% | 40% |
| 53% | 53.2 | 72% | 85% | 34% | 44% | | | 45% | 29% | 78% | 65% |
| 53% | 78.4 | 82% | 86% | 49% | 54% | | | 56% | 38% | 80% | 79% |
| 73% | 47.1 | 44% | 45% | 22% | 21% | | | | | 41% | 33% |
| 73% | 72.3 | 48% | 46% | 33% | 17% | | | | | 54% | 43% |

FIG. 13

Poly(acrylate) Random Copolymers: Composition.

| polymer | amine monomer[j] | | | hydrophobic monomer[i] | | | Molecular weight kDa (×1000) | | RAFT[a] | PDI[e] |
|---|---|---|---|---|---|---|---|---|---|---|
| | | feed ratio (%) | actual ratio[b] (%) | | feed ratio (%) | actual ratio[b] (%) | theoretical[c] | calculated[d] | | |
| Lau 42101-24ABC-1 | ethoxyethyl | 72.5 | 68 | propyl meth | 27.5 | 32 | 50 | 30 | yes | 1.1 |
| Lau-41648-140-B frl | | 72.5 | 66 | | 27.5 | 34 | 50 | 21 | yes | 1.1 |
| Lau-42101-24A-1 | | 72.5 | 66 | | 27.5 | 34 | 50 | 24 | yes | 1.1 |
| Lau-42101-24B-1 | | 72.5 | 69 | | 27.5 | 31 | 50 | 25 | yes | 1.1 |
| Ant 41658-111 | | 75 | n.d. | | 25 | n.d. | 73 | 52 | yes | 1.2 |
| Ant 41658-111 frl | | 75 | n.d. | | 25 | n.d. | 87 | 62 | yes | 1.1 |
| NAR 41439-71B-frl | | 76 | 69 | | 24 | 31 | 86 | 61 | yes | 1.5 |
| Lau-41648-106 17-19 | | 80 | 74 | | 20 | 26 | | 42 | no | 1.2 |
| Lau 42101-43A-1 | ethoxyethyl | 80 | 74 | ethoxyethyl meth | 20 | 26 | 100 | 56 | yes | 1.2 |
| Lau 42101-43B-1 | | 75 | 70 | | 25 | 30 | 100 | 53 | yes | 1.2 |
| Lau 42101-43C-1 | | 70 | 62 | | 30 | 38 | 100 | 53 | yes | 1.2 |
| Lau 42101-43D-1 | | 65 | 57 | | 35 | 43 | 100 | 56 | yes | 1.2 |
| Lau 42101-44A-1 | ethoxyethyl | 80 | 75 | butoxyethyl meth | 20 | 25 | 100 | 60 | yes | 1.2 |
| Lau 42101-44B-1 | | 75 | 70 | | 25 | 30 | 100 | 56 | yes | 1.2 |
| Lau 42101-44C-1 | | 70 | 64 | | 30 | 36 | 100 | 60 | yes | 1.1 |
| Lau 42101-44D-1 | | 65 | 59 | | 35 | 41 | 100 | 62 | yes | 1.1 |
| Lau 1005-29A-1[f] | ethoxyethyl | 55 | 61 | sec-butyl | 45 | 39 | 100 | 49 | yes | 1.1 |
| Lau 42101-8D-1 | | 55 | 59 | | 45 | 41 | 100 | 47 | yes | 1.1 |

FIG. 14

| | | | | | | | | | | |
|---|---|---|---|---|---|---|---|---|---|---|
| Lau 1005-6C-1 | ethoxyethyl | 55 | 58 | propyl | 45 | 42 | 100 | 55 | yes | 1.1 |
| Lau 1005-6D-1 | ethoxyethyl | 50 | 53 | propyl | 50 | 47 | 100 | 56 | yes | 1.1 |
| Lau 1005-12H-1 | ethoxyethyl | 50 | 53 | butyl | 50 | 47 | 150 | 79 | yes | 1.2 |
| Lau 42101-13B-1 | ethoxyethyl | 65 | 66 | iso-amyl | 35 | 34 | 100 | 38 | yes | 1.3 |
| Lau 41305-38 17-19 | | 80 | n.d. | ethyl meth | 20 | n.d. | | 62 | no | 1.4 |
| Lau-41648-102 17-19 | propyl | 80 | 78 | ethyl meth | 20 | 23 | | 54 | no | 1.4 |
| Nar-41439-116A fr1 | propyl | 76 | 70 | ethyl meth | 24 | 30 | 79 | 56 | yes | 1.5 |
| Ant 40911-123-3 | | 80 | 74 | | 20 | 26 | 86 | 52 | no | 1.3 |
| Ant-41658-58 [g] | propyl | 70 | n.d. | butyl meth | 25 | n.d. | 133 | 92 | no | 1.1 |
| NAR 42020-117A-fr1 [h] | propyl | 76 | 65 | butyl meth | 24 | 30 | 190 | 128 | yes | 1.1 |
| Lau-42101-23D1 | propyl | 68 | 59 | ethoxyethyl meth | 32 | 41 | 50 | 39 | yes | 1.1 |
| NAR 41439-141B-fr1 | butyl | 79 | 67 | ethyl meth | 21 | 33 | 49 | 34 | yes | 1.1 |

[a] - polymer synthesized by RAFT polymerization
[b] - amine content experimentally determined
[c] - theoretical molecular weight of protected polymer
[d] - molecular weight for deprotected polymer calculated from experimentally measured molecular weight for protected polymer
[e] - polydispersity measured for protected polymer
[f] - polymer also contained 0.001% 9-anthracenylmethyl acrylate feed ratio which is not expected to affect biological properties of the polymer
[g] - polymer also contained 5% octadecyl monomer feed ratio
[h] - polymer also contained 5% octadecyl monomer feed and actual ratios
[i] - corresponds to group R of formula (I) or (Ia), "meth" signifies methacrylate monomer
[j] - corresponds to spacer group Y of formula (I) or (Ia)
n.d. = not determined

FIG. 14 cont.

*In vivo* gene knockdown following injection of reversibly masked polymer conjugated to siRNA.

| polymer | | masking [b] | | siRNA | | species | n | injection | | harvest (days) | % gene inhibition |
|---|---|---|---|---|---|---|---|---|---|---|---|
| | amount | | | gene | amount | | | site | vol. | | |
| isotonic glucose [a] | | | | | | | | | | | 0 |
| Lau 42101-8D | 250 μg | 2x FC-PEG(24) | 6x AC-NAG | Factor VII | 20 μg | mouse | 3 | subQ [c] | 300 μL | 5 | 91 |
| | 500 μg | 2x FC-PEG(24) | 6x AC-NAG | Factor VII | 50 μg | mouse | 3 | subQ | 300 μL | 5 | 99 |
| | 200 μg | 2x FC-PEG(12) | 6x AC-NAG | Factor VII | 10 μg | mouse | 3 | IV | 300 μL | 2 | 96 |
| | 100 μg | 4.7x CDM-PEG | 2.3x CDM-NAG | Factor VII | 10 μg | mouse | 3 | IV | 300 μL | 2 | 94 |
| | 250 μg (1 mg/kg) | 4.7x CDM-PEG | 2.3x CDM-NAG | Factor VII | 50 μg | rat | 3 | IV | 1000 μL | 2 | 93 |
| Lau-42101-24A-1 | 250 μg | 4.7x CDM-PEG | 2.3x CDM-NAG | Factor VII | 50 μg | rat | 3 | IV | 1000 μL | 2 | 91 |
| | 2500 μg | 4.7x CDM-PEG | 2.3x CDM-NAG | Factor VII | 50 μg | rat | 3 | IV | 1000 μL | 2 | 100 |
| | 250 μg | 2x FC-PEG(24) | 6x FC-NAG | Factor VII | 50 μg | rat | 3 | IV | 1000 μL | 2 | 15 |
| | 2500 μg | 2x FC-PEG(24) | 6x FC-NAG | Factor VII | 50 μg | rat | 3 | IV | 1000 μL | 2 | 99 |
| | 250 μg | 2x FC-PEG(24) | 5x CDM-NAG | Factor VII | 50 μg | rat | 3 | IV | 1000 μL | 2 | 42 |
| | 250 μg | 2x AN-PEG | 5x CDM-NAG | Factor VII | 50 μg | rat | 3 | IV | 1000 μL | 2 | 55 |
| | 250 μg | 2x VC-PEG | 5x CDM-NAG | Factor VII | 50 μg | rat | | IV | 1000 μL | 2 | 40 |
| | 250 μg | | | Factor VII | 50 μg | rat | 3 | IV | 1000 μL | 2 | 43 |
| Lau-42101-23D-1-fr1 | 150 μg | 4.7x CDM-PEG | 2.3x CDM-NAG | Factor VII | 40 μg | mouse | | IV | 400 μL | 2 | 95 |

FIG. 15

|  |  |  |  |  |  |  |  |  |
|---|---|---|---|---|---|---|---|---|
|  | 500 µg | 2x FC-PEG(24) | 6x AC-NAG | Factor VII | 50 µg | mouse | 3 | subQ | 300 µl | 5 | 99 |
|  | 100 µg | 2x FC-PEG(12) | 6x AC-NAG | Factor VII | 10 µg | mouse | 3 | IV | 300 µL | 3 | 52 |
|  | 300 µg | 4.7x CDM-PEG | 2.3x CDM-NAG | ApoB | 10 µg | mouse | 3 | IV | 200 µl | 3 | 50 |
| Lau 41648-140-B | 5 mg/kg | 4.7x CDM-PEG | 2.3x CDM-NAG | control | 1 mg/kg | primate |  | IV | 2 mL/kg | 8 | 7[d] |
|  | 0.5 mg/kg | 4.7x CDM-PEG | 2.3x CDM-NAG | Factor VII | 0.1 mg/kg | primate |  | IV | 2 mL/kg | 8 | 80 |
|  | 1 mg/kg | 4.7x CDM-PEG | 2.3x CDM-NAG | Factor VII | 0.2 mg/kg | primate |  | IV | 2 mL/kg | 8 | 94 |
|  | 2.5 mg/kg | 4.7x CDM-PEG | 2.3x CDM-NAG | Factor VII | 0.5 mg/kg | primate |  | IV | 2 mL/kg | 8 | 90 |
| Lau 29A-1 | 5000 µg (20 mg/kg) | 2x FC-PEG(12) | 6x AC-NAG | Factor VII | 250 µg | rat | 3 | subQ | 500 µL | 7 | 59 |
|  | 750 µg | 2x FC-PEG(12) | 6x AC-NAG | Factor VII | 50 µg | rat | 3 | IV | 1000 µL | 10 | 72 |
| Ant-41658-111 | 500 µg | 4.7x CDM-PEG | 2.3x CDM-NAG | Factor VII | 50 µg | mouse | 3 | subQ | 300 µL | 5 | 51 |

[a] - isotonic glucose control

[b] - numbers represent of mg masking agent per mg polymer

[c] - subQ signifies subcutaneous injection

[d] - compared to day 1

FIG. 15 cont.

*In vivo gene knockdown following co-injection of reversibly masked polymer and cholesterol-siRNA.*

| polymer | | masking[b] | | siRNA | | species | n | injection | | harvest (days) | % gene inhibition |
|---|---|---|---|---|---|---|---|---|---|---|---|
| | amount | | | gene | amount | | | site | vol. (μL) | | |
| isotonic glucose[a] | | | | | | | | | | | 0 |
| Ant-41658-111 | 150 μg | 4.7x CDM-PEG | 2.3x CDM-NAG | ApoB | 40 μg | mouse | 3 | IV | 200 μL | 2 | 86 |
| Lau 42101-8D | 150 μg | 4.7x CDM-PEG | 2.3x CDM-NAG | ApoB | 40 μg | mouse | 3 | IV | 200 μL | 2 | 82 |
| | 500 μg | 2x FC-PEG(24) | 6x AC-NAG | Factor VII | 100 μg | mouse | 3 | subQ[c] | 300 μL | 5 | 80 |
| | 300 μL | 2x FC-PEG(12) | 6x AC-NAG | Factor VII | 100 μg | mouse | 3 | IV | 300 μL | 2 | 99 |
| Ant 123-3 | 1250 μg | 4.7x CDM-PEG | 2.3x CDM-NAG | Factor VII | 750 μg | rat | | IV | 1000 μL | 2 | 85 |

[a] - isotonic glucose control
[b] - numbers represent of mg masking agent per mg polymer
[c] - subQ signifies subcutaneous injection

FIG. 16

```
SEQUENCE LISTING

<160> NUMBER OF SEQ ID NOS: 10

<210> SEQ ID NO 1
<211> LENGTH: 20
<212> TYPE: DNA
<213> ORGANISM: Mus musculus

<400> SEQUENCE: 1
gcaaaggcgu gccaacucat                                                   20

<210> SEQ ID NO 2
<211> LENGTH: 21
<212> TYPE: DNA
<213> ORGANISM: Mus musculus

<400> SEQUENCE: 2
tgaguuggca cgccuuugct t                                                 21

<210> SEQ ID NO 3
<211> LENGTH: 21
<212> TYPE: DNA
<213> ORGANISM: Mus musculus

<400> SEQUENCE: 3
ggaucaucuc aagucuuact t                                                 21

<210> SEQ ID NO 4
<211> LENGTH: 21
<212> TYPE: DNA
<213> ORGANISM: Mus musculus

<400> SEQUENCE: 4
guaagacuug agaugaucct t                                                 21
```

```
<210> SEQ ID NO 5
<211> LENGTH: 24
<212> TYPE: DNA
<213> ORGANISM: Macaca fascicularis

<400> SEQUENCE: 5
uuagguuggu gaauggagcu cagt                                              24

<210> SEQ ID NO 6
<211> LENGTH: 21
<212> TYPE: DNA
<213> ORGANISM: Macaca fascicularis

<400> SEQUENCE: 6
cugagcucca uucaccaact t                                                 21

<210> SEQ ID NO 7
<211> LENGTH: 21
<212> TYPE: DNA
<213> ORGANISM: Rattus norvegicus

<400> SEQUENCE: 7
ggaaucuuau auuugaucca a                                                 21

<210> SEQ ID NO 8
<211> LENGTH: 23
<212> TYPE: DNA
<213> ORGANISM: Rattus norvegicus

<400> SEQUENCE: 8
uuggaucaaa uauaagauuc ccu                                               23

<210> SEQ ID NO 9
<211> LENGTH: 23
<212> TYPE: DNA
<213> ORGANISM: Photinus pyralis

<400> SEQUENCE: 9
uaucuuacgc ugaguacuuc gat                                               23

<210> SEQ ID NO 10
<211> LENGTH: 21
<212> TYPE: DNA
<213> ORGANISM: Photinus pyralis

<400> SEQUENCE: 10
ucgaaguacu cagcguaagt t                                                 21
```

POLY(ACRYLATE) POLYMERS FOR IN VIVO NUCLEIC ACID DELIVERY

CROSS-REFERENCE TO RELATED APPLICATIONS

This application claims the benefit of U.S. Provisional Application No. 61/625,955 filed 18 Apr. 2012.

BACKGROUND OF THE INVENTION

The delivery of polynucleotides and other substantially cell membrane impermeable compounds into a living cell is highly restricted by the complex membrane system of the cell. Drugs used in antisense, RNAi, and gene therapies are relatively large hydrophilic polymers and are frequently highly negatively charged. Both of these physical characteristics preclude their direct diffusion across the cell membrane. For this reason, the major barrier to polynucleotide delivery is the delivery of the polynucleotide across a cell membrane to the cell cytoplasm or nucleus.

One means that has been used to deliver small nucleic acid in vivo has been to attach the nucleic acid to either a small targeting molecule or a lipid or sterol. While some delivery and activity has been observed with these conjugates, the nucleic acid dose required with these methods has been prohibitively large for practical application.

Numerous transfection reagents have been developed that achieve reasonably efficient delivery of polynucleotides to cells in vitro. However, in vivo delivery of polynucleotides using these same transfection reagents is complicated and rendered ineffective by in vivo toxicity, serum interactions, and poor targeting. Transfection reagents that work well in vitro, cationic polymers and lipids, typically form large electrostatic particles and destabilize cell membranes. The positive charge of in vitro transfection reagents facilitates association with nucleic acid via charge-charge (electrostatic) interactions thus forming the nucleic acid/transfection reagent complex. Positive charge is also beneficial for non-specific binding of the vehicle to the cell and for membrane fusion, destabilization, or disruption. Destabilization of membranes facilitates delivery of the substantially cell membrane impermeable polynucleotide across a cell membrane. While these properties facilitate nucleic acid transfer in vitro, they cause toxicity and ineffective targeting in vivo. Cationic charge results in interaction with serum components, which causes destabilization of the polynucleotide-transfection reagent interaction and poor bioavailability and targeting. Membrane activity of transfection reagents, which can be effective in vitro, often leads to toxicity in vivo.

For in vivo delivery, the vehicle (nucleic acid and associated delivery agent) should be small, less than 100 nm in diameter, and preferably less than 50 nm. Even smaller complexes, less than 20 nm or less than 10 nm would be more useful yet. Delivery vehicles larger than 100 nm have very little access to cells other than blood vessel cells in vivo. Complexes formed by electrostatic interactions tend to aggregate or fall apart when exposed to physiological salt concentrations or serum components. Further, cationic charge on in vivo delivery vehicles leads to adverse serum interactions and therefore poor bioavailability. Interestingly, high negative charge can also inhibit in vivo delivery by interfering with interactions necessary for targeting. Thus, near neutral vehicles are desired for in vivo distribution and targeting. Without careful regulation, membrane disruption or destabilization activities are toxic when used in vivo. Balancing vehicle toxicity with nucleic acid delivery is more easily attained in vitro than in vivo.

Rozema et al., in U.S. Patent Publication 20040162260 demonstrated a means to reversibly regulate membrane disruptive activity of a membrane active polyamine by reversible conversion of primary amines to pairs of carboxyl groups (β carboxyl and γ carboxyl of 2-propionic-3-methylmaleic anhydride). Rozema et al. (Bioconjugate Chem. 2003, 14, 51-57) reported that the β carboxyl did not exhibit a full apparent negative charge and by itself was not able to inhibit membrane activity. The addition of the γ carboxyl group was reported to be necessary for effective membrane activity inhibition. However, because the vehicle was highly negatively charged, with both the nucleic acid and the modified polymer having high negative charge density, this system was not efficient for in vivo delivery.

By substituting neutral hydrophilic targeting (galactose) and steric stabilizing (PEG) groups for the γ carboxyl of 2-propionic-3-methylmaleic anhydride, Rozema et al. were able to retain overall water solubility and reversible inhibition of membrane activity while incorporating effective in vivo hepatocyte cell targeting (U.S. Patent Publication 20080152661).

We now describe new membrane active polymers and compositions made with the described polymers for use in delivery of nucleic acids to cells in vivo. These new polymers provide improved therapeutic potential over those previously described.

SUMMARY OF THE INVENTION

In a preferred embodiment, the invention features amphipathic cationic poly(acrylate) random copolymers particularly suited for delivering polynucleotides to cells in vivo. An amphipathic cationic poly(acrylate) random copolymer of the invention comprises a plurality of amine-containing acrylate monomers and a plurality of first hydrophobic acrylate monomers. The amine-containing monomers contain pendant primary amine groups. The hydrophobic monomers contain pendent hydrophobic groups having 2-20 carbon atoms selected from the group consisting of: hydrocarbon group, alkyl group, alkenyl group, alkynyl group, alkoxy alkyl group, aromatic group, and aryl group. The polymers may further comprise a plurality of second amine-containing acrylate monomers or a plurality of second hydrophobic acrylate monomers. Second amine-containing acrylate monomers contain pendant amine groups selected from the group consisting of: primary amine, secondary amine, tertiary amine, quaternary amine, protected amine, nitrogen heterocycle, aldimine, hydrazide, hydrazone, and imidazole. In addition to being amphipathic, the poly(acrylate) random copolymers of the invention are membrane active. A preferred poly(acrylate) random copolymer comprises primary amine-containing and alkyl acrylate monomers.

Poly(acrylate) random copolymers of the invention may be synthesized from two, three, or four different monomers. Monomers may be selected from the list comprising: protected amine acrylate, imidazole acrylate, alkyl acrylate, alkenyl acrylate, alkynyl acrylate, aromatic acrylate, and aryl acrylate. Protected amine acrylate monomers include, but are not limited to: tert-Butoxycabonyl (Boc) protected amine containing acrylate. Protected primary amine monomers are copolymerized with alkyl acrylate monomers. The amine protecting groups are then removed post-polymerization to form aqueous soluble, amphipathic random copolymers. The aliphatic hydrophobic groups may be linear, branched, or cyclic and may contain one or more substitutions of heteroatoms.

In a preferred embodiment, poly(acrylate) random copolymers are synthesized by Reversible Addition-Fragmentation chain Transfer (RAFT) polymerization. In one embodiment, the RAFT polymerization is carried out using Malonate N,N-diphenyl dithiocarbamate (MDP-DTC). Using RAFT polymerization, and optionally fractionization, polymers having a polydispersity of less than 1.5, or more preferably less than 1.4 or 1.3 are possible.

For delivery of a polynucleotide to a cell in vivo, the described amphipathic poly(acrylate) random copolymers are reversibly modified. Reversible modification comprises attachment of a plurality of masking agents, as defined herein, to polymer primary amines through a plurality of reversible physiologically labile covalent bonds. Reversible physiologically labile covalent bonds may be selected from the group comprising: pH labile bonds and enzymatically cleavable bonds. As used herein, reversible modification means polymer primary amines are restored upon cleavage of the physiologically labile covalent bond linking the masking agent to the polymer. In a preferred embodiment, more than 50%, more than 60%, more than 70%, more than 80%, or more than 90% of polymer primary amines are modified by reversible attachment of masking agents. Masking agents may be selected from the group comprising: steric stabilizers and targeting groups. The masking agents improve biodistribution or targeting of the polymer or a polymer-polynucleotide conjugate in vivo. Masking agents may inhibit non-specific interactions of the polymer with serum components or non-target cells. Masking agents may reduce aggregation of the polymer or polymer-polynucleotide conjugate. Masking agents containing targeting groups enhance cell-specific targeting or cell internalization by targeting the conjugate system to a cell surface receptor. The masking agents can be conjugated to the polymer prior to or subsequent to conjugation of the polymer to a polynucleotide.

In another preferred embodiment, a polynucleotide is linked to the polymer of the invention through a second physiologically labile covalent bond. One or more polynucleotides may be linked to the polymer via the second physiologically labile covalent bonds. The labile bond linking the masking agent to the polymer, first labile bond, and the labile bond linking the polynucleotide to the polymer, second labile bond, maybe cleaved under the same or similar conditions or they may be cleaved under distinct conditions, i.e. they may be orthogonal labile bonds. The polynucleotide may be selected from the group comprising: DNA, RNA, blocking polynucleotide, oligonucleotide, RNA interference polynucleotide, siRNA, microRNA, mRNA, and shRNA. Second physiologically labile covalent bonds may be selected from the group comprising: pH labile bonds, enzymatically cleavable bonds, disulfide bonds, and nucleic acid ester bonds.

In a preferred embodiment, we describe a composition comprising: an amphipathic poly(acrylate) random copolymer covalently linked to: a) one or more targeting groups and or steric stabilizers via reversible physiologically labile covalent bonds; and, b) one or more polynucleotides via orthogonal second physiologically labile covalent bonds. The polynucleotide-polymer conjugate is administered to a mammal in a pharmaceutically acceptable carrier or diluent.

In a preferred embodiment, we describe a polymer conjugate system for delivering a membrane impermeable molecule to a cell and releasing the molecule in the cell. The polymer conjugate system comprises the membrane impermeable molecule reversibly linked to a reversibly modified poly(acrylate) of the invention. A preferred membrane impermeable molecule comprises a polynucleotide. A preferred polynucleotide comprises an RNA interference polynucleotide. A preferred RNA interference polynucleotide comprises an siRNA or miRNA. The polymer or polynucleotide-polymer conjugate is administered to a mammal in a pharmaceutically acceptable carrier or diluent.

In another preferred embodiment, the invention features a composition for delivering an RNA interference polynucleotide to a liver cell in vivo comprising: an amphipathic poly (acrylate) random copolymer covalently linked to: one or more targeting groups and/or steric stabilizers via reversible physiologically labile covalent bonds and an RNA interference polynucleotide conjugated to a polynucleotide targeting group (polynucleotide conjugate). A preferred polynucleotide targeting group is a hydrophobic group containing at least 20 carbon atoms. Another preferred polynucleotide targeting group is a trivalent galactosamine. The poly(acrylate) and the polynucleotide-conjugate are synthesized separately and may be supplied in separate containers or a single container. In this composition, the polynucleotide is not conjugated to the polymer. The modified polymer and polynucleotide-conjugate are administered to a mammal in pharmaceutically acceptable carriers or diluents. In one embodiment, the delivery polymer and the RNAi polynucleotide conjugate may be combined in a solution prior to administration to the mammal. In another embodiment, the delivery polymer and the RNAi polynucleotide conjugate may be co-administered to the mammal in separate solutions. In yet another embodiment, the delivery polymer and the RNAi polynucleotide conjugate may be administered to the mammal sequentially. For sequential administration, the delivery polymer may be administered prior to administration of the RNAi polynucleotide conjugate. Alternatively, for sequential administration, the RNAi polynucleotide conjugate may be administered prior to administration of the delivery polymer.

In another embodiment, the described amphipathic poly (acrylate) random copolymers are suitable for delivering polynucleotides to mammalian cells in vitro. For in vitro cell delivery, the amphipathic poly(acrylate) random copolymers may be reversibly modified as described or used without reversible modification. They may also be combined with lipids or other polymers.

BRIEF DESCRIPTION OF THE FIGURES

FIG. 1. Illustration showing the structure of a membrane active amphipathic poly(acrylate) random copolymer wherein:

N is a primary amine having the form —$NH_2$,

N' is a secondary, tertiary, or quaternary amine having the form —$NR^5H$, —$NR^5R^6$, or —$NR^5R^6R^7$ wherein $R^5$, $R^6$, and $R^7$ are independently selected from —$CH_3$ and —$CH_2$—$CH_3$, or alternatively N' can be a nitrogen heterocycle, aldimine, hydrazide, hydrazone, or imidazole, Y and Y' are linker groups, R and R' are hydrophobic groups independently having 2-20 carbon atoms or alkoxyl alkyl groups, R1, R2, R3, and R4 are independently selected from hydrogen (—H) and methyl (—$CH_3$), m and p are integers greater than zero (0), n and q are integers greater than or equal to zero (0), and the ratio (m+n)/(p+q) is 0.67-9 (40-90% amines).

Figure 1:
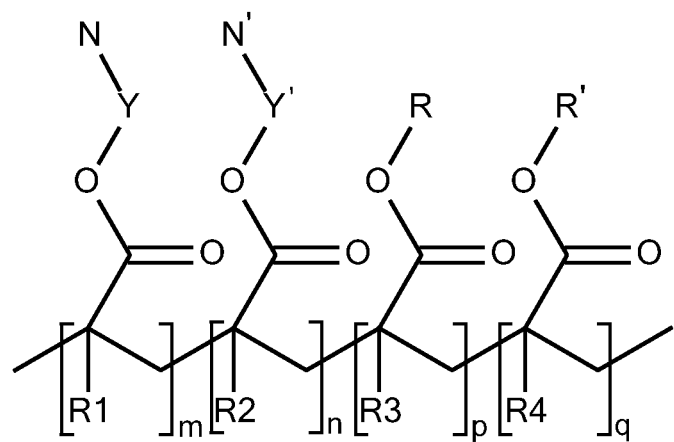
Figure 2:
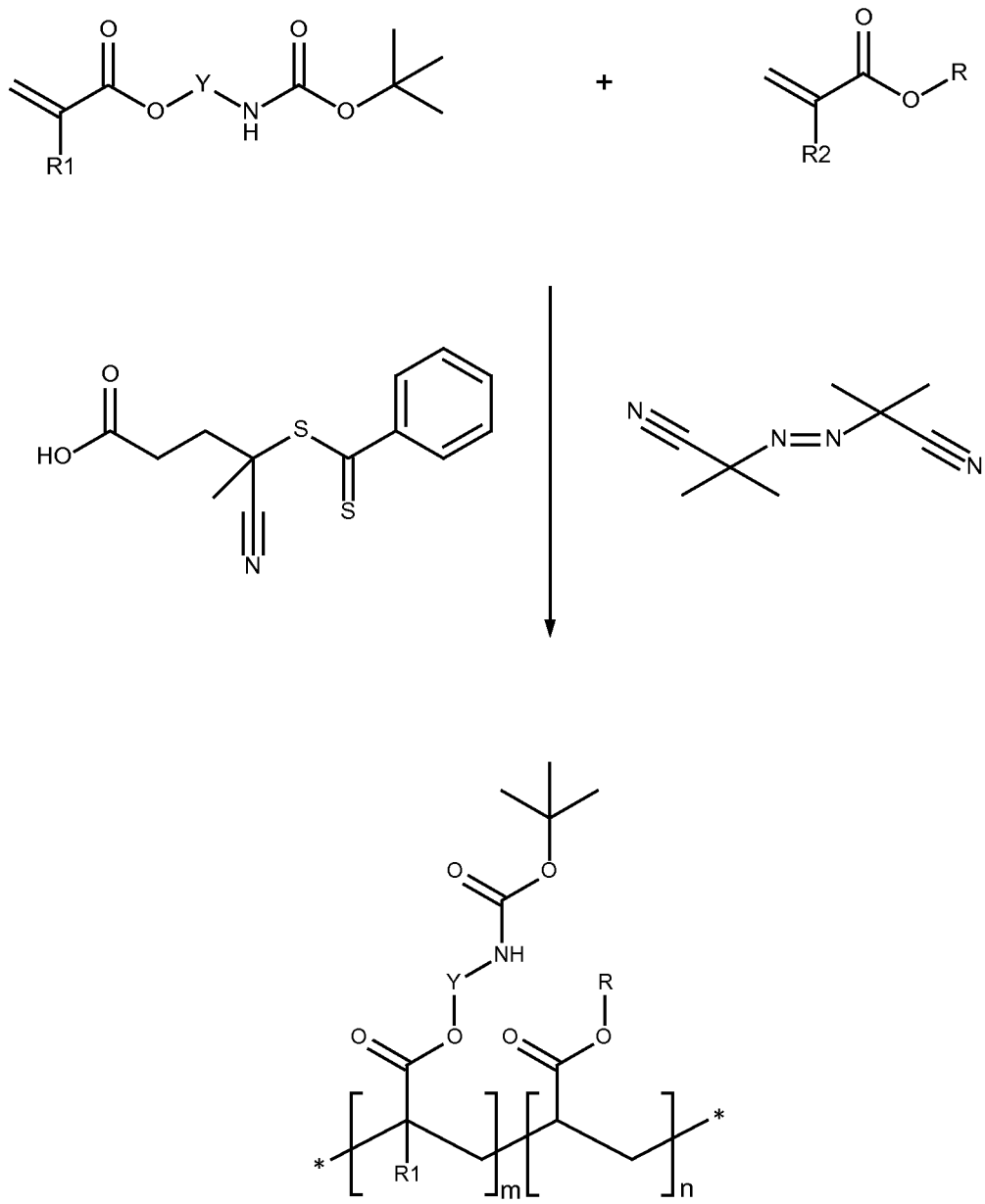

FIG. 2. Illustration showing the general reaction scheme for RAFT polymerization of amphipathic poly(acrylate) random copolymers of the invention wherein Y, R1, R2, R, m, and n are as defined in FIG. 1.

Figure 3:
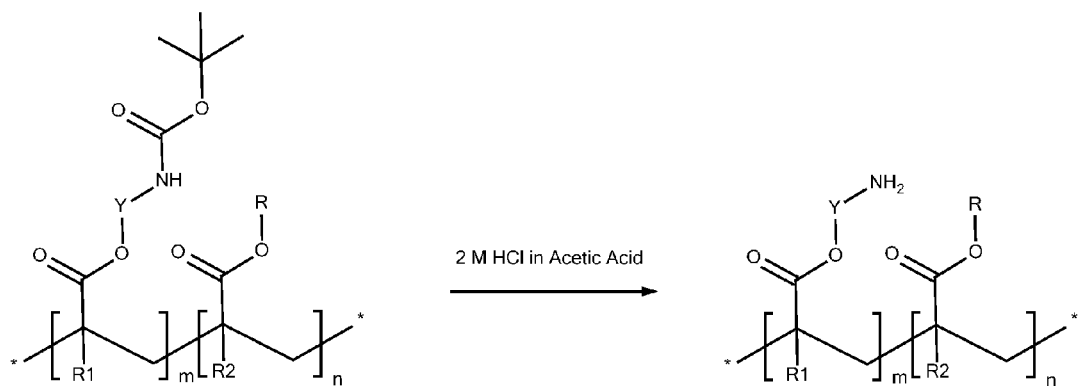

FIG. 3. Illustration showing the general reaction scheme for Amine Deprotection of Polymers wherein Y, R1, R2, R, m, and n are as defined in FIG. 1.

FIG. 4. Illustration showing the structures of various exemplary suitable RAFT Reagents.

Figure 5:
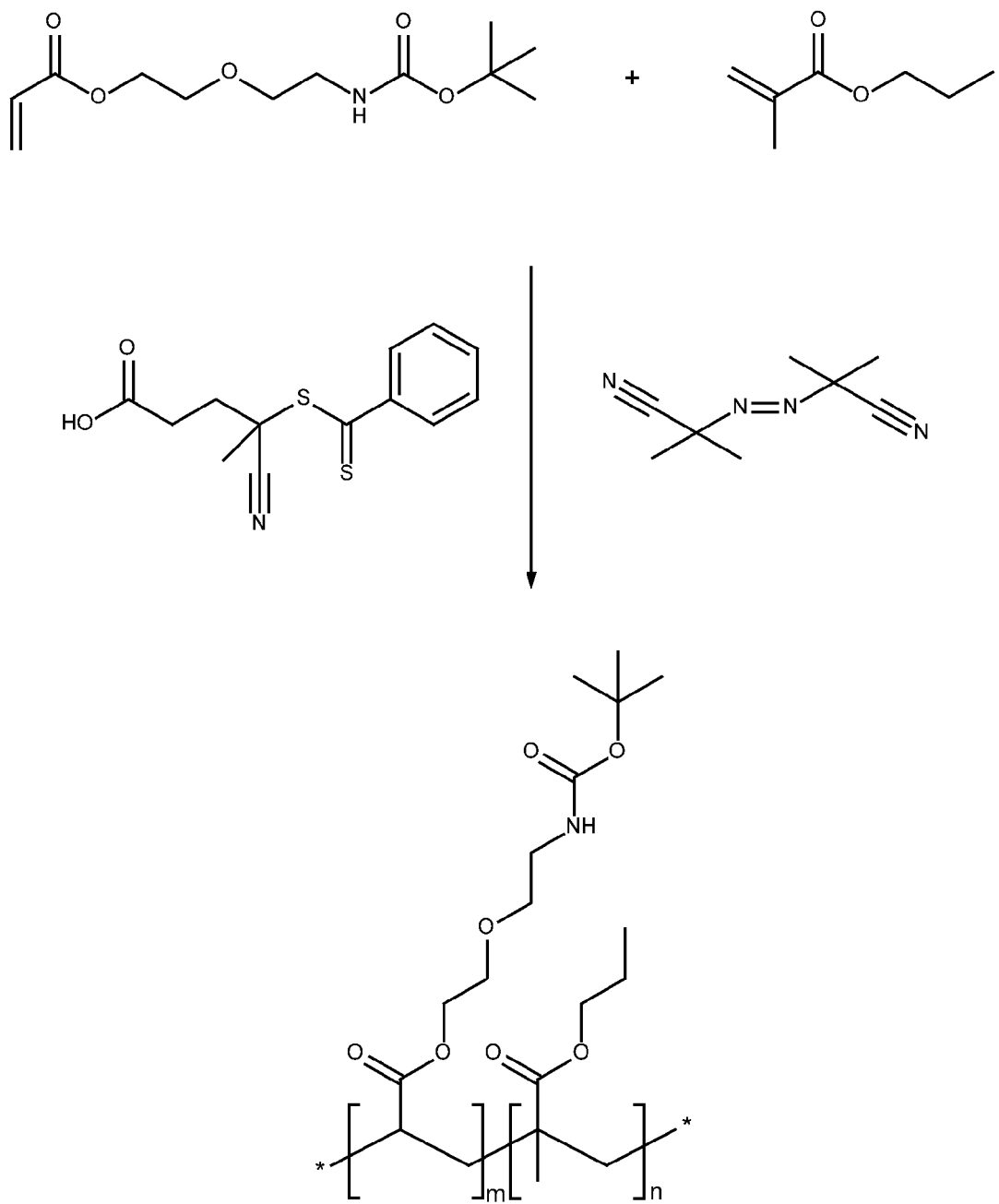

FIG. 5. Illustration showing the general reaction scheme for RAFT polymerization of amine protected polymer LAU 41648-140-B-fr1.

Figure 6:
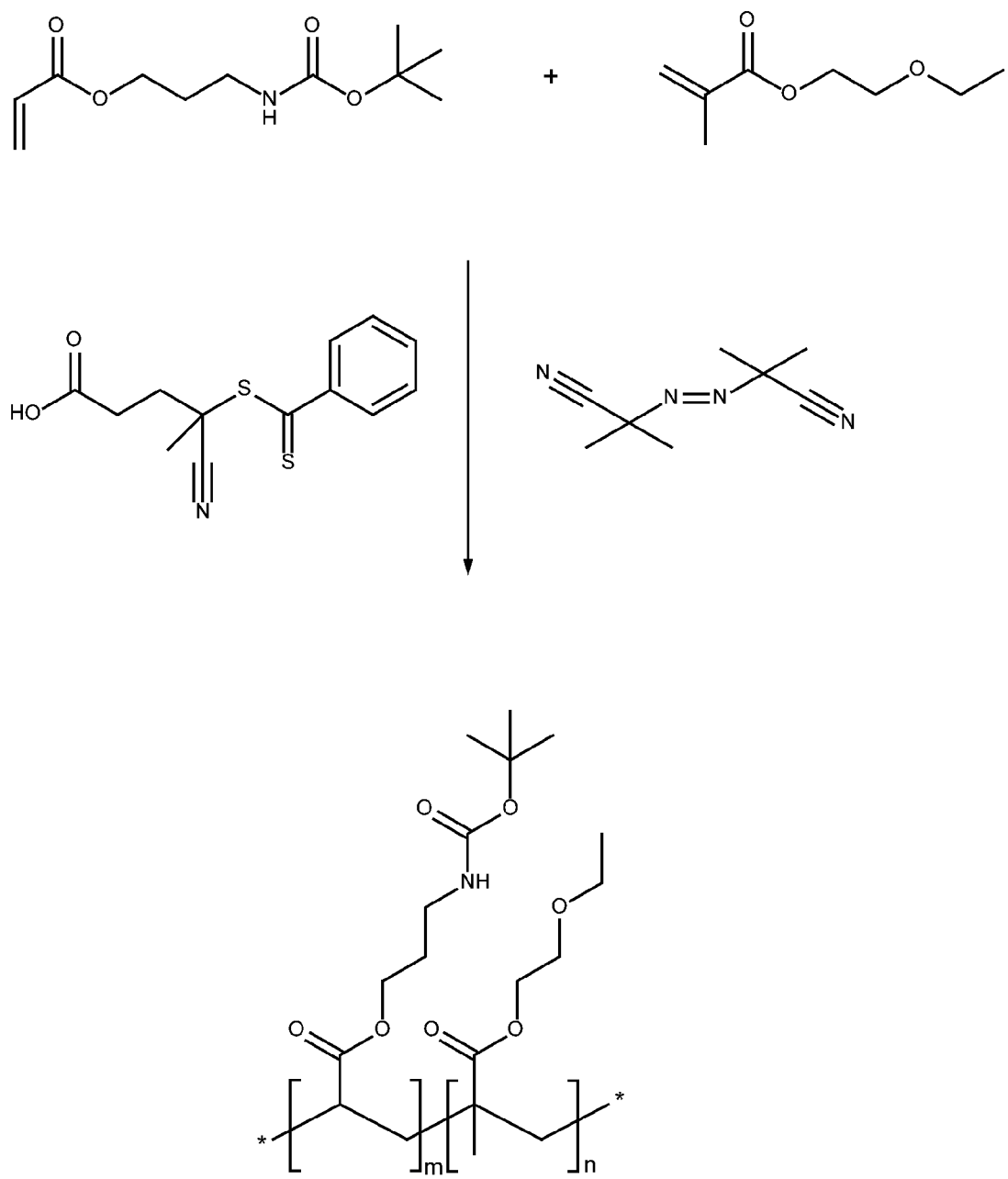

FIG. 6. Illustration showing the general reaction scheme for RAFT polymerization of amine protected polymer LAU 42101-23-D-fr1.

Figure 7:
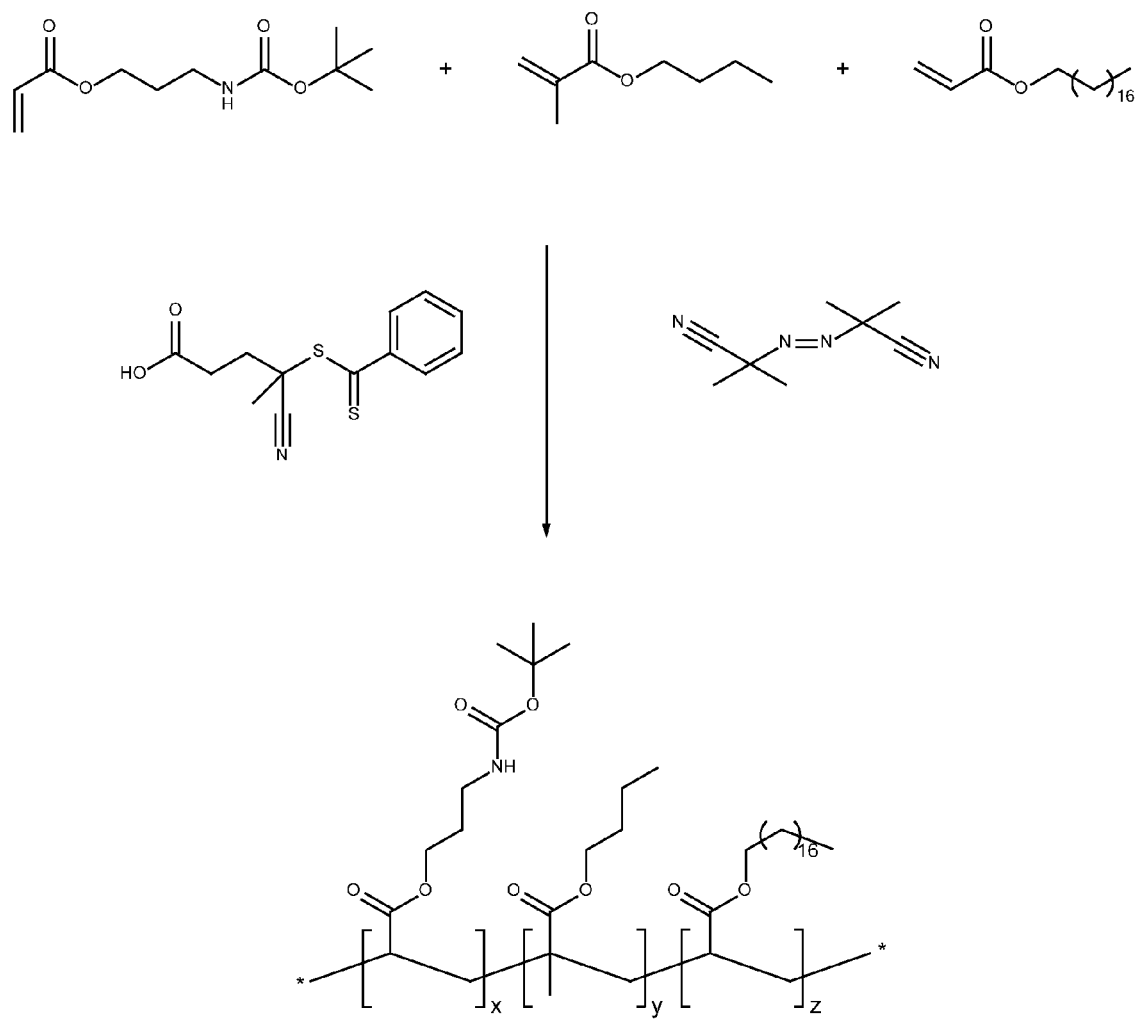

FIG. 7. Illustration showing the general reaction scheme for RAFT polymerization of amine protected polymer NAR 42020-117A-fr1.

Figure 8:
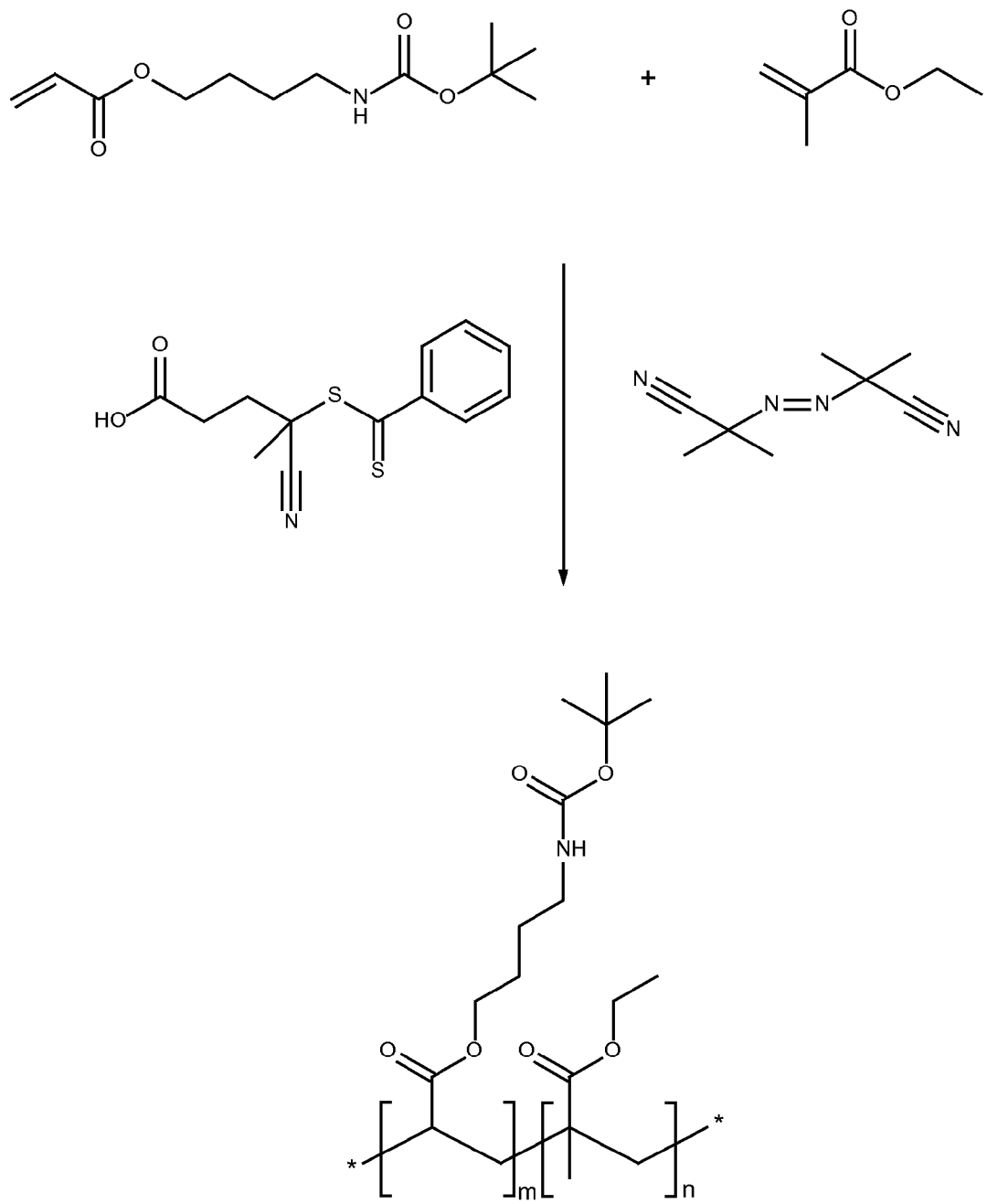

FIG. 8. Illustration showing the general reaction scheme for RAFT polymerization of amine protected polymer NAR 41439-141B-fr1.

Figure 9:
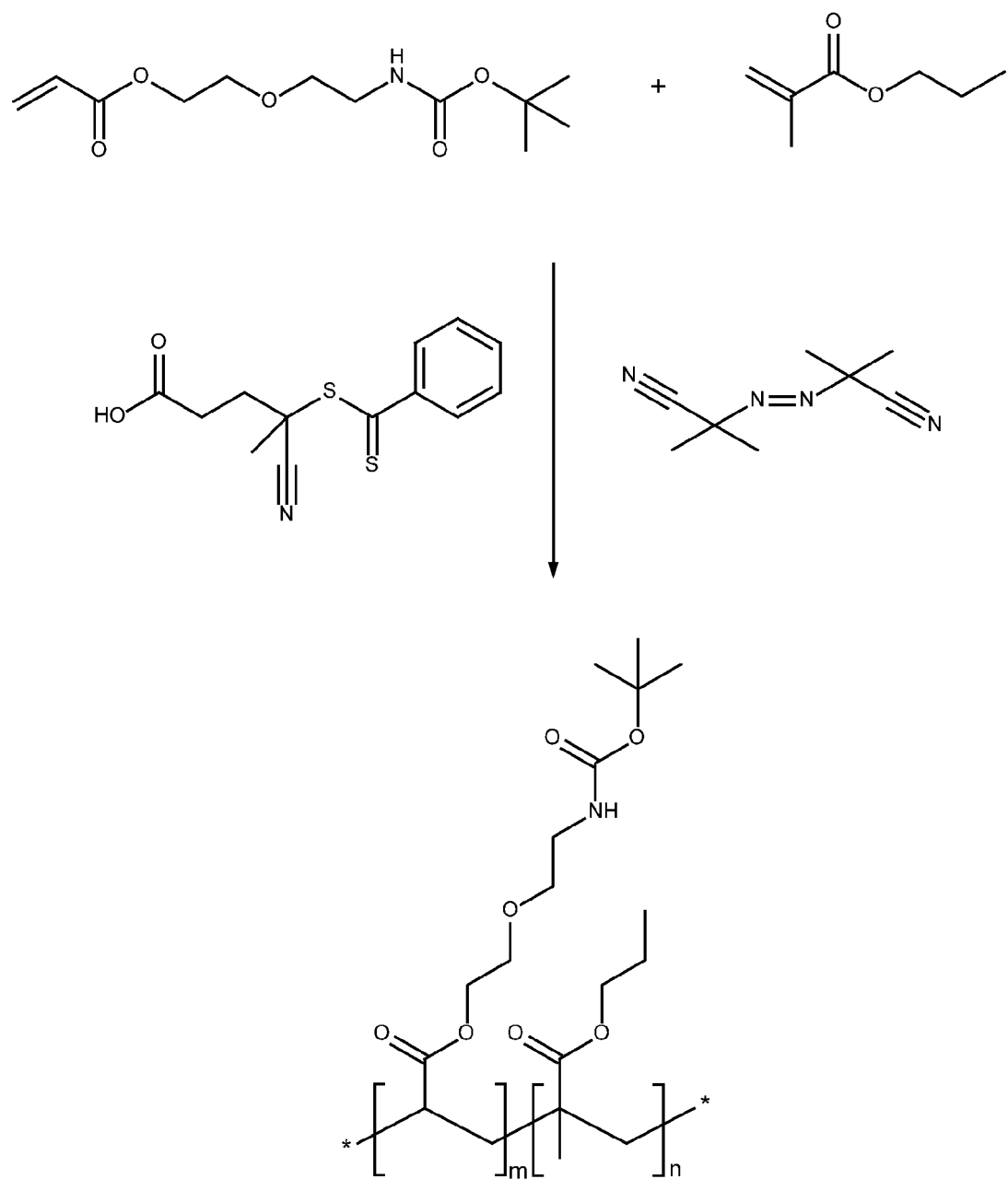

FIG. 9. Illustration showing the general reaction scheme for RAFT polymerization of amine protected polymer NAR 41439-71B-fr1.

Figure 10:
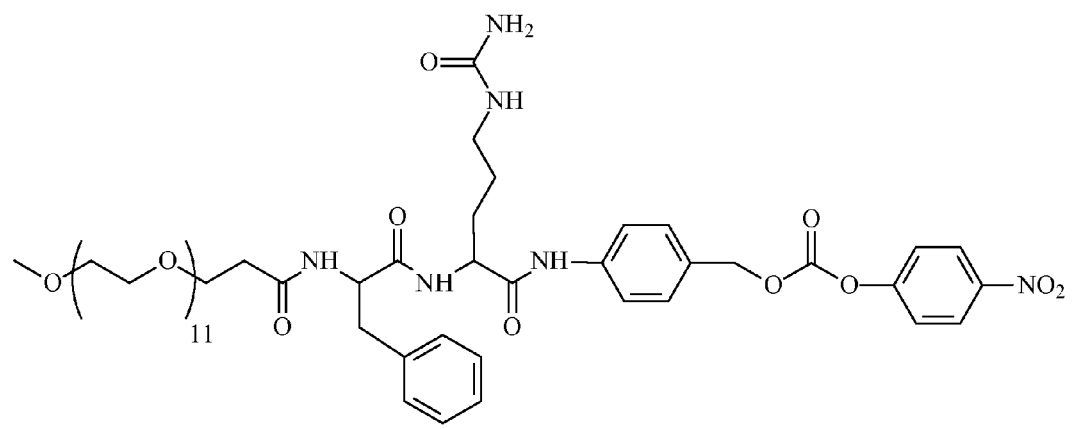

FIG. 10. Illustration showing the structures of various exemplary dipeptide masking agents.

FIG. 11. Table showing percent Aha1 gene knockdown in various cell types in vitro following delivery of 500 ng/mL Aha1 siRNA with 3.0 or 1.5 µg/ml ethylaminoacrylate+butyl methacrylate (EAA-BuMA) copolymers.

FIG. 12. Table showing percent Aha1 gene knockdown in various cell types in vitro following delivery of 500 ng/mL Aha1 siRNA with 3.0 or 1.5 µg/ml ethoxyethylaminoacrylate+sec-butyl acrylate (EEAA-SecBuA) copolymers.

FIG. 13. Table showing percent Aha1 gene knockdown in various cell types in vitro following delivery of 500 ng/mL Aha1 siRNA with 3.0 or 1.5 µg/ml ethoxyethylaminoacrylate+butyl acrylate (EEAA-BuA) copolymers.

FIG. 14. Table listing amphipathic poly(acrylate) random copolymers of the invention and their compositions.

FIG. 15. Table showing percent knockdown of target gene expression in vivo following administration of masked poly(acrylate) polymers of the invention conjugate to siRNA.

FIG. 16. Table showing percent knockdown of target gene expression in vivo following co-administration of masked poly(acrylate) polymers of the invention together with cholesterol-siRNA.

DETAILED DESCRIPTION OF THE INVENTION

The present invention relates to amphipathic poly(acrylate) random copolymers and conjugate systems thereof useful for the delivery of biologically active substances, such as nucleic acids, peptides, and proteins. The delivery of nucleic acids and other substantially cell membrane impermeable compounds into a living cell is highly restricted by the complex membrane system of the cell. For in vivo delivery the amphipathic poly(acrylate) random copolymers are reversibly modified by covalent attachment of masking agents via physiologically labile linkages.

In one embodiment, the present invention is directed to membrane active poly(acrylate) random copolymers of formula (I):

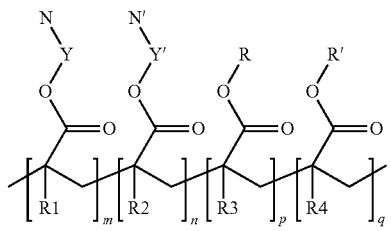

wherein:

N is a primary amine having the form —NH$_2$,

N' is a secondary, tertiary, or quaternary amine having the form —NR$^5$H, —NR$^5$R$^6$, or —NR$^5$R$^6$R$^7$ wherein R$^5$, R$^6$, and R$^7$ are independently selected from —CH$_3$ and —CH$_2$—CH$_3$, or alternatively N' can be a nitrogen heterocycle, aldimine, hydrazide, hydrazone, or imidazole, Y and Y' are linker groups, R and R' are hydrophobic groups as defined herein independently having 2-20 carbon atoms or alkoxyl ethyl groups, —(CH$_2$)$_l$—O—CH$_2$—CH$_3$, wherein l is 2, 3, or 4 (a preferred alkoxy alkyl group is a 2-ethoxyethyl group, —(CH$_2$)$_2$O—CH$_2$—CH$_3$), R1, R2, R3, and R4 are independently selected from hydrogen (—H) and methyl (—CH$_3$), m and p are integers greater than zero (0), n and q are integers greater than or equal to zero (0), and the ratio (m+n)/(p+q) is 0.67-5.7 (40-85% amines) and more preferably 1.2-4 (55-80% amines).

A preferred R group is a hydrophobic group having 2-6 carbon atoms.

Linker groups Y and Y' are uncharged and link the nitrogen to the acrylate via 1-24 carbon atoms, one or more of which may be substituted for heteroatoms. In a preferred embodiment, Y and Y' independently contain 1-12 carbon atoms, one or more of which may be substituted for heteroatoms. In one embodiment, Y and Y' are independently selected from —(CH$_2$)$_x$— and —(CH$_2$—CH$_2$—O)$_z$—(CH$_2$)$_x$—, wherein x and z are independently 1, 2, 3, 4, 5, or 6.

In another embodiment, a monomer such as a fluorescent monomer, may be incorporated in the polymer to aid in experimental detection. An exemplary fluorescent monomer is 9-anthracenylmethyl acrylate. Such monomers are incorporated at a very low percentage, less than 0.005, such that they are not expected to significantly affect the biological properties of the polymer.

In one embodiment, the present invention is directed to acrylate random copolymers of formula (Ia):

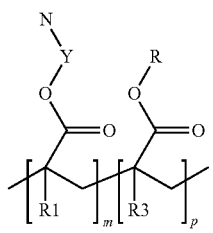

wherein:
N is a primary amine having the form —NH$_2$,
Y is a linker group as described above,
R is a hydrophobic group as defined herein having 2-6 carbon atoms or an alkoxyl alkyl group, —(CH$_2$)$_l$—O—CH$_2$—CH$_3$, wherein l is 2, 3, or 4 (preferably 2-ethoxyethyl),
R1 and R3 are independently selected from hydrogen (—H) and methyl (—CH$_3$),
m is an integer greater than zero (0),
p is an integer greater than zero (0),
the ratio m/p is 0.67-5.7 (40-85% amines) and more preferably 1.2-4 (55-80% amines).

In a preferred embodiment, R1 is hydrogen and R3 is methyl. In another preferred embodiment, R1 is hydrogen, R3 is methyl, and m/p is 1.86-3 (65%-75% amine monomers). In another preferred embodiment, R1 and R3 are each hydrogen. In another preferred embodiment, R1 and R3 are each hydrogen and m/p is 1-1.86 (50-65% amine monomers). In yet another preferred embodiment, R1 is hydrogen, Y is selected from the group consisted of ethoxyethyl, propyl, butyl and ethyl, and R is selected from the group consisting of a hydrophobic group as defined herein having 2-4 carbon atoms or an alkoxyl alkyl group, —(CH$_2$)$_l$—O—CH$_2$—CH$_3$, wherein l is 2, 3, or 4. Exemplary hydrophobic groups having 2-4 carbon atoms may be selected from the group consisting of: propyl, butyl, ethyl, and sec-butyl.

The polymers according to the present invention can be generally obtained as described herein and using methods known to the person of ordinary skill in the art of organic or medicinal chemistry. The polymers are polymerized from hydrophobic group-containing acrylate monomers and protected amine-containing acrylate monomers. Polymerization to form the polymers of the invention is preferably carried out using Reversible Addition-Fragmentation chain Transfer (RAFT) polymerization. In one embodiment, the RAFT polymerization is carried out using the RAFT reagent: 4-cyano-4(phenylcarbonothioylthio)pentanoic acid. However, other RAFT reagents are also possible, including, but no limited to those shown in FIG. 4. Polymer synthesis is performed using protected amine monomers. Deprotection of the amine yields the amine-containing polymers of formulae (I) or (Ia), wherein N is —NH$_2$.

Reversible Addition-Fragmentation chain Transfer (RAFT) polymerization is a form of controlled radical polymerization. More specifically, RAFT is a type of living polymerization involving a conventional radical polymerization in the presence of a reversible chain transfer reagent. RAFT polymerization permits synthesis of a wide range of polymers with controlled molecular weight and low polydispersity (PDI), between 1.05 and 1.6, for many monomers. Poly(acrylate)s of the invention preferably have a polydispersity less than 1.5 and more preferably less than 1.4 or 1.3. Fractionation may be used to further reduce polydispersity. RAFT polymerization is described in WO9504026, WO9801478, WO9905099, WO9931144, WO10083569, U.S. Pat. No. 6,291,620, U.S. Pat. No. 6,376,626, U.S. Pat. No. 6,642,318, and U.S. Pat. No. 6,747,111. Polymers with molecular weights greater than 20,000 and low polydisperity are also possible with RAFT polymerization and are preferred for in vivo delivery. In order for macromolecules to circulate through the blood stream effectively and to not be cleared by the kidneys, molecular weights above 30,000-50,000 are often preferred.

It is an essential feature of the unmodified amphipathic poly(acrylate) random copolymers of the invention that they are membrane active; i.e., they are capable of disrupting plasma membranes or lysosomal/endocytic membranes. Membrane activity, however, can lead to toxicity when the polymer is administered in vivo. Polyamines also interact readily with many anionic components in vivo, leading to undesired bio-distribution. Therefore, reversible inhibition of membrane activity of the polyamine is used for in vivo use. This inhibition is accomplished through reversible physiologically labile attachment of masking agents to polymer amines to form a reversibly masked membrane active poly(acrylate), i.e. herein also termed a delivery polymer. In addition to inhibiting membrane activity, the masking agents shield the polymer from non-specific interactions, reduce serum interactions, increase circulation time, or provide cell-specific interactions, i.e. targeting. The process of reversible modification also reduces positive charge to form a near neutral charge polymer. As used herein, labile means that linkage of the masking agent to the polymer is readily cleaved under conditions typically present under physiological conditions. As used herein, reversible means that cleavage of the bond linking the masking agent to the polymer results in restoration of the polymer amine to the pre-modified state, i.e. to a primary amine.

A preferred reversible physiologically labile linkage comprises: a physiologically labile covalent bond or a covalent bond cleavable under mammalian intracellular conditions. A preferred labile covalent bond comprises a pH labile bond. A preferred pH labile physiologically labile linkage comprises a maleamate. Another preferred physiologically labile linkage comprises an enzymatically cleavable linkage. A preferred enzymatically cleavable linkage is a peptide (amide) bond. A preferred peptide linkage comprises a dipeptide-amidobenzyl-carbonate as described in U.S. patent application Ser. No. 13/326,433, incorporated herein by reference.

It is an essential feature of the masking agents that, in aggregate, they inhibit membrane activity of the polymer, shield the polymer from non-specific interactions (reduce serum interactions, increase circulation time), and provide in vivo cell targeting. The membrane active poly(acrylate)s of the invention are membrane active in the unmodified (unmasked) state and not membrane active (inactivated) in the modified (masked) state. A sufficient number of masking agents are linked to the polymer to achieve the desired level of inactivation. The desired level of modification of a poly(acrylate) by attachment of masking agent(s) is readily determined using appropriate membrane activity assays. For example, if the poly(acrylate) possesses membrane activity in a given assay, a sufficient level of masking agent is linked to the polymer to achieve the desired level of inhibition of membrane activity in that assay. Masking requires modification of ≥50%, ≥60%, ≥70%, or ≥80% of the amine groups on the polymer, as determined by the quantity of amines on the polymer in the absence of any masking agents. It is also a preferred characteristic of masking agents that their attachment to the polymer reduces net charge of the polymer, thus forming a more neutral delivery polymer. It is desirable that the masked polymer retain aqueous solubility.

As used herein, a membrane active poly(acrylate) of the invention is masked if the modified polymer does not exhibit membrane activity and exhibits cell-specific (e.g., hepatocyte) targeting in vivo. A membrane active poly(acrylate) of the invention is reversibly masked if cleavage of linkages attaching the masking agents to the polymer results in restoration of amines on the poly(acrylate) thereby restoring membrane activity.

It is another essential feature that the masking agents are linked to the membrane active poly(acrylate) through reversible physiologically labile covalent bonds. By using reversible physiologically labile linkages or bonds, the masking agents can be cleaved from the polymer in vivo, thereby unmasking the polymer and restoring activity of the unmasked polymer. By choosing an appropriate reversible linkage, it is possible to form a conjugate that restores activity of the membrane active polymer after it has been delivered or targeted to a desired cell type or cellular location. Reversibility of the linkages provides for selective activation of the membrane active polymer. Suitable reversible covalent linkages contain reversible labile bonds which may be selected from the group comprising: physiologically labile bonds, cellular physiologically labile bonds, protease sensitive linkages, pH labile bonds, very pH labile bonds, and extremely pH labile bonds.

As used herein, a masking agent comprises a compound having an cell targeting group or a steric stabilizer and an amine-reactive group wherein reaction of the amine-reactive group with an amine on a poly(acrylate) results in linkage of the targeting group or steric stabilizer to the polymer via a reversible physiologically labile covalent bond. Preferably, the masking agent is charge neutral. A preferred targeting group is an Asialoglycoprotein Receptor (ASGPr) targeting group. An ASGPr targeting group is a group, typically a saccharide, having affinity for the asialoglycoprotein receptor. A preferred steric stabilizer is a polyethylene glycol (PEG). Preferred masking agents of the invention are able to modify the poly(acrylate)s of the invention (form a reversible bond with the polymer) in aqueous solution.

A preferred amine-reactive group comprises a disubstituted maleic anhydride. A preferred masking agent is represented by the structure:

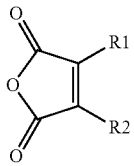

wherein $R^1$ is an alkyl group such as a methyl group ($-CH_3$), ethyl group ($-CH_2CH_3$), or propyl group ($-CH_2CH_2CH_3$), and $R^2$ comprises a neutral targeting group or a neutral steric stabilizer. More preferably, the targeting agent and steric stabilizer are uncharged.

Monosubstituted maleic anhydrides, in which R1 or R2 is a hydrogen, yield linkages which are not suitable for the described invention. While reaction of a maleic anhydride with an amine yields a β carboxyl group, this β carboxyl does not exhibit a full apparent negative charge (Rozema et al. Bioconjugate Chem. 2003, 14, 51-57). Therefore, maleic anhydride-based masking agents in which R1 and R2 are charge neutral can be used to neutralize a polyamine without imparting high negative charge.

In one embodiment, poly(acrylate) polyamines of the invention are reversibly modified by reaction with a plurality of disubstituted maleic anhydrides. The present invention therefore provides random copolymers of formulae:

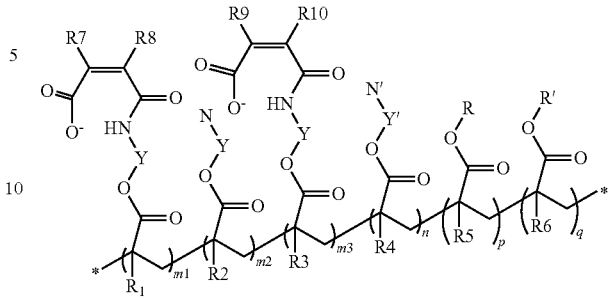

formula (II)

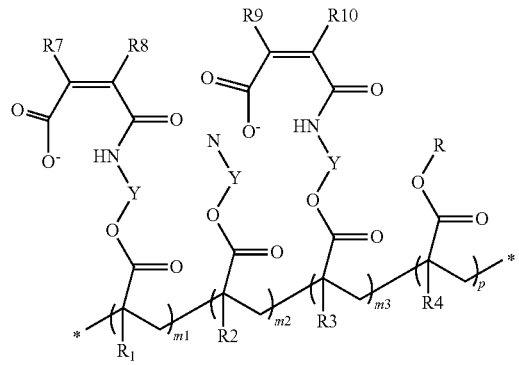

formula (IIa)

wherein N, N', Y, Y', R, R', R1, R2, R3, R4, m, n, p, q have the meanings given for formulae (I) and (Ia) above, m1 is an integer≥zero and ≤m of formula (I) or (Ia),
m3 is an integer≥zero and ≤m of formula (I) or (Ia),
m1+m2+m3=m of formulae (I) or (Ia),
m1+m3 is an integer≥m2 [i.e., ≥0.5×m of formulae (I) or (Ia) and ≤m of formula (I) or (Ia)],
R7 is an alkyl group and R8 comprises a neutral targeting group or R8 is an alkyl group and R7 comprises a neutral targeting group, and
R9 is an alkyl group and R10 comprises a neutral steric stabilizer or R10 is an alkyl group and R9 comprises a neutral steric stabilizer.

Another preferred masking agent comprises a protease sensitive dipeptide-amidobenzyl-carbonate represented by the structure:

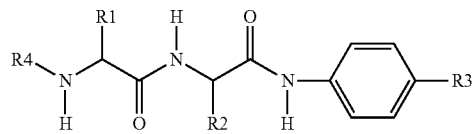

wherein R4 comprises a neutral, preferably uncharged, targeting ligand or steric stabilizer, R3 comprises an amine reactive carbonate group, and R1 and R2 are amino acid side chains. In a preferred dipeptide, R1 is a hydrophobic amino acid side chain and R2 is an uncharged hydrophilic amino acid side chain. A preferred hydrophobic amino acid is phenylalanine, valine, isoleucine, leucine, alanine, or tryptophan. A preferred uncharged hydrophilic amino acid is asparagine, glutamine, or citrulline. A more preferred hydrophobic amino acid is phenylalanine or valine. A more preferred uncharged hydrophilic amino acid is citrulline. A preferred activated carbonate is a para-nitrophenol. However, other amine reactive carbonates known in the art are readily substituted for the para-nitrophenol. Reaction of the activated carbonate with an amine connects the targeting ligand or steric stabilizer to the membrane active polyamine via a peptidase cleavable dipeptide-amidobenzyl carbamate linkage. Enzyme cleavage of the dipeptide, between the amino acid and the amidobenzyl group removes R4 from the polymer and triggers an elimination reaction which results in regeneration of the polymer amine.

Reaction of a dipeptide-amidobenzyl-carbonate masking agent with an amine of the poly(acrylate) results in reversible modification of the poly(acrylate). Hence, provided herein are conjugates comprising the amphipathic membrane active poly(acrylate)s described herein masked by modification with dipeptide-amidobenzyl-carbonate masking agents. The polymers so masked have the formula:

formula (III)

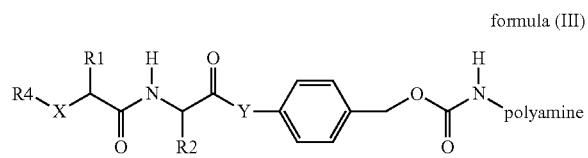

wherein:
X is —NH—, —O—, or —CH$_2$—
Y is —NH— or —O—
R1 is preferably
   —(CH$_2$)$_k$— phenyl (k is 1, 2, 3, 4, 5, 6; k=1 phenylalanine),
   —CH—(CH$_3$)$_2$ (valine),
   —CH$_2$—CH—(CH$_3$)$_2$ (leucine),
   —CH(CH$_3$)—CH$_2$—CH$_3$ (isoleucine),
   —CH$_3$ (alanine),
   —(CH$_2$)$_2$—COOH (glutamic acid),
or

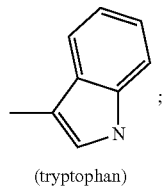

(tryptophan)

R2 is preferably
   hydrogen (glycine)
   —(CH$_2$)$_3$—NH—C(O)—NH$_2$ (citrulline),
   —(CH$_2$)$_4$—N—(CH$_3$)$_2$ (lysine(CH$_3$)$_2$),
   —(CH2)$_k$-C(O)—NH$_2$; (k is 1, 2, 3, 4, 5, 6),
   —CH$_2$—C(O)—NH$_2$ (asparagine),
   —(CH$_2$)$_2$—C(O)—NH$_2$ (glutamine),
   —CH$_2$—C(O)—NR$^1$R$^2$ (aspartic acid amide),
   —(CH$_2$)$_2$—C(O)—NR$^1$R$^2$ (glutamic acid amide),
   —CH$_2$—C(O)—OR$^1$ (aspartic acid ester), or
   —(CH$_2$)$_2$—C(O)—OR$^1$ (glutamic acid ester),
   R$^1$ and R$^2$ are alkyl groups
R$^4$ comprises a neutral polyethylene glycol or targeting ligand; and
the polyamine is an amphipathic membrane active poly (acrylate).

While the structure above indicates a single dipeptide masking agent linked to the polymer, in practice of the invention, 50% to 90% or more of polymer amines are modified by dipeptide masking agents.

The membrane active poly(acrylate)s of the invention can be conjugated to masking agents in the presence of an excess of masking agents. The excess masking agent may be removed from the conjugated delivery polymer prior to administration of the delivery polymer.

In one embodiment, the membrane active poly(acrylate) polyamine is reversibly masked by attachment of targeting group masking agents or steric stabilizer masking agents to ≥50%, ≥60%, ≥70%, or ≥80% of amines on the polyamine. In another embodiment, the membrane active polyamine is reversibly masked by attachment of a combination of targeting group masking agents and steric stabilizer masking agents to ≥50%, ≥60%, ≥70%, or ≥80% of amines on the polyamine. In another embodiment, the targeting group masking agents comprise a targeting group linked to an amine-reactive group via a PEG linker. For membrane active polyamine masking with both targeting group masking agents and steric stabilizer masking agents, a ratio of steric stabilizer to targeting group is about 0-4:1, more preferably about 0.5-2:1. In another embodiment, there are about 1.3-2 steric stabilizer masking agents to about 1 targeting group agent.

In a further embodiment of the present invention, there is provided a conjugate of the polymers of formula (I) or (Ia) covalently attached to a biologically active compound, preferably an RNA interference polynucleotide. Preferably, the polymer is covalently linked to the polynucleotide by a physiologically labile linkage. A preferred physiologically labile linkage is orthogonal to the masking agent physiologically labile linkage. A suitable physiologically labile linkage may be selected from the group comprising: physiologically labile bonds, cellular physiologically labile bonds, pH labile bonds, very pH labile bonds, extremely pH labile bonds, enzymatically cleavable bonds (including appropriate ester, amide, and phopshodiester bonds), and disulfide bonds.

We have found that by attaching the polynucleotide to the polymer via a reversible linker that is broken after the polynucleotide is delivered to the cell, it is possible to deliver a functionally active polynucleotide to a cell in vivo. The labile linker is selected such that it undergoes a chemical transformation (e.g., cleavage) when present in certain physiological conditions, (e.g., the reducing environment of the cell cytoplasm). Attachment of a polynucleotide to poly(acrylate) of the invention enhances delivery of the polynucleotide to a cell in vivo. Release of the polynucleotide from the polymer, by cleavage of the labile linkage, facilitates interaction of the polynucleotide with the appropriate cellular components for activity.

The RNAi polynucleotide-polymer conjugate is formed by linking the RNAi polynucleotide to the polymer via a physiologically labile covalent bond. The polynucleotide is synthesized or modified such that it contains a reactive group A. The polymer is also synthesized or modified such that it contains a reactive group B. Reactive groups A and B are chosen such that they can be linked via a physiologically labile covalent linkage using methods known in the art. The polymer may be linked to the 3' or the 5' end of the RNAi polynucleotide. For siRNA polynucleotides, the targeting group may be linked to either the sense strand or the antisense strand, though the sense strand is preferred.

Conjugation of the RNAi polynucleotide to a side chain primary amine of polymers (I) or (Ia) results in polymers of formula (IV) or (IVa).

formula (IV)

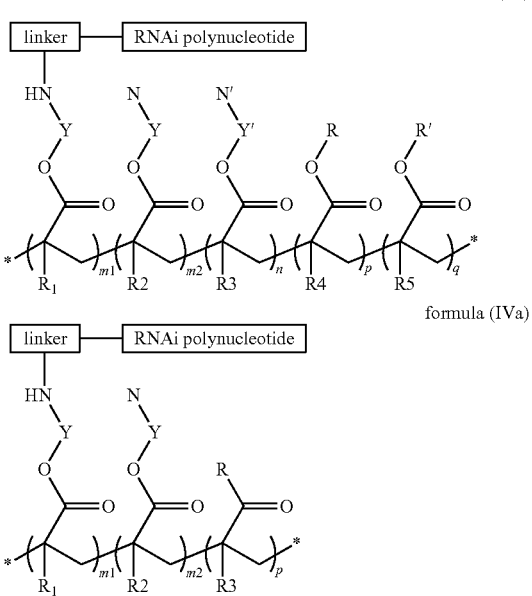

formula (IVa)

wherein N, N', Y, Y', R, R', R1, R2, R3, R4, m, n, p, q have the meanings given for formulae (I) and (Ia) above, m1 is 1, 2, 3, or 4, m1+m2=m of formula (I) or (Ia); and the linker comprises a physiologically labile linker.

In another embodiment, the RNAi polynucleotide is conjugated to a polymer backbone terminus as illustrated in formulae (V) and (Va). The polynucleotide may also be attached to the other terminus.

formula (V)

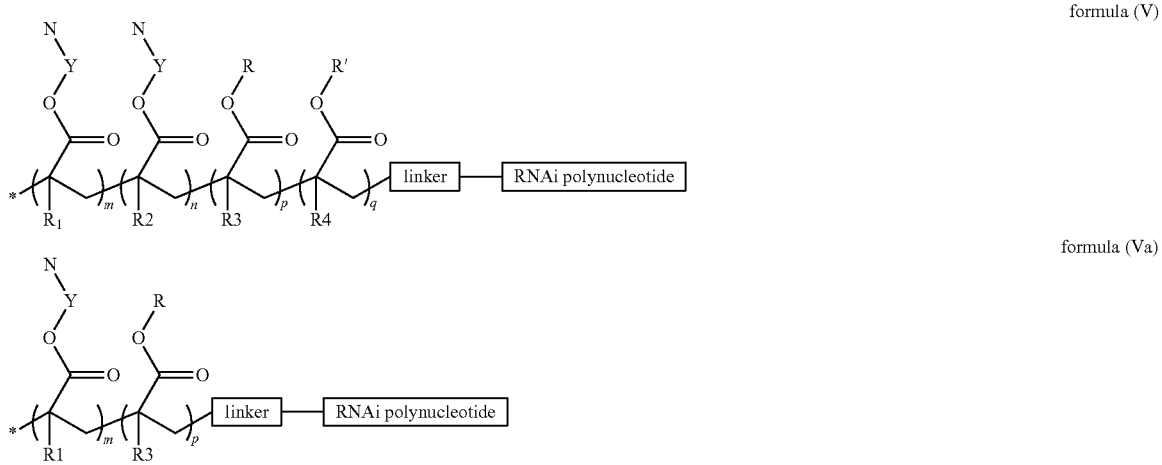

formula (Va)

wherein N, N', Y, Y', R, R', R1, R2, R3, R4, m, n, p, q have the meanings given for formulae (I) and (Ia) above, and the linker comprises a physiologically labile linker.

In a further embodiment of the present invention, there are provided conjugates of the polymers of formulae (II), (IIa), and (III) covalently attached to a biologically active compound, preferably an RNA interference polynucleotide, as shown above for the unmodified polymers. Preferably, the polymer is covalently linked to the polynucleotide by a physiologically labile linkage.

The polynucleotide can be attached to the polymer in the presence of an excess of polymer. The excess polymer may aid in formulation of the polynucleotide-polymer conjugate. The excess polymer may reduce aggregation of the conjugate during formulation of the conjugate. The polynucleotide-polymer conjugate may be separated from the excess polymer prior to administration of the conjugate to the cell or organism. Alternatively, the polynucleotide-polymer conjugate may be co-administered with the excess polymer to the cell or organism. The excess polymer may be the same as the polymer or it may be different, a helper or boost polymer.

In another embodiment, the invention features compositions for delivering RNA interference polynucleotides to a liver cells in vivo comprising: a polymer of formula (II), (IIa), or (III), and an RNA interference polynucleotide conjugated to a polynucleotide targeting group. The polynucleotide targeting group can be either a hydrophobic group containing at least 20 carbon atoms or a trivalent ASPGr targeting group as described in U.S. Patent Publication 20110207799. The reversibly modified poly(acrylate) and the siRNA-conjugate are synthesized separately and may be supplied in separate containers or a single container. The RNA interference polynucleotide is not conjugated to the polymer.

We have found that conjugation of an RNAi polynucleotide to a polynucleotide targeting group, either a hydrophobic group or to a galactose cluster, and co-administration of the RNAi polynucleotide conjugate with the modified poly(acrylate) polymers described above provides for efficient, functional delivery of the RNAi polynucleotide to liver cells, particularly hepatocytes, in vivo. By functional delivery, it is meant that the RNAi polynucleotide is delivered to the cell and has the expected biological activity, sequence-specific inhibition of gene expression. Many molecules, including polynucleotides, administered to the vasculature of a mammal are normally cleared from the body by the liver. Clearance of a polynucleotide by the liver wherein the polynucleotide is degraded or otherwise processed for removal from the body and wherein the polynucleotide does not cause sequence-specific inhibition of gene expression is not considered functional delivery.

The RNAi polynucleotide-polynucleotide targeting group conjugate is co-administered with a reversibly modified poly(acrylate) of the invention. By co-administered it is meant that the RNAi polynucleotide and the delivery polymer are administered to the mammal such that both are present in the mammal at the same time. The RNAi polynucleotide-targeting group conjugate and the delivery polymer may be administered simultaneously or they may be delivered sequentially. For simultaneous administration, they may be mixed prior to administration. For sequential administration, either the RNAi polynucleotide-targeting group conjugate or the delivery polymer may be administered first.

For RNAi polynucleotide-hydrophobic targeting group conjugates, the RNAi conjugate may be administered up to 30 minutes prior to administration of the delivery polymer. Also for RNAi polynucleotide-hydrophobic targeting group conjugates, the delivery polymer may be administered up to two hours prior to administration of the RNAi conjugate.

For RNAi polynucleotide-galactose cluster targeting group conjugates, the RNAi conjugate may be administered up to 15 minutes prior to administration of the delivery polymer. Also for RNAi polynucleotide-galactose cluster targeting group conjugates, the delivery polymer may be administered up to 15 minutes prior to administration of the RNAi conjugate.

Amphipathic

The poly(acrylate) random copolymers of the invention are amphipathic. Amphipathic, or amphiphilic, polymers and have both hydrophilic (polar, water-soluble) and hydrophobic (non-polar, lipophilic, water-insoluble) groups or parts.

As used herein, with respect to amphipathic polymers, a part is defined as a molecule derived when one covalent bond is broken and replaced by hydrogen. For example, in butyl amine, a breakage between the carbon and nitrogen bonds, and replacement with hydrogens, results in ammonia (hydrophilic) and butane (hydrophobic). If 1,4-diaminobutane is cleaved at nitrogen-carbon bonds, and replaced with hydrogens, the resulting molecules are again ammonia (2×) and butane. However, 1,4,-diaminobutane is not considered amphipathic because formation of the hydrophobic part requires breakage of two bonds.

Membrane Active

As used herein, membrane active polymers are surface active, amphipathic polymers that are able to induce one or more of the following effects upon a biological membrane: an alteration or disruption of the membrane that allows non-membrane permeable molecules to enter a cell or cross the membrane, pore formation in the membrane, fission of membranes, or disruption or dissolving of the membrane. As used herein, a membrane, or cell membrane, comprises a lipid bilayer. The alteration or disruption of the membrane can be functionally defined by the polymer's activity in at least one the following assays: red blood cell lysis (hemolysis), liposome leakage, liposome fusion, cell fusion, cell lysis, and endosomal release. Membrane active polymers that can cause lysis of cell membranes are also termed membrane lytic polymers. Polymers that preferentially cause disruption of endosomes or lysosomes over plasma membrane are considered endosomolytic. The effect of membrane active polymers on a cell membrane may be transient. Membrane active polymers possess affinity for the membrane and cause a denaturation or deformation of bilayer structures. Membrane active polymers may be synthetic or non-natural amphipathic polymers.

Delivery of a polynucleotide to a cell is mediated by the membrane active polymer disrupting or destabilizing the plasma membrane or an internal vesicle membrane (such as an endosome or lysosome), including forming a pore in the membrane, or disrupting endosomal or lysosomal vesicles thereby permitting release of the contents of the vesicle into the cell cytoplasm.

Endosomolytic

Endosomolytic polymers are polymers that, in response to a change in pH, are able to cause disruption or lysis of an endosome or provide for release of a normally cell membrane impermeable compound, such as a polynucleotide or protein, from a cellular internal membrane-enclosed vesicle, such as an endosome or lysosome. Endosomolytic polymers undergo a shift in their physico-chemical properties over a physiologically relevant pH range (usually pH 5.5-8). This shift can be a change in the polymer's solubility or ability to interact with other compounds or membranes as a result in a shift in charge, hydrophobicity, or hydrophilicity. Exemplary endosomolytic polymers have pH-labile groups or bonds. A reversibly masked membrane active poly(acrylate), wherein the masking agents are attached to the polymer via pH labile bonds, can therefore be considered to be an endosomolytic polymer.

Hydrophilic Group

Hydrophilic group indicates in qualitative terms that the chemical group is water-preferring. Typically, such chemical groups are water soluble, and are hydrogen bond donors or acceptors with water. A hydrophilic group can be charged or uncharged. Charged groups can be positively charged (anionic) or negatively charged (cationic) or both (zwitterionic). Examples of hydrophilic groups include the following chemical moieties: carbohydrates, polyoxyethylene, certain peptides, oligonucleotides, amines, amides, alkoxy amides, carboxylic acids, sulfurs, and hydroxyls.

Hydrophobic Group

Hydrophobic group indicates in qualitative terms that the chemical group is water-avoiding. Typically, such chemical groups are not water soluble, and tend not to form hydrogen bonds. Hydrophobic groups dissolve in fats, oils, lipids, and non-polar solvents and have little to no capacity to form hydrogen bonds. Hydrocarbons containing two (2) or more carbon atoms, certain substituted hydrocarbons, cholesterol, and cholesterol derivatives are examples of hydrophobic groups and compounds.

Hydrophobic groups are preferably hydrocarbons, containing only carbon and hydrogen atoms. However, non-polar substitutions or non-polar heteroatoms which maintain hydrophobicity, and include, for example fluorine, may be permitted. The term includes aliphatic groups, aromatic groups, acyl groups, alkyl groups, alkenyl groups, alkynyl groups, aryl groups, aralkyl groups, aralkenyl groups, and aralkynyl groups, each of which may be linear, branched, or cyclic. The term hydrophobic group also includes: sterols, steroids, cholesterol, and steroid and cholesterol derivatives. As used herein, lower hydrophobic monomers or groups comprise hydrophobic groups having two (2) to six (6) carbon atoms. As used herein, medium hydrophobic monomers or groups comprise hydrophobic groups having seven (7) to eleven (11) carbon atoms. As used herein, higher hydrophobic monomers or groups comprise hydrophobic groups having twelve (12) to thirty-six (36) or more carbon atoms.

Targeting Group

Targeting groups or moieties enhance the pharmacokinetic or biodistribution properties of a conjugate to which they are attached to improve cell-specific distribution and cell-specific uptake of the conjugate. Targeting groups enhance the association of molecules with a target cell. Thus, targeting groups can enhance the pharmacokinetic or biodistribution properties of a conjugate to which they are attached to improve cellular distribution and cellular uptake of the conjugate. Binding of a targeting group, such as a ligand, to a cell or cell receptor may initiate endocytosis. Targeting groups may be monovalent, divalent, trivalent, tetravalent, or have higher valency. Targeting groups may be selected from the group comprising: compounds with affinity to cell surface molecule, cell receptor ligands, and antibodies, antibody fragments, and antibody mimics with affinity to cell surface molecules. A preferred targeting group comprises a cell receptor ligand. A variety of ligands have been used to target drugs and genes to cells and to specific cellular receptors. Cell receptor ligands may be selected from the group comprising: carbohydrates, glycans, saccharides (including, but not limited to: galactose, galactose derivatives, mannose, and mannose derivatives), vitamins, folate, biotin, aptamers, and peptides (including, but not limited to: RGD-containing peptides, insulin, EGF, and transferrin).

ASGPr Targeting Group

Galactose and galactose derivates have been used to target molecules to hepatocytes in vivo through their binding to the asialoglycoprotein receptor (ASGPr) expressed on the surface of hepatocytes. As used herein, an ASGPr targeting group comprises a galactose and galactose derivative (structural analog) having affinity for the ASGPr equal to or greater than that of galactose. Binding of galactose targeting moieties to the ASGPr(s) facilitates cell-specific targeting of the delivery polymer to hepatocytes and endocytosis of the delivery polymer into hepatocytes.

ASGPr targeting moieties may be selected from the group comprising: lactose, galactose, N-acetylgalactosamine (GalNAc), galactosamine, N-formylgalactosamine, N-acetyl-galactosamine, N-propionylgalactosamine, N-n-butanoylgalactosamine, N-iso-butanoyl-galactosamine, oligosaccharides, saccharide clusters (such as: Tyr-Glu-Glu-(aminohexyl GalNAc)$_3$, lysine-based galactose clusters, and cholane-based galactose clusters) (Iobst, S. T. and Drickamer, K. *J.B.C.* 1996, 271, 6686). ASGPr targeting moieties can be monomeric (e.g., having a single galactosamine) or multimeric (e.g., having multiple galactosamines). Further suitable conjugates can include oligosaccharides that can bind to carbohydrate recognition domains (CRD) found on the asialoglycoprotein-receptor (ASGP-R). Example conjugate moieties containing oligosaccharides and/or carbohydrate complexes are provided in U.S. Pat. No. 6,525,031.

In some embodiments, an ASGPr targeting group is linked to an amine-reactive group, such as a maleic anhydride, through a PEG linker as illustrated by the structure:

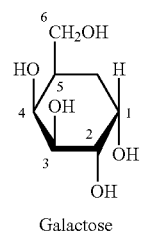

wherein n is an integer between 1 and 19 (inclusive).

In one embodiment, an ASGPr targeting group comprises a galactose cluster (galactose cluster targeting group). As used herein, a galactose cluster comprises a molecule having two to four terminal galactose derivatives. A terminal galactose derivative is attached to a molecule through its C-1 carbon. A preferred galactose cluster has three terminal galactosamines or galactosamine derivatives each having affinity for the asialoglycoprotein receptor. A more preferred galactose cluster has three terminal N-acetyl-galactosamines. Other terms common in the art include tri-antennary galactose, tri-valent galactose and galactose trimer. It is known that tri-antennary galactose derivative clusters are bound to the ASGPr with greater affinity than bi-antennary or mono-antennary galactose derivative structures (Baenziger and Fiete, 1980, Cell, 22, 611-620; Connolly et al., 1982, J. Biol. Chem., 257, 939-945).

Galactose

A galactose cluster contains three galactose derivatives each linked to a central branch point. The galactose derivatives are attached to the central branch point through the C-1 carbons of the saccharides. The galactose derivative is preferably linked to the branch point via linkers or spacers. A preferred spacer is a flexible hydrophilic spacer (U.S. Pat. No. 5,885,968; Biessen et al. J. Med. Chem. 1995 Vol. 39 p. 1538-1546). A preferred flexible hydrophilic spacer is a PEG spacer. A preferred PEG spacer is a PEG$_3$ spacer. The branch point can be any small molecule which permits attachment of the three galactose derivatives and further permits attachment of the branch point to the RNAi polynucleotide. An exemplary branch point group is a di-lysine. A di-lysine molecule contains three amine groups through which three galactose derivatives may be attached and a carboxyl reactive group through which the di-lysine may be attached to the RNAi polynucleotide.

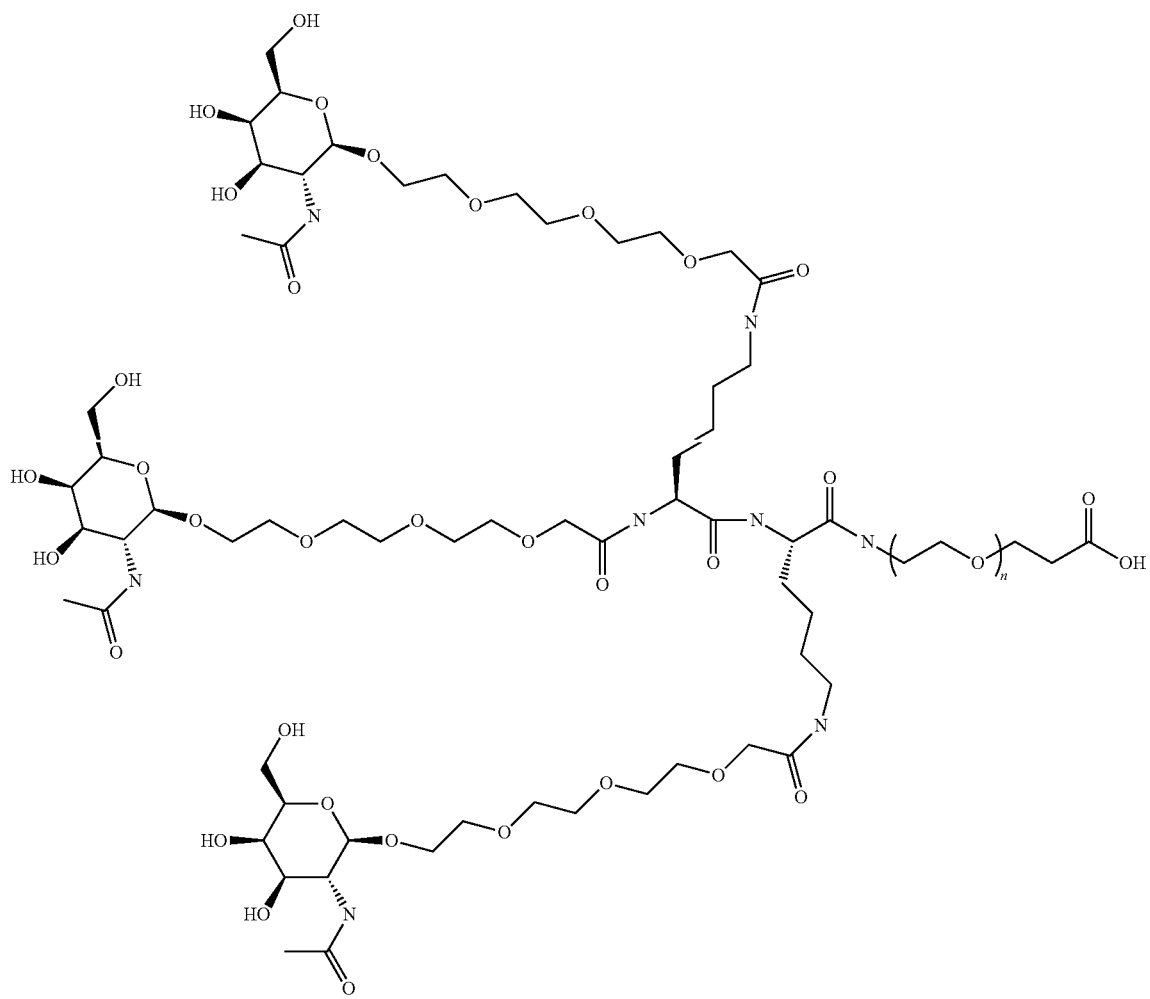

Galactose Cluster with PEG Spacer Between Branch Point and Nucleic Acid

Steric Stabilizer

As used herein, a steric stabilizer is a non-ionic hydrophilic polymer (either natural, synthetic, or non-natural) that prevents or inhibits intramolecular or intermolecular interactions of a polymer to which it is attached relative to the polymer containing no steric stabilizer. A steric stabilizer hinders a polymer to which it is attached from engaging in electrostatic interactions. Electrostatic interaction is the non-covalent association of two or more substances due to attractive forces between positive and negative charges. Steric stabilizers can inhibit interaction with blood components and therefore opsonization, phagocytosis, and uptake by the reticuloendothelial system. Steric stabilizers can thus increase circulation time of molecules to which they are attached. Steric stabilizers can also inhibit aggregation of a polymer. A preferred steric stabilizer is a polyethylene glycol (PEG) or PEG derivative. As used herein, a preferred PEG can have about 1-500 ethylene glycol monomers, 2-20 ethylene glycol monomers, 5-15 ethylene glycol monomers, or about 10 ethylene glycol monomers. As used herein, a preferred PEG can also have a molecular weight average of about 85-20,000 Daltons (Da), about 200-1000 Da, about 200-750 Da, or about 550 Da. As used herein, steric stabilizers prevent or inhibit intramolecular or intermolecular interactions of a polymer to which it is attached relative to the polymer containing no steric stabilizer in aqueous solution.

A structural analog is a compound having a structure similar to that of another one, but differing from it in respect of a certain component. It can differ in one or more atoms, functional groups, or substructures, which are replaced with other atoms, groups, or substructures. Typically, a structural analog differs in the replacement of a single element, i.e. replacement of one atom or functional group by another atom of a different element or functional group. A structural analog can be imagined to be formed, at least theoretically, from the other compound. As such, a structural analog has a high chemical similarity to the other compound. As typically used in the art, despite structural similarity, structural analogs may have very different physical, chemical, or biochemical properties. However, as used herein with respect to their stated properties, structural analogs have similar physical, chemical, or biochemical properties.

Surface Charge

Zeta potential is a physical property which is exhibited by a particle in suspension and is closely related to surface charge. In aqueous media, the pH of the sample is one of the most important factors that affects zeta potential. When charge is based upon protonation/deprotonation of bases/acids, the charge is dependent on pH. Therefore, a zeta potential value must include the solution conditions, especially pH, to be meaningful. For typical particles, the magnitude of the zeta potential gives an indication of the potential stability of the colloidal system. If all the particles in suspension have a large negative or positive zeta potential, they will tend to repel each other and there will be no tendency for the particles to come together. However, if the particles have low zeta potential values, there will be no force to prevent the particles coming together and flocculating. The general dividing line between stable and unstable suspensions for typical particles is generally taken at either +30 or −30 mV. Particles with zeta potentials more positive than +30 mV or more negative than −30 mV are normally considered stable. Delivery polymers of the described invention exhibit a zeta potential of 20 mV to −20 mV at physiological salt and pH 8, but are colloidally stable in aqueous solution and do not flocculate.

Positive charge, or zeta potential, of a membrane active polyamine is reduced by modification with the masking agents. Polymer charge, especially positive charge, can result in unwanted interactions with serum components or non-target cells. Positive surface charge also plays a role in membrane activity by enhancing interaction of the polymer with negatively charged cell membranes. Therefore, in vivo siRNA delivery vehicles with near neutral net charge or zeta potential are preferred. Delivery polymers of the invention, membrane active polyamines modified by reversible attachment of ASGPr targeting group masking agents and steric stabilizer masking agents, have an apparent surface charge near neutral and are serum stable. More specifically, the delivery polymers of the invention have a zeta potential, measured at pH 8, between +30 and −30 mV, between +20 and −20 mV, between +10 and −10 mV, or between +5 and −5 mV. At pH 7, the net charge of the conjugate is expected to be more positive than at pH 8. Net charge, or surface charge, is a significant factor for in vivo applications.

Labile Linkage

A linkage or linker is a connection between two atoms that links one chemical group or segment of interest to another chemical group or segment of interest via one or more covalent bonds. For example, a linkage can connect a modifying or masking agent to a polymer. Formation of a linkage may connect two separate molecules into a single molecule or it may connect two atoms in the same molecule. The linkage may be charge neutral or may bear a positive or negative charge. A reversible or labile linkage contains a reversible or labile bond. A linkage may optionally include a spacer that increases the distance between the two joined atoms. A spacer may further add flexibility and/or length to the linkage. Spacers may include, but are not be limited to, alkyl groups, alkenyl groups, alkynyl groups, aryl groups, aralkyl groups, aralkenyl groups, aralkynyl groups; each of which can contain one or more heteroatoms, heterocycles, amino acids, nucleotides, and saccharides. Spacer groups are well known in the art and the preceding list is not meant to limit the scope of the invention.

A reversible or labile bond is a covalent bond other than a covalent bond to a hydrogen atom that is capable of being selectively broken or cleaved under conditions that will not break or cleave other covalent bonds in the same molecule. More specifically, a reversible or labile bond is a covalent bond that is less stable (thermodynamically) or more rapidly broken (kinetically) under appropriate conditions than other non-labile covalent bonds in the same molecule. Cleavage of a labile bond within a molecule may result in the formation of two molecules. For those skilled in the art, cleavage or lability of a bond is generally discussed in terms of half-life ($t_{1/2}$) of bond cleavage (the time required for half of the bonds to cleave). Thus, reversible or labile bonds encompass bonds that can be selectively cleaved more rapidly than other bonds in a molecule.

Appropriate conditions are determined by the type of labile bond and are well known in organic chemistry. A labile bond can be sensitive to pH, oxidative or reductive conditions or agents, temperature, salt concentration, the presence of an enzyme (such as esterases, including nucleases, and proteases), or the presence of an added agent. For example, increased or decreased pH is the appropriate conditions for a pH-labile bond.

The rate at which a labile group will undergo transformation can be controlled by altering the chemical constituents of the molecule containing the labile group. For example, addition of particular chemical moieties (e.g., electron acceptors or donors) near the labile group can affect the particular conditions (e.g., pH) under which chemical transformation will occur.

As used herein, a physiologically labile bond is a labile bond that is cleavable under conditions normally encountered or analogous to those encountered within a mammalian body. Physiologically labile linkage groups are selected such that they undergo a chemical transformation (e.g., cleavage) when present in certain physiological conditions.

As used herein, a cellular physiologically labile bond is a labile bond that is cleavable under mammalian intracellular conditions. Mammalian intracellular conditions include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from proteolytic or hydrolytic enzymes. Physiologically labile bonds that are cleaved under appropriate conditions with a half-life of less than 45 min. are considered very labile. Physiologically labile bonds that are cleaved under appropriate conditions with a half-life of less than 15 min are considered extremely labile.

Chemical transformation (cleavage of the labile bond) occurs when a molecule containing the labile bond reaches an appropriate intra- and/or extra-cellular environment. For example, a pH labile bond may be cleaved when the molecule enters an acidified endosome. Thus, a pH labile bond may be considered to be an endosomal cleavable bond. Enzyme cleavable bonds may be cleaved when exposed to enzymes such as those present in an endosome or lysosome or in the cytoplasm. A disulfide bond may be cleaved when the molecule enters the more reducing environment of the cell cytoplasm. Thus, a disulfide may be considered to be a cytoplasmic cleavable bond.

As used herein, a pH-labile bond is a labile bond that is selectively broken under acidic conditions (pH<7). Such bonds may also be termed endosomally labile bonds, since cell endosomes and lysosomes have a pH less than 7. The term pH-labile includes bonds that are pH-labile, very pH-labile, and extremely pH-labile.

Reaction of an amine with a cyclic anhydride to form an amide acid.

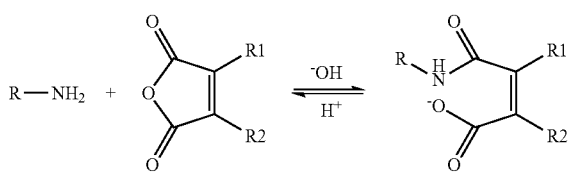

Cleavage of the amide acid to form an amine and an anhydride is pH-dependent and is greatly accelerated at acidic pH. This pH-dependent reactivity can be exploited to form reversible pH-labile bonds and linkers.

Very pH-labile bond: A very pH-labile bond has a half-life for cleavage at pH 5 of less than 45 min. The construction of very pH-labile bonds is well-known in the chemical art.

Extremely pH-labile bonds: An extremely pH-labile bond has a half-life for cleavage at pH 5 of less than 15 min. The construction of extremely pH-labile bonds is well-known in the chemical art.

Disubstituted cyclic anhydrides are particularly useful for modification or attachment of masking agents to membrane active poly(acrylate) polymers of the invention. They provide physiologically pH-labile linkages, readily modify amines, and restore those amines upon cleavage in the reduced pH found in cellular endosomes and lysosome. Second, the α or β carboxylic acid group created upon reaction with an amine, appears to contribute only about $\frac{1}{20}^{th}$ of the expected negative charge to the polymer (Rozema et al. Bioconjugate Chemistry 2003). Thus, modification of the polyamine with the disubstituted maleic anhydrides effectively neutralizes the positive charge of the polyamine rather than creates a polymer with high negative charge. Near neutral polymers are preferred for in vivo delivery.

RNAi Polynucleotide-Polynucleotide Targeting Group Conjugate

The RNAi polynucleotide-polynucleotide targeting group conjugate is formed by covalently linking the RNAi polynucleotide to the polynucleotide targeting group. The polynucleotide is synthesized or modified such that it contains a reactive group A. The polynucleotide targeting group is also synthesized or modified such that it contains a reactive group B. Reactive groups A and B are chosen such that they can be linked via a covalent linkage using methods known in the art.

The polynucleotide targeting group may be linked to the 3' or the 5' end of the RNAi polynucleotide. For siRNA polynucleotides, the targeting group may be linked to either the sense strand or the antisense strand, though the sense strand is preferred.

In one embodiment, the polynucleotide targeting group consists of a hydrophobic group. More specifically, the polynucleotide targeting group consists of a hydrophobic group having at least 20 carbon atoms. Hydrophobic groups used as polynucleotide targeting moieties are herein referred to as hydrophobic targeting moieties. Exemplary suitable hydrophobic groups may be selected from the group comprising: cholesterol, dicholesterol, tocopherol, ditocopherol, didecyl, didodecyl, dioctadecyl, didodecyl, dioctadecyl, isoprenoid, and choleamide.

The hydrophobic targeting group may be attached to the 3' or 5' end of the RNAi polynucleotide using methods known in the art. For RNAi polynucleotides having two strands, such as siRNA, the hydrophobic group may be attached to either strand.

The galactose cluster may be attached to the 3' or 5' end of the RNAi polynucleotide using methods known in the art. For RNAi polynucleotides having two strands, such as siRNA, the galactose cluster may be attached to either strand.

Polynucleotide

The term polynucleotide, or nucleic acid or polynucleic acid, is a term of the art that refers to a polymer containing at least two nucleotides. Nucleotides are the monomeric units of polynucleotide polymers. Polynucleotides with less than 120 monomeric units are often called oligonucleotides. Natural nucleic acids have a deoxyribose- or ribose-phosphate backbone. A non-natural or synthetic polynucleotide is a polynucleotide that is polymerized in vitro or in a cell free system and contains the same or similar bases but may contain a backbone of a type other than the natural ribose or deoxyribose-phosphate backbone. Polynucleotides can be synthesized using any known technique in the art. Polynucleotide backbones known in the art include: PNAs (peptide nucleic acids), phosphorothioates, phosphorodiamidates, morpholinos, and other variants of the phosphate backbone of native nucleic acids. Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups on the nucleotide such as, but not limited to, amines, alcohols, thiols, carboxylates, and alkylhalides. The term base encompasses any of the known base analogs of DNA and RNA. A polynucleotide may contain ribonucleotides, deoxyribonucleotides, synthetic nucleotides, or any suitable combination. Polynucleotides may be polymerized in vitro, they may be recombinant, contain chimeric sequences, or derivatives of these groups. A polynucleotide may include a terminal cap group at the 5'-end, the 3'-end, or both the 5' and 3' ends. The cap group can be, but is not limited to, an inverted deoxy abasic group, an inverted deoxy thymidine group, a thymidine group, or 3' glyceryl modification.

An RNA interference (RNAi) polynucleotide is a molecule capable of inducing RNA interference through interaction with the RNA interference pathway machinery of mammalian cells to degrade or inhibit translation of messenger RNA (mRNA) transcripts of a transgene in a sequence specific manner. Two primary RNAi polynucleotides are small (or short) interfering RNAs (siRNAs) and micro RNAs (miRNAs). RNAi polynucleotides may be selected from the group comprising: siRNA, miRNA, double-strand RNA (dsRNA), short hairpin RNA (shRNA), and expression cassettes encoding RNA capable of inducing RNA interference. siRNA comprises a double stranded structure typically containing 15-50 base pairs and preferably 21-25 base pairs and having a nucleotide sequence identical (perfectly complementary) or nearly identical (partially complementary) to a coding sequence in an expressed target gene or RNA within the cell. An siRNA may have dinucleotide 3' overhangs. An siRNA may be composed of two annealed polynucleotides or a single polynucleotide that forms a hairpin structure. An siRNA molecule of the invention comprises a sense region and an antisense region. In one embodiment, the siRNA of the conjugate is assembled from two oligonucleotide fragments wherein one fragment comprises the nucleotide sequence of the antisense strand of the siRNA molecule and a second fragment comprises nucleotide sequence of the sense region of the siRNA molecule. In another embodiment, the sense strand is connected to the antisense strand via a linker molecule, such as a polynucleotide linker or a non-nucleotide linker. MicroRNAs (miRNAs) are small noncoding RNA gene products about 22 nucleotides long that direct destruction or translational repression of their mRNA targets. If the complementarity between the miRNA and the target mRNA is partial, translation of the target mRNA is repressed. If complementarity is extensive, the target mRNA is cleaved. For miRNAs, the complex binds to target sites usually located in the 3' UTR of mRNAs that typically share only partial homology with the miRNA. A "seed region"—a stretch of about seven (7) consecutive nucleotides on the 5' end of the miRNA that forms perfect base pairing with its target—plays a key role in miRNA specificity. Binding of the RISC/miRNA complex to the mRNA can lead to either the repression of protein translation or cleavage and degradation of the mRNA. Recent data indicate that mRNA cleavage happens preferentially if there is perfect homology along the whole length of the miRNA and its target instead of showing perfect base-pairing only in the seed region (Pillai et al. 2007).

RNAi polynucleotide expression cassettes can be transcribed in the cell to produce small hairpin RNAs that can function as siRNA, separate sense and anti-sense strand linear siRNAs, or miRNA. RNA polymerase III transcribed DNAs contain promoters selected from the list comprising: U6 promoters, H1 promoters, and tRNA promoters. RNA polymerase II promoters include U1, U2, U4, and U5 promoters, snRNA promoters, microRNA promoters, and mRNA promoters.

Lists of known miRNA sequences can be found in databases maintained by research organizations such as Wellcome Trust Sanger Institute, Penn Center for Bioinformatics, Memorial Sloan Kettering Cancer Center, and European Molecule Biology Laboratory, among others. Known effective siRNA sequences and cognate binding sites are also well represented in the relevant literature. RNAi molecules are readily designed and produced by technologies known in the art. In addition, there are computational tools that increase the chance of finding effective and specific sequence motifs (Pei et al. 2006, Reynolds et al. 2004, Khvorova et al. 2003, Schwarz et al. 2003, Ui-Tei et al. 2004, Heale et al. 2005, Chalk et al. 2004, Amarzguioui et al. 2004).

The polynucleotides of the invention can be chemically modified. Non-limiting examples of such chemical modifications include: phosphorothioate internucleotide linkages, 2'-O-methyl ribonucleotides, 2'-deoxy-2'-fluoro ribonucleotides, 2'-deoxy ribonucleotides, "universal base" nucleotides, 5-C-methyl nucleotides, and inverted deoxyabasic residue incorporation. These chemical modifications, when used in various polynucleotide constructs, are shown to preserve polynucleotide activity in cells while at the same time increasing the serum stability of these compounds. Chemically modified siRNA can also minimize the possibility of activating interferon activity in humans.

In one embodiment, a chemically-modified RNAi polynucleotide of the invention comprises a duplex having two strands, one or both of which can be chemically-modified, wherein each strand is about 19 to about 29 nucleotides. In one embodiment, an RNAi polynucleotide of the invention comprises one or more modified nucleotides while maintaining the ability to mediate RNAi inside a cell or reconstituted in vitro system. An RNAi polynucleotide can be modified wherein the chemical modification comprises one or more (e.g., about 1, 2, 3, 4, 5, 6, 7, 8, 9, 10, or more) of the nucleotides. An RNAi polynucleotide of the invention can comprise modified nucleotides as a percentage of the total number of nucleotides present in the RNAi polynucleotide. As such, an RNAi polynucleotide of the invention can generally comprise modified nucleotides from about 5 to about 100% of the nucleotide positions (e.g., 5%, 10%, 15%, 20%, 25%, 30%, 35%, 40%, 45%, 50%, 55%, 60%, 65%, 70%, 75%, 80%, 85%, 90%, 95% or 100% of the nucleotide positions). The actual percentage of modified nucleotides present in a given RNAi polynucleotide depends on the total number of nucleotides present in the RNAi polynucleotide. If the RNAi polynucleotide is single stranded, the percent modification can be based upon the total number of nucleotides present in the single stranded RNAi polynucleotide. Likewise, if the RNAi polynucleotide is double stranded, the percent modification can be based upon the total number of nucleotides present in the sense strand, antisense strand, or both the sense and antisense strands. In addition, the actual percentage of modified nucleotides present in a given RNAi polynucleotide can also depend on the total number of purine and pyrimidine nucleotides present in the RNAi polynucleotide. For example, wherein all pyrimidine nucleotides and/or all purine nucleotides present in the RNAi polynucleotide are modified.

An RNAi polynucleotide modulates expression of RNA encoded by a gene. Because multiple genes can share some degree of sequence homology with each other, an RNAi polynucleotide can be designed to target a class of genes with sufficient sequence homology. Thus, an RNAi polynucleotide can contain a sequence that has complementarity to sequences that are shared amongst different gene targets or are unique for a specific gene target. Therefore, the RNAi polynucleotide can be designed to target conserved regions of an RNA sequence having homology between several genes thereby targeting several genes in a gene family (e.g., different gene isoforms, splice variants, mutant genes, etc.). In another embodiment, the RNAi polynucleotide can be designed to target a sequence that is unique to a specific RNA sequence of a single gene.

The term complementarity refers to the ability of a polynucleotide to form hydrogen bonds with another polynucleotide sequence by either traditional Watson-Crick or other non-traditional types. In reference to the polynucleotide molecules of the present invention, the binding free energy for a polynucleotide molecule with its target (effector binding site) or complementary sequence is sufficient to allow the relevant function of the polynucleotide to proceed, e.g., enzymatic mRNA cleavage or translation inhibition. Determination of binding free energies for nucleic acid molecules is well known in the art (Frier et al. 1986, Turner et al. 1987). A percent complementarity indicates the percentage of bases, in a contiguous strand, in a first polynucleotide molecule which can form hydrogen bonds (e.g., Watson-Crick base pairing) with a second polynucleotide sequence (e.g., 5, 6, 7, 8, 9, 10 out of 10 being 50%, 60%, 70%, 80%, 90%, and 100% complementary). Perfectly complementary means that all the bases in a contiguous strand of a polynucleotide sequence will hydrogen bond with the same number of contiguous bases in a second polynucleotide sequence.

By inhibit, down-regulate, or knockdown gene expression, it is meant that the expression of the gene, as measured by the level of RNA transcribed from the gene or the level of polypeptide, protein, or protein subunit translated from the RNA, is reduced below that observed in the absence of the blocking polynucleotide-conjugates of the invention. Inhibition, down-regulation, or knockdown of gene expression, with a polynucleotide delivered by the compositions of the invention, is preferably below that level observed in the presence of a control inactive nucleic acid, a nucleic acid with scrambled sequence or with inactivating mismatches, or in absence of conjugation of the polynucleotide to the masked polymer.

In Vivo Administration

In pharmacology and toxicology, a route of administration is the path by which a drug, fluid, poison, or other substance is brought into contact with the body. In general, methods of administering drugs and nucleic acids for treatment of a mammal are well known in the art and can be applied to administration of the compositions of the invention. The compounds of the present invention can be administered via any suitable route, most preferably parenterally, in a preparation appropriately tailored to that route. Thus, the compounds of the present invention can be administered by injection, for example, intravenously, intramuscularly, intracutaneously, subcutaneously, or intraperitoneally. Accordingly, the present invention also provides pharmaceutical compositions comprising a pharmaceutically acceptable carrier or excipient.

Parenteral routes of administration include intravascular (intravenous, intraarterial), intramuscular, intraparenchymal, intradermal, subdermal, subcutaneous, intratumor, intraperitoneal, intrathecal, subdural, epidural, and intralymphatic injections that use a syringe and a needle or catheter. Intravascular herein means within a tubular structure called a vessel that is connected to a tissue or organ within the body. Within the cavity of the tubular structure, a bodily fluid flows to or from the body part. Examples of bodily fluid include blood, cerebrospinal fluid (CSF), lymphatic fluid, or bile. Examples of vessels include arteries, arterioles, capillaries, venules, sinusoids, veins, lymphatics, bile ducts, and ducts of the salivary or other exocrine glands. The intravascular route includes delivery through the blood vessels such as an artery or a vein. The blood circulatory system provides systemic spread of the pharmaceutical.

The described compositions are injected in pharmaceutically acceptable carrier solutions. Pharmaceutically acceptable refers to those properties and/or substances which are acceptable to the mammal from a pharmacological/toxicological point of view. The phrase pharmaceutically acceptable refers to molecular entities, compositions, and properties that are physiologically tolerable and do not typically produce an allergic or other untoward or toxic reaction when administered to a mammal. Preferably, as used herein, the term pharmaceutically acceptable means approved by a regulatory agency of the Federal or a state government or listed in the U.S. Pharmacopeia or other generally recognized pharmacopeia for use in animals and more particularly in humans.

Therapeutic Effect

RNAi polynucleotides may be delivered for research purposes or to produce a change in a cell that is therapeutic. In vivo delivery of RNAi polynucleotides is useful for research reagents and for a variety of therapeutic, diagnostic, target validation, genomic discovery, genetic engineering, and pharmacogenomic applications. We have disclosed RNAi polynucleotide delivery resulting in inhibition of endogenous gene expression in hepatocytes. Levels of a reporter (marker) gene expression measured following delivery of a polynucleotide indicate a reasonable expectation of similar levels of gene expression following delivery of other polynucleotides. Levels of treatment considered beneficial by a person having ordinary skill in the art differ from disease to disease. For example, Hemophilia A and B are caused by deficiencies of the X-linked clotting factors VIII and IX, respectively. Their clinical course is greatly influenced by the percentage of normal serum levels of factor VIII or IX: <2%, severe; 2-5%, moderate; and 5-30% mild. Thus, an increase from 1% to 2% of the normal level of circulating factor in severe patients can be considered beneficial. Levels greater than 6% prevent spontaneous bleeds but not those secondary to surgery or injury. Similarly, inhibition of a gene need not be 100% to provide a therapeutic benefit. A person having ordinary skill in the art of gene therapy would reasonably anticipate beneficial levels of expression of a gene specific for a disease based upon sufficient levels of marker gene results. In the hemophilia example, if marker genes were expressed to yield a protein at a level comparable in volume to 2% of the normal level of factor VIII, it can be reasonably expected that the gene coding for factor VIII would also be expressed at similar levels. Thus, reporter or marker genes serve as useful paradigms for expression of intracellular proteins in general.

The liver is an important target tissue for RNAi therapy given its central role in metabolism (e.g., lipoprotein metabolism in various hypercholesterolemias) and the secretion of circulating proteins (e.g., clotting factors in hemophilia). In addition, acquired disorders such as chronic hepatitis and cirrhosis are common and are also potentially treated by RNAi therapies. A number of diseases or conditions which affect or are affected by the liver are potentially treated through knockdown (inhibition) of gene expression in the liver. Such liver diseases and conditions may be selected from the list comprising: liver cancers (including hepatocellular carcinoma, HCC), viral infections (including hepatitis), metabolic disorders, (including hyperlipidemia and diabetes), fibrosis, and acute liver injury.

The amount (dose) of delivery polymer and RNAi-polynucleotide-conjugate that is to be administered can be determined through routine experimentation. We have shown effective knockdown of gene expression using 0.05-20 mg/kg animal weight of siRNA-conjugate and 1-60 mg/kg animal weight delivery polymer. A preferred amount in mice is 0.25-2.5 mg/kg siRNA-conjugate and 1-40 mg/kg delivery polymer. More preferably, about 2-10 mg/kg delivery polymer is administered. A preferred amount in rats 0.25-16 mg/kg delivery polymer.

As used herein, in vivo means that which takes place inside an organism and more specifically to a process performed in or on the living tissue of a whole, living multicellular organism (animal), such as a mammal, as opposed to a partial or dead one.

Transfection Reagent

The poly(acrylate)s described herein may be used as in vitro transfection reagents. The process of delivering a polynucleotide to a cell in vitro has been commonly termed transfection or the process of transfecting. The term transfecting as used herein refers to the introduction of a polynucleotide from outside a cell to inside the cell such the polynucleotide has biological activity. The polynucleotide may be used for research purposes or to produce a change in a cell that can be therapeutic. The delivery of a polynucleotide can lead to modification of the genetic material present in the target cell.

An in vitro transfection reagent is a compound or composition of compounds that binds to or complexes with oligonucleotides or polynucleotides and mediates their entry into a cell, typically a mammalian cell in vitro. Examples of in vitro transfection reagents include, but are not limited to, protein and polymer complexes (polyplexes), lipids and liposomes (lipoplexes), combinations of polymers and lipids (lipopolyplexes), calcium phosphate precipitates, and dendrimers.

Typically, the in vitro transfection reagent has a component with a net positive charge which associates or complexes with, via electrostatic interaction, the negative charge of the oligonucleotide or polynucleotide. Cationic in vitro transfection agents may also condense large nucleic acids. In addition to their utility for in vivo delivery, the poly(acrylate)s described herein can also be used as in vitro transfection reagents. For use as in vitro transfection reagents, the poly (acrylate)s may be masked or unmasked.

EXAMPLES

Example 1

Amphipathic Poly(Acrylate) Random Copolymer Synthesis—General RAFT Procedure

A. Reversible Addition-Fragmentation Chain Transfer (RAFT) Polymerization were performed to synthesize a series of random (meth)acrylate copolymers. RAFT polymerizations are described in Shipp D A and Malepu V "RAFT Polymerization of Vinyl Acetate, Styrene and Acrylates Using N,N Dithiocarbamates," In *Controlled/Living Radical Polymerization: Progress in RAFT, DT, NMP, and OMRP*; Matyjaszewski, K.; ACS Symposium Series 1024; American Chemical Society: Washington, D.C., 2009; pp 37-47].

B. Polymer Calculations: Polymer Theoretical Molecular Weight ($M_{n,\,th}$), Moles Monomers, Moles Chain Transfer Agent, Moles Initiator.

General reaction for synthesis of polymer P from monomers A and B $$A + B \xrightarrow{C, I} P$$

A=Hydrophilic Monomer
B=Hydrophobic Monomer
P=Polymer
C=Chain Transfer Agent (CTA)
I=Initiator Calculation of monomer average molecular weight for polymer P

[% $A \times MW_A$]+[% $B \times MW_B$]=$\overline{MW}_{AB}$

% A=percent hydrophilic monomers A in polymer P
% B=percent hydrophobic monomers B in polymer P
$MW_A$=Molecular weight of hydrophilic monomer A
$MW_B$=Molecular weight of hydrophobic monomer B
$\overline{MW}_{AB}$=Average molecular weight of polymer monomer Calculation of number of monomers in polymer P having a desired (theoretical) molecular weight $M_{n,\,th}$ ($M_n$ in the equation below):

$M_n / \overline{MW}_{AB} = n_{AB}$ $n_{AB}$=number of monomers in polymer P having theoretical molecular weight $M_{n,\,th}$ Calculation of moles of monomers A and B in x grams polymer P having theoretical molecular weight $M_{n,\,th}$:

$$\left[\% \, A \times n_{AB} \times \left(\frac{x}{M_n}\right)\right] = moles_A$$

$$\left[\% \, B \times n_{AB} \times \left(\frac{x}{M_n}\right)\right] = moles_B$$

$moles_A$=moles hydrophilic monomer A
$moles_B$=moles hydrophobic monomer B

Calculation of moles Chain Transfer Agent (CTA) for synthesis of x grams polymer P having theoretical molecular weight $M_n$:

$$\frac{moles_A}{[n_{AB} \times \% \, A]} = \frac{moles_B}{[n_{AB} \times \% \, B]} = moles_C$$

$moles_C$=moles Chain Transfer Agent

Calculation of moles Initiator for synthesis of x grams polymer P having theoretical molecular weight $M_{n,\,th}$:

% $I \times moles_C = moles_I$ $moles_I$=moles Initiator

C. General Procedure for RAFT Polymerization of Protected Amine Acrylate Random Copolymers.

Solutions of CTA and Initiator are prepared in Butyl Acetate. Hydrophilic monomer, hydrophobic monomer, CTA solution, Initiator solution, and Butyl Acetate are added to a vial and the mixture is degassed for 1 hour by $N_2$ bubbling. The vial is sealed and stirred at 80° C. overnight. After ~16 hours, the reaction vessel is removed from heat and the solution is allowed to cool to RT. The resulting polymer was precipitated by addition of hexane (~8× vol.). After centrifugation, the solution is decanted and the polymer rinsed with hexane. The rinsed polymer is dissolved in DCM, and precipitated again with hexane (~8× vol.). After centrifugation, the solution is decanted and the polymer dried under high vacuum (FIG. 2 RAFT polymerization).

D. Fractionation of Amine-Protected Poly(Acrylate) Random Copolymer.

The dried, precipitated polymer was dissolved in DCM (~60 mg/mL). Hexane was added until just after the cloud point was reached. The resulting milky solution was centrifuged. The bottom layer (thick liquid representing a desired percent of the polymer, 30-60%) was isolated and dried under vacuum. The remaining upper solution was fully precipitated by further addition of hexane. The second fraction was centrifuged, after which the polymer was isolated and dried under vacuum.

E. Deprotection of Amine-Protected Poly(Acrylate) Random Copolymer.

The dried polymer fractions were deprotected with 2M HCl in acetic acid (~7 ml per 0.400 g polymer) for 1 h. Then the reaction was diluted with water and allowed to stir for 10-15 min. The fractions were then dialyzed with 3500 MW dialysis tubing in high salt, high salt, and water for 15 h, 8 h, and 15 h respectively. The fractions were then lyophilized for 3 days or until dry. The dry samples were brought up at 20 mg/ml in water for further study (FIG. 3 Amine Deprotection).

Example 2

Amphipathic Poly(Acrylate) Random Copolymer Synthesis

A. Polymer LAU 41648-140-B-fr1.

1. Amine-Protected LAU 41648-140-B-fr1 Poly(Acrylate) Random Copolymer Synthesis.

A solution of 2,2'-azobis(2-methylpropionitrile) (AIBN, CAS 78-67-1) was prepared at 1 mg/ml in butyl acetate. A separate solution of 4-cyano-4(phenylcarbonothioylthio) pentanoic acid (CPCPA, CAS 201611-92-9) was prepared at 10 mg/ml in butyl acetate. 2-(2-Boc-aminoethoxy)ethyl acrylate (BAEEA) (1.053 g, 4.059 mmol), propyl methacrylate (CAS 2210-28-8, 0.197 g, 1.54 mmol), CPCPA solution (0.700 mL, 0.0250 mmol), AIBN solution (0.616 mL, 0.00375 mmol), and butyl acetate (4.70 mL) were added to a 20 mL glass vial with stir bar. Monomer molar feed ratio was 72.5:27.5. Theoretical Mw was 50,000. The vial was sealed with a rubber cap and the solution bubbled with nitrogen using a long syringe with a second syringe as the outlet for 1 h. The syringes were removed and the vial heated to 80° C. for 15 h using an oil bath. The solution was allowed to cool to room temperature and transferred to a 50 mL centrifuge tube before hexane (35 mL) was added to the solution. The solution was centrifuged for 2 min at 4,400 rpm. The supernatant layer was carefully decanted and the bottom (solid or gel-like) layer was rinsed with hexane. The bottom layer was then re-dissolved in DCM (7 mL), precipitated in hexane (35 mL) and centrifuged once more. The supernatant was decanted and the bottom layer rinsed with hexane before the polymer was dried under reduced pressure for several hours. Yield 0.762 g. Observed Mw 40,000; Observed composition 66:34, N—BOC-ethylethoxy acrylate:propyl methacrylate. (FIG. 5)

2. Fractionation of Amine-Protected LAU 41648-140-B-fr1 Poly(Acrylate) Random Copolymer.

The dried, precipitated polymer was dissolved in DCM (~60 mg/mL). Hexane was added until just after the cloud point was reached. The resulting milky solution was centrifuged. The bottom layer (thick liquid representing ~30% of polymer) was isolated and dried under vacuum. The remaining upper solution was fully precipitated by further addition of hexane. The second fraction was centrifuged, after which the polymer was isolated and dried under vacuum. Fraction 1 yield was 0.206 g, Mw 50,000; Fraction 2 yield was 0.412 g, Mw 41,000.

3. Deprotection of Amine-Protected LAU 41648-140-B-fr1 Poly(Acrylate) Random Copolymer.

The dried polymer fractions were deprotected with 2M HCl in acetic acid (~7 ml) for 1 h. Then the reaction was diluted with 20 ml of water and allowed to stir for 10-15 min. The fractions were then dialyzed with 3500 MW dialysis tubing in high salt, high salt, and water for 15 h, 8 h, and 15 h respectively. The fractions were then transferred to 50 ml centrifuge tubes and lyophilized for 3 days or until dry. The dry samples were brought up at 20 mg/ml in water for further study.

Similar polymers can be made using protected ethyl, propyl, or butyl amino acrylates copolymerized with a variety of hydrophobic acrylates, including higher hydrophobic (10-24 carbon atoms) acrylates, lower hydrophobic (1-6 carbon atoms) acrylate, or a combination of lower and higher hydrophobic acrylates.

B. Polymer LAU 42101-23-D-fr1.

1. Amine-Protected LAU 42101-23-D-fr1 Poly(Acrylate) Random Copolymer Synthesis.

A solution of 2,2'-azobis(2-methylpropionitrile) (AIBN, CAS 78-67-1) was prepared at 1 mg/ml in butyl acetate. A separate solution of 4-cyano-4(phenylcarbonothioylthio) pentanoic acid (CPCPA, CAS 201611-92-9) was prepared at 10 mg/ml in butyl acetate. Boc-aminopropyl acrylate (BAPA) (0.947 g, 4.133 mmol), 2-ethoxyethyl methacrylate (CAS 2370-63-0, 0.303 g, 1.918 mmol), CPCPA solution (0.350 mL, 0.0125 mmol), AIBN solution (0.308 mL, 0.00188 mmol), and butyl acetate (5.30 mL) were added to a 20 mL glass vial with stir bar. Monomer molar feed ratio was 68:32. The vial was sealed with a rubber cap and the solution bubbled with nitrogen using a long syringe with a second syringe as the outlet for 1 h. The syringes were removed and the vial heated to 80° C. for 15 h using an oil bath. The solution was allowed to cool to room temperature and transferred to a 50 mL centrifuge tube before hexane (35 mL) was added to the solution. The solution was centrifuged for 2 min at 4,400 rpm. The supernatant layer was carefully decanted and the bottom (solid or gel-like) layer was rinsed with hexane. The bottom layer was then re-dissolved in DCM (7 mL), precipitated in hexane (35 mL) and centrifuged once more. The supernatant was decanted and the bottom layer rinsed with hexane before the polymer was dried under reduced pressure for several hours. Yielded 0.851 g. (FIG. 6)

2. Fractionation of Amine-Protected LAU 42101-23-D-fr1 Poly(Acrylate) Random Copolymer.

The dried, precipitated polymer was dissolved in DCM (~60 mg/mL). Hexane was added until just after the cloud point was reached. The resulting milky solution was centrifuged. The bottom layer (thick liquid representing ~30% of polymer) was isolated and dried under vacuum. The remaining upper solution was fully precipitated by further addition of hexane. The second fraction was centrifuged, after which the polymer was isolated and dried under vacuum. Fraction 1 yield was 0.267 g; Fraction 2 yield was 0.308 g.

3. Deprotection of Amine-Protected LAU 42101-23-D-fr1 Poly(Acrylate) Random Copolymer.

The dried polymer fractions were deprotected with 2M HCl in acetic acid (~7 ml) for 1 h. Then the reaction was diluted with 20 ml of water and allowed to stir for 10-15 min. The fractions were then dialyzed with 3500 MW dialysis tubing in high salt, high salt, and water for 15 h, 8 h, and 15 h respectively. The fractions were then transferred to 50 ml centrifuge tubes and lyophilized for 3 days or until dry. The dry samples were brought up at 20 mg/ml in water for further study.

C. Polymer NAR 42020-117A-fr1

1. Amine-Protected NAR 42020-117A-fr1 Poly(Acrylate) Random Copolymer Synthesis.

A solution of 2,2'-azobis(2-methylpropionitrile) (AIBN, CAS 78-67-1) was prepared at 1 mg/ml in butyl acetate. A separate solution of 4-cyano-4(phenylcarbonothioylthio) pentanoic acid (CPCPA, CAS 201611-92-9) was prepared at 10 mg/ml in butyl acetate. Boc-aminopropyl acrylate (BAPA) (0.947 g, 4.13 mmol), butyl methacrylate (BuMA, 0.251 g, 1.77 mmol), octadecyl acrylate (C18A, 0.0956 g, 0.295 mmol), CPCPA solution (0.180 mL, 0.00647 mmol), AIBN solution (0.159 mL, 0.000971 mmol), and butyl acetate (5.66 mL) were added to a 20 mL glass vial with stir bar. Monomer molar feed ratio was 66.5:22.5:5 (66.5 amine:27.5 hydrophobic). The vial was sealed with a rubber cap and the solution bubbled with nitrogen using a long syringe with a second syringe as the outlet for 1 h. The syringes were removed and the vial heated to 80° C. for 15 h using an oil bath. The solution was allowed to cool to room temperature and transferred to a 50 mL centrifuge tube before hexane (35 mL) was added to the solution. The solution was centrifuged for 2 min at 4,400 rpm. The supernatant layer was carefully decanted and the bottom (solid or gel-like) layer was rinsed with hexane. The bottom layer was then re-dissolved in DCM (7 mL), precipitated in hexane (35 mL) and centrifuged once more. The supernatant was decanted and the bottom layer rinsed with hexane before the polymer was dried under reduced pressure for several hours. Mw 130,000 (PDI 1.34); 65% BAPA, 30% BuMA, 5% C18A; Yield 65%. (FIG. 7)

2. Fractionation of Amine-Protected NAR 42020-117A-fr1 Poly(Acrylate) Random Copolymer.

The dried, precipitated polymer was dissolved in DCM (~60 mg/mL). Hexane was added until just after the cloud point was reached. The resulting milky solution was centrifuged. The bottom layer (thick liquid representing ~30% of polymer) was isolated and dried under vacuum. The remaining upper solution was fully precipitated by further addition of hexane. Fraction 1: Mw=149,000; 65% BAPA, 30% BuMA, 5% C18A. Yield 30%

3. Deprotection of Amine-Protected NAR 42020-117A-fr1 Poly(Acrylate) Random Copolymer.

The dried polymer fractions were deprotected with 2M HCl in acetic acid (~7 ml) for 1 h. Then the reaction was diluted with 20 ml of water and allowed to stir for 10-15 min. The fractions were then dialyzed with 3500 MW dialysis tubing in high salt, high salt, and water for 15 h, 8 h, and 15 h respectively. The fractions were then transferred to 50 ml centrifuge tubes and lyophilized for 3 days or until dry. The dry samples were brought up at 20 mg/ml in water for further study.

D. Polymer NAR 41439-141B-fr1.

1. Amine-Protected NAR 41439-141B-fr1 Poly(Acrylate) Random Copolymer Synthesis.

A solution of 2,2'-azobis(2-methylpropionitrile) (AIBN, CAS 78-67-1) was prepared at 1 mg/ml in butyl acetate. A separate solution of 4-cyano-4(phenylcarbonothioylthio) pentanoic acid (CPCPA, CAS 201611-92-9) was prepared at 10 mg/ml in butyl acetate. Boc-aminobutyl acrylate (BABA) (1.05 g, 4.34 mmol), ethyl methacrylate (EtMA, 0.148 g, 1.30 mmol), CPCPA solution (0.335 mL, 0.0120 mmol), AIBN solution (0.295 mL, 0.00180 mmol), and butyl acetate (5.37 mL) were added to a 20 mL glass vial with stir bar. Monomer molar feed ratio was 77:23. The vial was sealed with a rubber cap and the solution bubbled with nitrogen using a long syringe with a second syringe as the outlet for 1 h. The syringes were removed and the vial heated to 80° C. for 15 h using an oil bath. The solution was allowed to cool to room temperature and transferred to a 50 mL centrifuge tube before hexane (35 mL) was added to the solution. The solution was centrifuged for 2 min at 4,400 rpm. The supernatant layer was carefully decanted and the bottom (solid or gel-like) layer was rinsed with hexane. The bottom layer was then re-dissolved in DCM (7 mL), precipitated in hexane (35 mL) and centrifuged once more. The supernatant was decanted and the bottom layer rinsed with hexane before the polymer was dried under reduced pressure for several hours. Mw 38,000 (PDI 1.18); 67% BABA, 33% EtMA; Yield 43%. (FIG. 8)

2. Fractionation of Amine-Protected NAR 41439-141B-fr1 Poly(Acrylate) Random Copolymer.

The dried, precipitated polymer was dissolved in DCM (~60 mg/mL). Hexane was added until just after the cloud point was reached. The resulting milky solution was centrifuged. The bottom layer (thick liquid representing ~30% of polymer) was isolated and dried under vacuum. The remaining upper solution was fully precipitated by further addition of hexane. Fraction 1: Mw=49,000 (PDI 1.10); Yield 45%.

3. Deprotection of Amine-Protected NAR 41439-141B-fr1 Poly(Acrylate) Random Copolymer.

The dried polymer fractions were deprotected with 2M HCl in acetic acid (~7 ml) for 1 h. Then the reaction was diluted with 20 ml of water and allowed to stir for 10-15 min. The fractions were then dialyzed with 3500 MW dialysis tubing in high salt, high salt, and water for 15 h, 8 h, and 15 h respectively. The fractions were then transferred to 50 ml centrifuge tubes and lyophilized for 3 days or until dry. The dry samples were brought up at 20 mg/ml in water for further study.

E. Polymer NAR 41439-71B-fr1 (AKA 41439-117AB-fr1).

1. Amine-Protected NAR 41439-71B-fr1 Poly(Acrylate) Random Copolymer Synthesis.

A solution of 2,2'-azobis(2-methylpropionitrile) (AIBN, CAS 78-67-1) was prepared at 1 mg/ml in butyl acetate. A separate solution of 4-cyano-4(phenylcarbonothioylthio) pentanoic acid (CPCPA, CAS 201611-92-9) was prepared at 10 mg/ml in butyl acetate. 2-(2-Boc-aminoethoxy) ethyl acrylate (BAEEA) (1.09 g, 4.21 mmol), propyl methacrylate (PrMA, CAS 2210-28-8, 0.180 g, 1.41 mmol), CPCPA solution (0.170 mL, 0.00610 mmol), AIBN solution (0.150 mL, 0.000915 mmol), and butyl acetate (5.68 mL) were added to a 20 mL glass vial with stir bar. Monomer molar feed ratio was 76:24. The vial was sealed with a rubber cap and the solution bubbled with nitrogen using a long syringe with a second syringe as the outlet for 1 h. The syringes were removed and the vial heated to 80° C. for 15 h using an oil bath. The solution was allowed to cool to room temperature and transferred to a 50 mL centrifuge tube before hexane (35 mL) was added to the solution. The solution was centrifuged for 2 min at 4,400 rpm. The supernatant layer was carefully decanted and the bottom (solid or gel-like) layer was rinsed with hexane. The bottom layer was then re-dissolved in DCM (7 mL), precipitated in hexane (35 mL) and centrifuged once more. The supernatant was decanted and the bottom layer rinsed with hexane before the polymer was dried under reduced pressure for several hours. Mw 68,000 (PDI 1.70); 69% BAEEA, 31% PrMA; Yield 70%. (FIG. 9)

2. Fractionation of Amine-Protected NAR 41439-71B-fr1 Poly(Acrylate) Random Copolymer.

The dried, precipitated polymer was dissolved in DCM (~60 mg/mL). Hexane was added until just after the cloud point was reached. The resulting milky solution was centrifuged. The bottom layer (thick liquid representing ~30% of polymer) was isolated and dried under vacuum. The remaining upper solution was fully precipitated by further addition of hexane. The second fraction was centrifuged, after which the polymer was isolated and dried under vacuum. Fraction 1: Mw 92,000 (PDI 1.42); Yield 45%. Fraction 2: Mw 52,000 (PDI 1.55); Yield 50%

3. Deprotection of Amine-Protected NAR 41439-71B-fr1 Poly(Acrylate) Random Copolymer.

The dried polymer fractions were deprotected with 2M HCl in acetic acid (~7 ml) for 1 h. Then the reaction was diluted with 20 ml of water and allowed to stir for 10-15 min. The fractions were then dialyzed with 3500 MW dialysis tubing in high salt, high salt, and water for 15 h, 8 h, and 15 h respectively. The fractions were then transferred to 50 ml centrifuge tubes and lyophilized for 3 days or until dry. The dry samples were brought up at 20 mg/ml in water for further study.

F. Polymer Ant 41658-111.

1. Monomer Synthesis. In a 2 L round-bottom flask equipped with a stir bar, 2-(2-aminoethoxy) ethanol (21.1 g, 202.9 mmol, Sigma Aldrich) was dissolved in 350 mL dichloromethane. In a separate 1 L flask, BOC anhydride (36.6 g, 169.1 mmol) was dissolved in 660 mL dichloromethane. The 2 L round-bottom flask was fitted with an addition funnel and BOC anhydride solution was added to the flask over 6 h. The reaction was left to stir overnight. In a 2 L separatory funnel, the product was washed with 300 ml each of 10% citric acid, 10% $K_2CO_3$, sat. $NaHCO_3$, and sat. NaCl. The product, BOC protected 2-(2-aminoethoxy) ethanol, was dried over $Na_2SO_4$, gravity filtered, and DCM was evaporated using rotary evaporation and high vacuum.

In a 500 ml round bottom flask equipped with a stir bar and flushed with argon, BOC protected 2-(2-aminoethoxy) ethanol (27.836 g, 135.8 mmol) was added, followed by 240 mL anhydrous dichloromethane. Diisopropylethyl amine (35.5 ml, 203.7 mmol) was added, and the system was placed in a dry ice/acetone bath. Acryloyl Chloride (12.1 ml, 149.4 mmol) was diluted using 10 ml of dichloromethane, and added drop-wise to the argon flushed system. The system was kept under argon and left to come to room temperature and stirred overnight. The product was washed with 100 mL each of dH$_2$O, 10% citric acid, 10% K$_2$CO$_3$, sat. NaHCO$_3$, and saturated NaCl. The product, BOC-amino ethyl ethoxy acrylate (BAEEA), was dried over Na$_2$SO$_4$, gravity filtered, and DCM was evaporated using rotary evaporation. The product was purified through column chromatography on 29 cm silica using a 7.5 cm diameter column. The solvent system used was 30% ethyl acetate in hexane. Rf: 0.30. Fractions were collected and solvent was removed using rotary evaporation and high vacuum. BAEEA, was obtained with 74% yield. BAEEA was stored in the freezer.

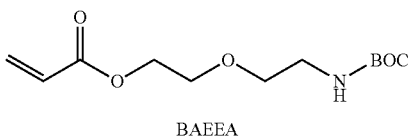 [SMILES: C=CC(=O)OCCOCCNC(=O)OC(C)(C)C]

BAEEA

2. Polymer Synthesis:

Solutions of AIBN (1.00 mg/mL) and RAFT agent (4-Cyano-4(phenylcarbonothioylthio)pentanoic acid (CPCPA), 10.0 mg/mL) in butyl acetate were prepared. Monomer molar feed ratio was 75 BAEEA:25 propyl methacrylate (CAS: 2210-28-8) with 0.108 CPCPA RAFT agent and 0.016 AIBN catalyst (0.00562 total mol).

BAEEA (1.09 g, 4.21 mmol) (A), propyl methacrylate (0.180 g, 1.41 mmol) (B), CPCPA solution (0.170 ml, 0.00609 mmol) (C), AIBN solution (0.150 ml, 0.000915 mmol), and butyl acetate (5.68 ml) were added to a 20 ml glass vial with stir bar. Monomer molar feed ratio was 75:25. The vial was sealed with a rubber cap and the solution was bubbled with nitrogen using a long syringe needle with a second short syringe needle as the outlet for 1 hour. The syringe needles were removed and the system was heated to 80° C. for 15 h using an oil bath. The solution was allowed to cool to room temperature and transferred to a 50 ml centrifuge tube before hexane (35 ml) was added to the solution. The solution was centrifuged for 2 min at 4,400 rpm. The supernatant layer was carefully decanted and the bottom (solid or gel-like) layer was rinsed with hexane. The bottom layer was then re-dissolved in DCM (7 mL), precipitated in hexane (35 mL) and centrifuged once more. The supernatant was decanted and the bottom layer rinsed with hexane before the polymer was dried under reduced pressure for several hours. Molecular weight obtained through MALS: 73,000 (PDI 1.7); Polymer composition obtained using H$^1$NMR: 69:31 Amine:Alkyl.

3. Fractional Precipitation.

The dried, precipitated product was dissolved in DCM (100 mg/mL). Hexane was added until just after the cloud point was reached (~20 ml). The resulting milky solution was centrifuged. The bottom layer (thick liquid representing ~60% of polymer) was extracted and fully precipitated into hexane. The remaining upper solution was also fully precipitated by further addition of hexane. Both fractions were centrifuged, after which the polymer was isolated and dried under vacuum. Fraction 1: Mw 87,000 (PDI 1.5); Fraction 2: Mw 52,000 (PDI 1.5-1.6).

4. MALS Analysis.

Approximately 10 mg of the polymer was dissolved in 0.5 mL 89.8% dichloromethane, 10% tetrahydrofuran, 0.2% triethylamine. The molecular weight and polydispersity (PDI) were measured using a Wyatt Helos II multiangle light scattering detector attached to a Shimadzu Prominence HPLC using a Jordi 5µ 7.8×300 Mixed Bed LS DVB column. Crude Polymer: MW: 73,000 (PDI 1.7), Fraction 1: MW 87,000 (PDI:1.5), Fraction 2: MW 52,000 (PDI 1.5-1.6)

The purified BOC-protected polymer was reacted 2M HCl in Acetic Acid (7 ml) for 0.5 h to remove the BOC protecting groups and produce the amines. 15 mL dH$_2$O were added to the reaction, the solution was transferred to 3500 MW cutoff cellulose tubing, dialyzed against high salt for 24 h, then against dH$_2$O for 18 h. The contents were lyophilized, then dissolved in DI H$_2$O at a concentration of 20 mg/ml. The polymer solution was stored at 2-8° C.

5. Polymer LAU 24B was prepared as above except the monomer feed ratio was 72.5 BAEEA:27.5 propyl methacrylate.

6. Polymer Ant-129-1 was made as essentially as described above except the following monomers were used:

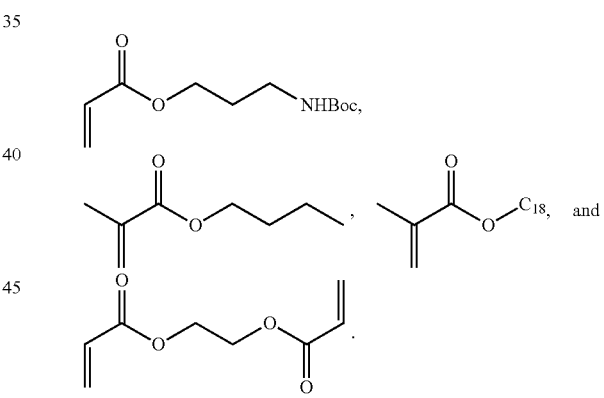

TABLE 1

Polymer Ant-129-1 synthesis reactants.

| | MW (g/mol) | mol % | moles | mass (g) | volume (ml) |
|---|---|---|---|---|---|
| Monomers | | | | | |
| N—Boc-amino-propyl acrylate | 229.27 | 70 | 3.94 × 10$^{-3}$ | 0.9031 | |
| butyl methacrylate | 142.2 | 25 | 1.41 × 10$^{-3}$ | 0.2000 | 0.224 |
| C18 methacrylate | 338.54 | 5 | 2.81 × 10$^{-4}$ | 0.0952 | |
| ethylene glycol diacrylate | 170.16 | 5 | 2.81 × 10$^{-4}$ | 0.0479 | 0.44 |
| other reagents | | | | | |
| CPCPA (RAFT reagent) | 279.38 | 0.213 | 1.2 × 10$^{-5}$ | 0.0033 | 0.335 |
| AIBN (initiator) | 164.21 | 0.032 | 1.8 × 10$^{-6}$ | 0.0003 | 0.295 |

TABLE 1-continued

| Polymer Ant-129-1 synthesis reactants. | | | | | |
|---|---|---|---|---|---|
| | MW (g/mol) | mol % | moles | mass (g) | volume (ml) |
| butyl acetate | | | | | 5.272 |
| $M_{n, th}$ | 100000 | | | | |
| total units per CTA | 469.56 | | | | |
| % CTA | 0.213 | | | | |

Example 3

Amphipathic Poly(Acrylate) Random Copolymer Synthesis—Non-RAFT Polymerization A. Polymer LAU 41305-38-17-19 Random Polyacrylate.

1. Synthesis of N-Boc-Amino-Propyl-Acrylate (BAPA).

In a 500 ml round bottom flask equipped with a stir bar and flushed with argon, 3-(BOC-amino)1-propanol (TCI) (135.8 mmol) was added, followed by 240 mL anhydrous dichloromethane. Diisopropylethyl amine (203.7 mmol) was added, and the system was placed in a dry ice/acetone bath. Acryloyl Chloride (149.4 mmol) was diluted using 10 ml of dichloromethane, and added drop-wise to the argon flushed system. The system was kept under argon and left to come to room temperature and stirred overnight. The product was washed with 100 mL each of $dH_2O$, 10% citric acid, 10% $K_2CO_3$, sat. $NaHCO_3$, and saturated NaCl. The product, BOC-amino propyl acrylate (BAPA), was dried over $Na_2SO_4$, gravity filtered, and DCM was evaporated using rotary evaporation. The product was purified through column chromatography on 29 cm silica using a 7.5 cm diameter column. The solvent system used was 30% ethyl acetate in hexane. Rf: 0.30. Fractions were collected and solvent was removed using rotary evaporation and high vacuum. BAPA was obtained with 74% yield. BAPA was stored in the freezer.

2. Polymer Synthesis.

80% BAPA, 20% ethyl methacrylate (CAS 97-63-2), (3% AIBN catalyst) mole feed ratio (0.0105 total mol). BAPA (8.40 mmol) and ethyl methacrylate (2.10 mmol) were added to a 15 ml reaction tube equipped with a stir bar. Acetonitrile (11.5 ml) was added followed by AIBN (0.315 mmol). The above steps were repeated in order to have two reactions run in tandem. The reaction mixture was purged with $N_2$ for 30 min. The reaction tubes were then capped and transferred to an oil bath and heated at 60° C. for 3 h. The tubes were removed and the contents were combined. Acetonitrile was evaporated through rotary evaporation and high vacuum and the crude polymer was dissolved in 74.8% dichloromethane/ 25% tetrahydrofuran/0.2% triethylamine solution at 50 mg/ml. Three injections of crude polymer solution (500 mg, 10 ml) were purified on a Jordi gel fluorinated divinyl benzene $10^4$ Å column (internal diameter: 22 mm, length: 500 mm) used at a flow rate of 5.0 ml/min. Polymer elution was detected using a Shimadzu RID-10A refractive index collector. Fractions from 17.16 min-19.18 min were collected and combined. The solvent was evaporated through rotary evaporation. The purified BOC-protected polymer was reacted with 2M HCl in glacial acetic acid (7 ml) for 1.5 h to remove the BOC protecting groups and produce the amines. 40 ml $dH_2O$ were added to the reaction, the solution was transferred to 3500 MW cutoff cellulose tubing, dialyzed against high salt for 24 hr, then against $dH_2O$ for 18 h. The contents were evaporated to dryness, then dissolved in 30 ml $dH_2O$ and lyophilized twice. Mw of the protected polymer was 100 kDa. Calculated Mw of the deprotected polymer was 61 kDa. PDI=1.381.

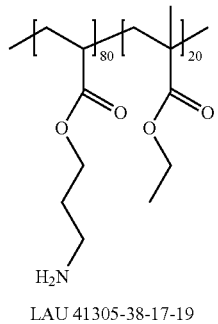

LAU 41305-38-17-19

80 and 20 represent percent monomer composition in the polymer

B) Random Copolymerization of N-Boc-Ethylethoxy Acrylate and Propyl Methacrylate.

Copolymers consisting of Amine acrylate/$C_n$ methacrylate were synthesized as follows. The monomers were weighed brought up into dioxane at the indicated ratios. AIBN (azobis-isobutyronitrile) was added and nitrogen was bubbled through the reaction at RT for 1 h. The reaction mixture was then placed into an oil bath at 60° C. for 3 h. The polymer was then dried under reduced pressure. The polymer was purified by GPC. After which the polymer fractions were deprotected with 7 ml 2M HCl in Acetic Acid for 30 min at RT. After 30 min, 15 ml of water was added to the reaction mixture, and the mixture was transferred into 3.5 kDa MWCO dialysis tubing. The polymer was dialyzed overnight against NaCl and then another day against $dH_2O$. The water was then removed through lyophilization, and the polymer was dissolved in $dH_2O$.

Polymer Lau41648-106.

Monomer molar feed ratio was 80 BAEEA:20 propyl methacrylate (CAS:2210-28-8) and 3% AIBN catalyst based on total monomer moles. BAEEA (6.53 g, 25.2 mmol) (A), propyl methacrylate (0.808 g, 6.3 mmol) (B), AIBN (0.155 g, 0.945 mmol), and dioxane (34.5 ml) were added to a 50 ml glass tube with stir bar. Compounds A and B were prepared described above. The reaction was set up in triplicate. Each solution was bubbled with nitrogen using a long pipette for 1 hour. The pipette was removed and each tube carefully capped. Then each solution was heated at 60° C. for 3 h using an oil bath. Each solution was allowed to cool to room temperature and combined in a round bottom. The crude polymer was dried under reduced pressure. Molecular weight obtained through MALS: 55,000 (PDI 2.1); Polymer composition obtained using $H^1$NMR: 74:26 Amine:Alkyl.

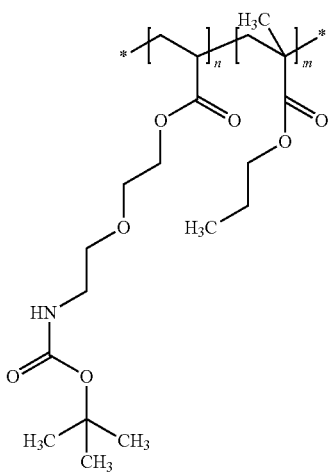

Lau41648-106

GPC Fractionation.

The dried crude polymer was brought up at 50 mg/ml in 75% dichloromethane, 25% tetrahydrafuran, and 0.2% triethylamine. The polymer was then fractionated on a Jordi Gel DVB $10^4$ Å-500 mm/22 mm column using a flow rate of 5 ml/min and 10 ml injections. An earlier fraction was collected from 15-17 minutes, and a later fraction was collected from 17-19 minutes. Fraction 15-17: Mw 138,000 (PDI 1.1); Fraction 17-19: Mw 64,000 (PDI 1.2).

MALS Analysis.

Approximately 10 mg of the polymer was dissolved in 0.5 mL 89.8% dichloromethane, 10% tetrahydrofuran, 0.2% triethylamine. The molecular weight and polydispersity (PDI) were measured using a Wyatt Helos II multiangle light scattering detector attached to a Shimadzu Prominence HPLC using a Jordi 5μ 7.8×300 Mixed Bed LS DVB column. Crude Polymer: MW: 55,000 (PDI 2.1), Fraction 15-17: MW 138,000 (PDI:1.1), Fraction 17-19: MW 64,000 (PDI 1.2)

The purified BOC-protected polymer was reacted 2M HCl in Acetic Acid (7 ml) for 0.5 h to remove the BOC protecting groups and produce the amines. 15 mL dH$_2$O were added to the reaction, the solution was transferred to 3500 MW cutoff cellulose tubing, dialyzed against high salt for 24 h, then against dH$_2$O for 18 h. The contents were lyophilized, then dissolved in DI H$_2$O at a concentration of 20 mg/ml. The polymer solution was stored at 2-8° C.

Example 4

Masking Agents

A. Galactose Disubstituted Maleic Anhydride Masking Agents.

1) Compound 10

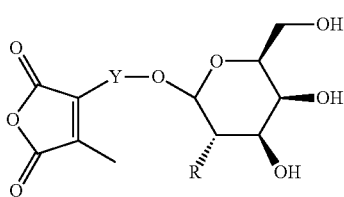

wherein

Y is neutral linker such as, but not limited to:
—(CH$_2$)a-(O—CH$_2$—CH$_2$)$_b$—NH—CO—(CH$_2$)$_c$—, wherein a, b and c are independently integers from 1-6, and R is a galactose derivative having affinity for the asialoglycoprotein receptor selected from the list comprising:

OH (Galactose),

NH$_2$ (D-Galactosamine),

NH—CO—H(N-formyl-D-galactosamine),

NH—CO—CH$_3$ (N-acetyl-D-galactosamine (GalNAc)),

NH—CO—CH$_2$CH$_3$ (N-propionyl-D-galactosamine),

NH—CO—CH$_2$CH$_2$CH$_3$ (N-n-butanoyl-D-galactosamine), and

NH—CO—CH(CH$_3$)$_2$ (N-iso-butanoyl-D-galactosamine).

Reaction of the maleic anhydride with an anime group on the polymers results in formation of a pH labile linkage between the galactose and a polymer amine.

2) Compound 11

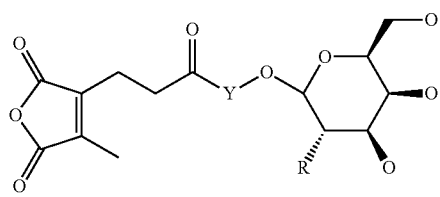

wherein

Y is neutral linker such as, but not limited to: —NH—(CH$_2$—CH$_2$—O)$_b$—(CH$_2$)$_a$—, wherein b and c are independently integers from 1-6, and R is as defined above for compound 10.

3) Compound 12

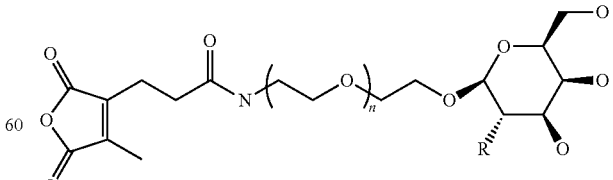

wherein n is an integer from 1 to 6 and R is as defined above for compound 10.

4) Compound 13: N-Acetyl-galactosamine-PEG-methyl maleic anhydride

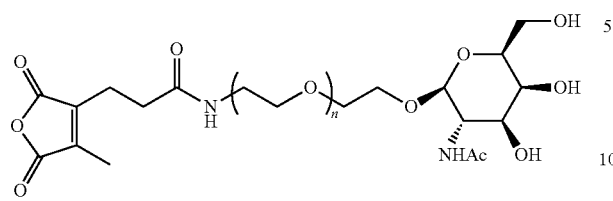

wherein n is an integer from 1 to 6.

5) Alkyl spacer groups may also be used as illustrated in compound 14.

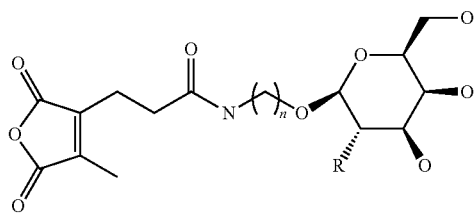

wherein n is an integer from 0 to 10 and R is a defined above for compound 10.

B. Polyethylene Glycol Disubstituted Maleic Anhydride Masking Agents.

1) Compound 15

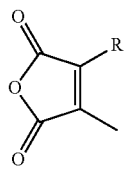

wherein R is neutral and comprises a polyethylene glycol.

Reaction of the maleic anhydride with an anime group on the polymers results in formation of a pH labile linkage between the PEG and a polymer amine.

2) Compound 16

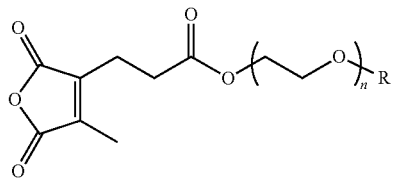

wherein
n is an integer from 1 to 500, and
R is selected from the group consisting of —H, —CH$_3$, and —CH$_2$—CH$_3$.

Preferably, n is an integer from 2 to 100. More preferably, the PEG contains from 5 to 20 ethylene units (n is an integer from 5 to 20). More preferably, PEG contains 10-14 ethylene units (n is an integer from 10 to 14). The PEG may be of variable length and have a mean length of 5-20 or 10-14 ethylene units. Alternatively, the PEG may be monodisperse, uniform or discrete; having, for example, exactly 11 or 13 ethylene units.

C. Dipeptide Masking Agent, Compound 16

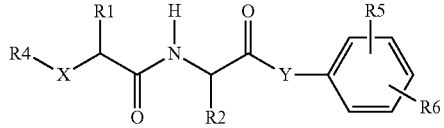

R1 and R2 are the R groups of amino acids,
R4 is a targeting ligand of a steric stabilizer,
X is —NH—, —O—, or —CH$_2$—,
Y is —NH— or —O—
R5 is at position 2, 4, or 6 and is —CH2-O—C(O)—O—Z wherein Z carbonate, and
R6 is independently hydrogen, alkyl, or halide at each of positions 2, 3, 4, 5, or 6 except for the position occupied by R5.

Example 5

Conjugation of siRNA to Poly(Acrylate) Random Copolymers Via Disulfide Bonds

A. SATA/SMPT Linkage.

N-succinimidyl-5-acetylthioacetate (SATA)-modified polynucleotides were synthesized by reaction of 5' amine-modified siRNA with 1 weight equivalents (wt. eq.) of SATA reagent (Pierce) and 0.36 wt. eq. of NaHCO$_3$ in water at 4° C. for 16 h. The protected thiol modified siRNAs were precipitated by the addition of 9 volumes of ethanol and incubation at −78° C. for 2 h. The precipitate was isolated, dissolved in 1×siRNA buffer (Dharmacon), and quantitated by measuring absorbance at the 260 nm wavelength.

Polymer in 5 mM TAPS pH 9, was modified by addition of 1.5 wt % 4-succinimidyloxycarbonyl-α-methyl-α-[2-pyridyldithio]-toluene (SMPT, Pierce). 1 h after addition of SMPT, SMPT-polymer was added to isotonic glucose solution containing 5 mM TAPS pH 9. To this solution was added SATA-modified siRNA. In this way, the polynucleotide was conjugated to the polymer via a reversible disulfide bone. A disulfide bond for conjugation between the polymer and siRNA provides for reversibility in the reducing environment of the cytoplasm.

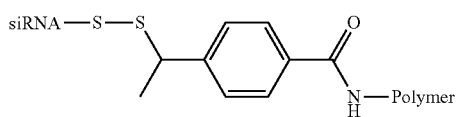

The siRNA-polymer conjugate was masked by adding to the solution HEPES free base followed by a mixture of CDM-NAG and CDM-PEG. The solution was then incubated 1 h at room temperature (RT) before injection.

B. SATA/SPDP Linkage.

siRNA having a 5'-amino group on the sense strand is reacted with SATA in the presence of HEPES base pH 7.5. Separately, poly(acrylate) is reacted with 3-(2-pyridyldithio) propionic acid N-hydroxysuccinimide ester (SPDP) in the presence of HEPES pH 7.5. The modified siRNA and modified polymer were then combined to allow covalent attachment of the siRNA to the polymer.

C. 5-methyl-2-iminothiolane Linkage.

siRNA having an strand terminal amino group is reacted with S-acetyl groups to yield siRNA-SAc. The polymer is reacted with 5-methyl-2-iminothiolane (M2IT) in the presence of DTNB to yield the polymer having an activated disulfide.

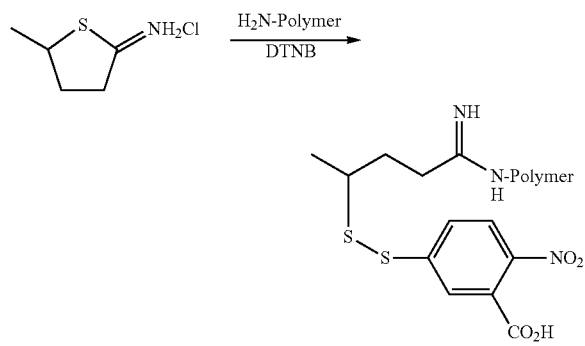

The above modified polymer is then reacted with siRNA-SAc to form the siRNA-polymer conjugate.

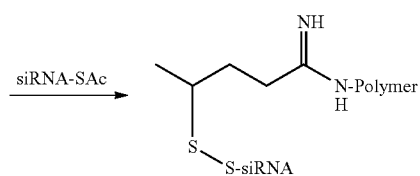

It is noted that disulfide bonds can be made with varying kinetics of cleavage in the reducing environment in a typical mammalian cell.

C. Maleic Anhydride Linkage.

siRNA having a strand terminal amino group is reacted with a disubstituted maleic anhydride, such as a 2-propionic-3-methylmaleic anhydride or CDM-thioester in the presence alkaline buffer (e.g., HEPES pH 7.9). To the siRNA-maleic anhydride is added the poly(acrylate). The maleic anhydride then reacts with amines on the polymer.

Example 6

Reversible Modification (Masking) of Membrane Active Poly(Acrylate) Random Copolymers A. Modification with Maleic Anhydride-Based Masking Agents.

Prior to modification, 5-7×mg of disubstituted maleic anhydride masking agent (e.g. CDM-NAG) was lyophilized from a 0.1% aqueous solution of glacial acetic acid. To the dried disubstituted maleic anhydride masking agent was added a solution of x mg polymer in 0.2×mL of isotonic glucose and 10×mg of HEPES free base. Following complete dissolution of anhydride, the solution was incubated for at least 30 min at RT prior to animal administration. Reaction of disubstituted maleic anhydride masking agent with the polymer yielded:

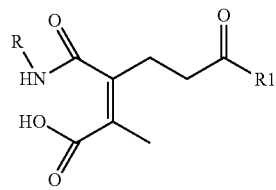

wherein R is poly(acrylate) polymer and R1 comprises a targeting ligand or steric stabilizer. The anhydride carboxyl produced in the reaction between the anhydride and the polymer amine exhibits $\sim 1/20^{th}$ of the expected charge (Rozema et al. Bioconjugate Chemistry 2003). Therefore, the membrane active polymer is effectively neutralized rather than being converted to a highly negatively charged polyanion.

In some applications, the polymer was modified in a two-step process. First CDM-based masking agents with shielding (PEG) and targeting groups were mixed in a ratio of 2:1 (wt:wt) shielding to targeting agent. The polymer was modified with 2×mg of the CDM masking agents mixture for 30 min, followed by attachment of siRNA. The polymer-siRNA conjugate was then further modified with 5×mg of the CDM masking agents mixture. The solution was then incubated at least 1 h at room temperature (RT) before injection into animals.

B. Modification with Protease Cleavable Masking Agents.

Activated (amine reactive) carbonates of p-acylamidobenzyl alcohol derivatives are reacted with amino groups of amphipathic membrane active polyamines in $H_2O$ at pH>8 to yield a p-acylamidobenzyl carbamate.

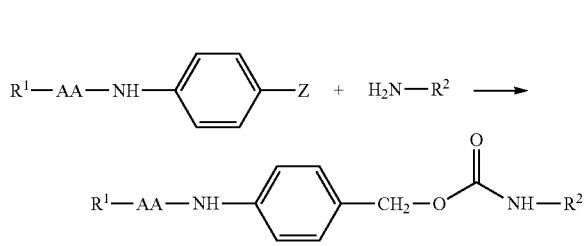

$R^1$ comprises an targeting group ligand (either protected or unprotected) or a PEG, $R^2$ is an amphipathic membrane active poly(acrylate), AA is a dipeptide (either protected or unprotected), and Z is an amine-reactive carbonate.

To ×mg polymer was added 10-12×mg of HEPES free base in isotonic glucose. To the buffered polymer solution was added 2× to 16×mg 200 mg/ml dipeptide masking agent in DMF. In some applications, the polymer was modified with 2×mg dipeptide masking agent followed by attachment of siRNA. The polymer-siRNA conjugate was then further modified with 6× to 8×mg dipeptide masking agent. The solution was then incubated at least 1 h at room temperature (RT) before injection into animals. In some applications, the polymer was modified with 2×mg PEG dipeptide masking agent followed by attachment of siRNA. The polymer-siRNA conjugate was then further modified with 6× to 8×mg targeting ligand dipeptide masking agent. The solution was then incubated at least 1 h at room temperature (RT) before injection into animals.

In some applications, the polymer was modified with 2×mg dipeptide masking agent followed by attachment of siRNA. The polymer-siRNA conjugate was then further modified with 6× to 8×mg CDM-based masking agent. The solution was then incubated at least 1 h at RT before injection into animals. In some applications, the polymer was modified with 2×mg PEG dipeptide masking agent followed by attachment of siRNA. The polymer-siRNA conjugate was then further modified with 6× to 8×mg targeting ligand CDM-based masking agent. The solution was then incubated at least 1 h at room temperature (RT) before injection into animals.

Example 7

Conjugate Formation—Masking and Polynucleotide Attachment

A) Polymer was modified with SMPT. After 1 h, 2 wt equivalents of CDM-NAG (N-acetylgalactoseamine) and/or CDM-PEG (average 11 unites) was added to the polymer in the presence of HEPES base. To this solution was added SATA-siRNA. After overnight incubation, a CDM-NAG and/or CDM-PEG was added to the conjugate.

B) Polymer was modified with SMPT. After 1 h, 2 wt equivalents of FCit-NAG (N-acetylgalactoseamine) and/or FCit-PEG (average 11 unites) was added to the polymer in the presence of HEPES base. To this solution was added SATA-siRNA. After overnight incubation, a FCit-NAG and/or FCit-PEG was added to the conjugate.

Example 8 siRNAs

The siRNAs had the following sequences:

```
Factor VII - rodent
sense:
                                              (Seq ID 1)
(Chol)-5' GfcAfaAfgGfcGfuGfcCfaAfcUfcAf(invdT) 3' antisense:
                                              (Seq ID 2)
5' pdTsGfaGfuUfgGfcAfcGfcCfuUfuGfcdTsdT 3'
or sense
                                              (Seq ID 3)
5' GGAUfCfAUfCfUfCfAAGUfCfUfUfACfdTsdT 3' antisense
                                              (Seq ID 4)
5' GUfAAGACfUfUfGAGAUfGAUfCfCfdTsdT 3'

Factor VII - primate
Sense
                                              (Seq ID 5)
(chol)-5' uuAGGfuUfgGfuGfaAfuGfgAfgCfuCfaGf
(invdT) 3'

Antisense
                                              (Seq ID 6)
5' pCfsUfgAfgCfuCfcAfuUfcAfcCfaAfcdTsdT 3'

ApoB siRNA:
sense
                                              (Seq ID 7)
(cholC6SSC6)-5' GGAAUCuuAuAuuuGAUCcAsA 3' antisense
                                              (Seq ID 8)
5' uuGGAUcAAAuAuAAGAuUCcscsU 3' siLUC
sense
                                              (Seq ID 9)
(chol) 5'-uAuCfuUfaCfgCfuGfaGfuAfcUfuCfgAf
(invdT)-3' antisense
                                              (Seq ID 10)
5'-UfcGfaAfgUfaCfuCfaGfcGfuAfaGfdTsdT-3'
lower case = 2'-O-CH3 substitution
s = phosphorothioate linkage
f after nucleotide = 2'-F substitution
d before nucleotide = 2'-deoxy
```

RNA synthesis was performed on solid phase by conventional phosphoramidite chemistry on an ÄKTA Oligopilot 100 (GE Healthcare, Freiburg, Germany) and controlled pore glass (CPG) as solid support.

Example 9

Synthesis of Amino-Modified RNA

RNA equipped with a C-6-aminolinker at the 5'-end of the sense strand was produced by standard phosphoramidite chemistry on solid phase at a scale of 1215 µmol using an ÄKTA Oligopilot 100 (GE Healthcare, Freiburg, Germany) and controlled pore glass as solid support (Prime Synthesis, Aston, Pa., USA). RNA containing 2'-O-methyl nucleotides were generated employing the corresponding phosphoramidites, 2'-O-methyl phosphoramidites and TFA-hexylaminolinker amidite (Sigma-Aldrich, SAFC, Hamburg, Germany). Cleavage and deprotection as well as purification was achieved by methods known in the field (Wincott F., et al, NAR 1995, 23, 14, 2677-84).

Example 10

In Vivo Delivery of RNAi Polynucleotides Using Poly(Acrylate) Delivery Polymers

RNAi polynucleotide conjugates and masked poly(acrylate) polymers were synthesized as described above. Six to eight week old mice (strain C57BL/6 or ICR, ~18-20 g each) were obtained from Harlan Sprague Dawley (Indianapolis, Ind.). Mice were housed at least 2 days prior to injection. Feeding was performed ad libitum with Harlan Teklad Rodent Diet (Harlan, Madison Wis.). Mice were injected by infusion into the tail vein with 0.4 mL solution of delivery peptide-siRNA conjugates into the tail vein unless stated otherwise. The composition was soluble and nonaggregating in physiological conditions. Injection into other vessels, e.g. retro-orbital injection, are predicted to be equally effective.

Wistar Han rats, 175-200 g were obtained from Charles River (Wilmington, Mass.). Rats were housed at least 1 week prior to injection. Injection volume for rats was typically 1 ml.

The indicated amount of polymer-siRNA conjugate was administered to Cynomolgus macaque (*Macaca fascicularis*) primates (male, 3.0 to 8.0 kg) via injection into the saphenous vein using a 22 to 25 gauge intravenous catheter. As a control, another set of primates were injected with isotonic glucose. Blood tests for blood urea nitrogen (BUN), alanine transaminase (ALT), aspartate aminotransferase (AST), and creatinine were performed on a Cobas Integra 400 (Roche Diagnostics) according to the manufacturer's recommendations.

Mice, rats, and primates were fasted for 4 h, 16 h, or overnight, before injection. Primates were fasted overnight before blood collection or tissue harvest. Blood samples were collected by submandibular bleeding for mice, from jugular vein for rats, and from femoral vein for primates. For mice and rats, samples were taken 2 days after polymer injection, unless indicated otherwise. For primates, blood samples are collected on day 2 (24 h after injection) and day 4 (72 h after injection). Further, for primates, blood sample collections were carried out up to day 81. Serum for use in Western assays was collected and added to an equal volume of Complete Protease Inhibitor Cocktail containing EDTA (Roche, Indianapolis Ind.) and stored at −20° C. Total RNA was isolated from liver immediately after harvest using TRI-REAGENT® according to the manufacturer's protocol (Molecular Research Center, Cincinnati Ohio).

Serum ApoB Levels Determination.

Serum ApoB protein levels were determined by standard sandwich ELISA methods. Briefly, a polyclonal goat anti-mouse ApoB antibody and a rabbit anti-mouse ApoB antibody (Biodesign International) were used as capture and detection antibodies respectively. An HRP-conjugated goat anti-rabbit IgG antibody (Sigma) was applied afterwards to bind the ApoB/antibody complex. Absorbance of tetramethyl-benzidine (TMB, Sigma) colorimetric development was then measured by a Tecan Safire2 (Austria, Europe) microplate reader at 450 nm.

Plasma Factor VII (F7) Activity Measurements.

Plasma samples from animals were prepared by collecting blood (9 volumes) (by submandibular bleeding for mice or from jugular vein for rats) into microcentrifuge tubes containing 0.109 mol/L sodium citrate anticoagulant (1 volume) following standard procedures. F7 activity in plasma is measured with a chromogenic method using a BIOPHEN VII kit (Hyphen BioMed/Aniara, Mason, Ohio) following manufacturer's recommendations. Absorbance of colorimetric development was measured using a Tecan Safire2 microplate reader at 405 nm.

Example 11

Amphipathic Cationic Poly(Acrylate) Random Copolymers are Effective In Vitro Transfection Reagents A. The following polymers were synthesized via RAFT polymerization as described above.

1) ethyl(boc)aminoacrylate+butyl methacrylate (EAA-BuMA)

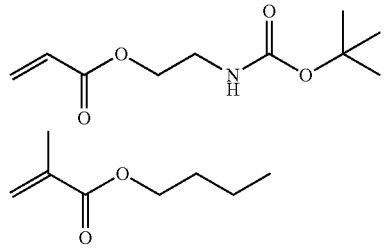

2) ethoxyethyl(boc)aminoacrylate+secbutyl acrylate copolymers (EEAA-SecBuA)

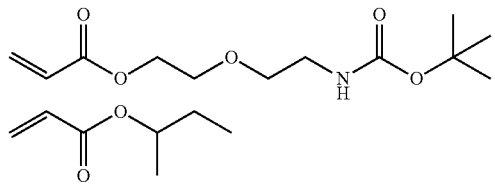

3) ethoxyethyl(boc)aminoacrylate+butyl acrylate copolymers (EEAA-BuA)

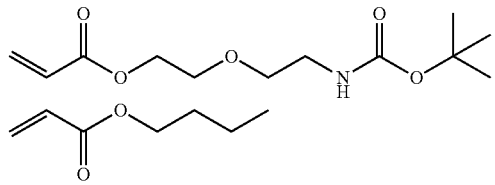

B. The indicated copolymer (500 mg) was dissolved in a solution of 2 N HCl in acetic acid (5 mL) and stirred for 1 h to remove the amine protecting groups. The solution was diluted with water (30 mL) and dialyzed against an aqueous NaCl solution and then deionized water over two days. The solution was then lyophilized and re-dissolved in $H_2O$ to make up 20 mg/mL solutions. Hep3B-SEAP (hepatocellular carcinoma), MCF7 (breast cancer), HT29 (colon cancer), HepG2-SEAP (hepatocellular carcinoma), or A375 (melanoma) cells as indicated were plated in 96-well culture plates at a density of 10,000 cells/well. Cells were transfected with either 1.5 μg/mL or 3 μg/mL of copolymer and 500 ng/mL of Aha1 siRNA prepared in OPTI-MEM reduced-serum medium (Gibco). 24 h post-transfection, the cells were lysed and processed for quantitative real-time PCR (qRT-PCR) using the TaqMan Gene Expression Cells-to-CT Kit (Life Technologies). Biplex qRT-PCR was performed using TaqMan assays for human Aha1 and human CycA on a StepOne Real-Time PCR System (Life Technologies). Analysis was performed using the ΔΔCT method of relative gene expression quantitation.

The polymers were effective in delivering siRNA to (transfecting) a wide variety cells in vitro. For these amphipathic poly(acrylate) RAFT copolymers, amine content from 40% to 80% was effective. Generally, for a given amine content, increasing molecular weight yielded polymers with increasing transfection activity. See FIGS. 11, 12, and 13.

Example 12

Tumor Targeting with Protease Cleavable DPCs

A) Target Gene Knockdown Measurement.

For all studies presented below an siRNA specific for the Aha1 gene transcript, the target gene, was used. An siRNA to the enhanced green fluorescent protein (EGFP) was used as an off-target control. The Aha1 siRNA was complementary to a sequence motif in Aha1 that is 100% homologous in both the human and mouse gene. Therefore, delivery of Aha1 siRNA either into cells of the host or into tumor cells in the human xenograft results in mRNA cleavage and degradation.

Using sequence motifs different in mouse and human Aha1 genes, PCR primers were designed that enabled quantitative measurement of both human Aha1 and mouse Aha1 mRNA levels in tissue samples that contained a mixed population of cell types. At 24, 48 or 72 hours after siRNA delivery, tumors were harvested with some healthy mouse liver tissue attached and were processed in Tri-Reagent (Invitrogen) for total RNA isolation. Both human and mouse Aha1 mRNA levels were then measured by qPCR assays, using human Cyc-A and mouse β-actin as internal reference genes. Aha1 mRNA levels in animals from mock-injected animals, or mice that received the off-target control GFP siRNA were considered 100%. Results are expressed as percent of Aha1 mRNA level relative to control and are shown in Tables below.

B) Orthotopic Hepatocellular Carcinoma (HCC) Tumor Model Mice.

HegG2, Hep3B, or HuH7 cells hepatocellular carcinoma were co-transfected with 2 expression vectors, pMIR85 a human placental secreted alkaline phosphatase (SEAP) vector and pMIR3 a neomycine/kanamycin-resistance gene vector, to develop cell lines with stable SEAP expressionCell were grown DMEM supplemented with 10% FBS and 300 ug/ml G418), collected, counted, and mixed with matrigel (BD Biosciences) (50% by volume). Athymic nude or Scid beige mice were anesthetized with ~3% isoflourane and placed in a sternal recumbent position. A small, 1-2 cm, midline abdominal incision was made just below the xyphoid. Using a moist cotton swab, the left lobe of the liver was gently exteriorized. The left lobe of the liver was gently retracted and a syringe needle was inserted into the middle of the left lobe. The syringe needle was inserted with the bevel down about 0.5 cm just under the capsule of the liver. 10 μl of cell/matrigel mixture, containing 100,000 cells, was injected into the liver using a syringe pump. The needle was left in the liver for a few moments (15-20 seconds) to ensure the injection was complete. SEAP-HepG2 cells were injected into athymic nude mice. SEAP-Hep3B and SEAP-HuH7 cells were injected into Scid beige mice. The syringe was then removed from the needle from the liver and a cotton swab was placed over the injection site to prevent leakage of the cells or bleeding. The Matrigel/cells mixture formed a mass that was visible and did not disappear after removal of the needle. The liver lobe was then gently placed back into the abdomen and the abdominal wall was closed. Sera were collected once per week after tumor implantation and subjected to SEAP assay to monitor tumor growth. For most studies, tumor mice were used 4-5 weeks after implantation, when tumor measurements are predicted to be around 4-8 mm based on SEAP values.

C) Colorectal Metastatic Tumor Model.

HT29 cells were grown in McCoy's 5a medium supplemented with 10% FBS, collected, counted, and mixed with matrigel (BD Biosciences) (50% by volume). Athymic nude mice were anesthetized with ~3% isoflourane and placed in a sternal recumbent position. A small, 1-2 cm, midline abdominal incision was made just below the xyphoid. Using a moist cotton swab, the left lobe of the liver was gently exteriorized. The left lobe of the liver was gently retracted and a syringe needle was inserted into the middle of the left lobe. The syringe needle was inserted with the bevel down about 0.5 cm just under the capsule of the liver. 5 μl of cell/matrigel mixture, containing 40,000 cells, was injected into the liver using a syringe pump. The needle was left in the liver for a few moments (15-20 seconds) to ensure the injection was complete. The syringe was then removed from the liver and a cotton swab was placed over the injection site to prevent leakage of the cells or bleeding. The Matrigel/cells mixture formed a mass that was visible and did not disappear after removal of the needle. The liver lobe was then gently placed back into the abdomen and the abdominal wall was closed. Tumor mice were used 4-5 weeks after implantation.

Example 13

In Vivo Knockdown of Target Gene Expression in HepG2-SEAP Orthotopic Hepatocellular Carcinoma (HCC) Model Following $PEG_{24}$-Val-Cit DPC Administration Ant-129-1 polymer DPCs were modified (masked) with either 18× weight excess $PEG_{24}$-Phe-Cit masking agent (or $PEG_{24}$-Val-Cit masking agent) or with 7×$PEG_{550}$-CDM as described above. Aha1-siRNA or GFP-siRNA (off-target control) was attached to the polymer as described above (4:1 weight ratio). DPCs were not purified by gel filtration prior to delivery, and no targeting ligand was added. A 320 μg (polymer weight) DPC conjugate in 200 μl isotonic glucose per animal was administered by tail vein injections (n=3 per group). After 24 hours, animals received second injection of 320 μg (polymer weight) DPC conjugate in 200 μl isotonic glucose. 48 hours after the second injection, serum samples were collected to assess toxicity by measuring liver enzyme (ALT and AST) and blood urea nitrogen (BUN) levels, followed by tissue harvest, and qPCR analysis.

Using $PEG_{24}$-Val-Cit-Ant-129-1-siRNA DPCs to delivery Aha1 siRNA, resulted 46% knockdown of the Aha1 gene in human tumor cells (Table 2). In contrast to human Aha1 knockdown levels, mouse Aha1 was knocked down 70% in response $PEG_{24}$-Val-Cit-Ant-129-1-siRNA DPC administration (Table 2). Compared to similar DPCs made with disubstituted maleic anhydride masking agents ($PEG_{550}$-CDM), endogenous hepatocyte Aha1 knockdown was decreased. As indicated by ALT, AST and BUN levels, the $PEG_{24}$-Val-Cit DPCs were well tolerated and did not exhibit toxicity (Table 3).

TABLE 2

Aha1 knockdown in HepG2 liver tumor model by maleic anhydride modified vs. peptide cleavable modified Aha1 siRNA DPCs.

|  | control siRNA | $PEG_{550}$-CDM DPC Aha1 siRNA | $PEG_{24}$-Val-Cit DPC Aha1 siRNA |
|---|---|---|---|
| human Aha1 levels (tumor) | 100 ± 8.0 | 54.4 ± 7.3 | 54.9 ± 7.6 |
| mouse Aha1 levels (hepatocytes) | 100 ± 9.2 | 7.5 ± 0.9 | 30.4 ± 3.1 |

TABLE 3

Blood chemistry toxicity markers following administration of maleic anhydride modified or peptide cleavable modified Aha1 siRNA DPCs.

|  | control siRNA | $PEG_{550}$-CDM DPC Aha1 siRNA | $PEG_{24}$-Val-Cit DPC Aha1 siRNA |
|---|---|---|---|
| ALT | 44.3 ± 5.1 | 58.0 ± 37.5 | 35.0 ± 11.3 |
| AST | 81.7 ± 4.0 | 102.3 ± 57.5 | 67.7 ± 14.4 |
| BUN | 25.3 ± 4.2 | 23.0 ± 3.5 | 21.3 ± 1.2 |

Example 14

Knockdown of Targeting Gene Expression with Bispecific Antibody (bsAb)-Targeted DPCs (2011090701)

Ant-129-1 polymer was modified with 5× Dig-PheCit (Dig-FCit) masking agent as described above. siRNA was then attached to the conjugate. Finally, the Dig-FCit-Ant-129-1-siRNA conjugate was further modified with 8× (wt) $PEG_{12}$-FCit. Aha1-siRNA (RD-09070) or GFP siRNA (RD-05814) was attached at a 4:1 polymer:siRNA weight ratio. $PEG_{12}$-FCit DPCs were purified on Sephadex G50 spin columns to remove unbound reagents.

Cell targeting bispecific antibodies (bsAb) were made specific to heparan sulfate proteoglycan Glypican-3 (GPC3), a cell surface heparan sulfate proteoglycan known to be highly expressed in HepG2-SEAP cells, and digoxigenin (Dig). As a control, bispecific antibodies specific to the protein CD33 (marker of bone marrow-derived hematopoietic stem cells) and Dig were made. CD33 is not expressed by HepG2-SEAP cells. BsAbs were complexed with modified DPCs at a 1.25:1 weight ratio to provide an estimated 1:1 molar ratio. Complexes were formed in PBS at least 30 minutes prior to delivery.

DPCs were administered to HepG2-SEAP tumor bearing mice, either with or without bsAb targeting agent. Each animal (n=3 per group) received a single dose of 250 µg (polymer wt.) DPCs. DPCs were injected into tail vein of mice in 200 µl sterile PBS. Serum and tissue samples were harvested 48 hours later and analyzed as described above. As shown in Table 4, a single dose of bsAb targeting DPCs (250 µg polymer, 62.5 µg siRNA) resulted in target gene knockdown of 21-32%.

TABLE 4

Aha1 knockdown in HepG2 liver tumor model by peptide cleavable masking agent modified Aha1 siRNA DPCs targeted using bispecific antibodies.

| | Dig-FCit + $PEG_{12}$-FCit masking agent | | |
|---|---|---|---|
| | control siRNA | GPC-Dig bsAb Aha1 siRNA | CD33-Dig bsAb |
| human Aha1 levels (tumor) | 100 ± 10.1 | 78.6 ± 11.5 | 72.7 ± 2.4 | 68.1 ± 6.4 |
| mouse Aha1 levels (hepatocytes) | 100 ± 9.5 | 65.1 ± 8.1 | 73.7 ± 10.5 | 91.3 ± 8.3 |

Example 15

Knockdown of Targeting Gene Expression with Bispecific Antibody (bsAb)-Targeted DPCs DPCs were prepared as above except a) $PEG_{24}$-FCit was used instead of $PEG_{12}$-FCit and b) Dig-$PEG_{12}$-NHS was used to attach Dig to the polymer. $PEG_{24}$-FCit DPCs aggregated less than $PEG_{12}$-FCit DPCs and were smaller and more homogenous. In addition to being a non-labile linkage, Dig-$PEG_{12}$-NHS also contained a longer PEG. DPCs were complexes with bsAb and injected into animals as described above. Serum and tissue harvest was performed either at 24 or 48 hours post-injection. As shown in Table 5, a single dose of DPCs (250 µg polymer wt.) resulted in human Aha1 knockdown of 46-56% 24 hours post injection.

TABLE 5

Aha1 knockdown in HepG2 liver tumor model by Aha1 siRNA DPCs modified using peptide cleavable masking agents with increased PEG length.

| | Dig-$PEG_{12}$-NHS + $PEG_{24}$-FCit masking agent | |
|---|---|---|
| | GPC-Dig bsAb | CD33-Dig bsAb |
| | control siRNA | Aha1 siRNA | |
| human Aha1 levels (tumor) | 100 ± 3.1 | 54.1 ± 15.1 | 43.5 ± 6.6 |

Example 16

Targeting DPCs to Human Colorectal Adenocarcinoma Metastatic Liver Tumor Tissue by bsAb Targeted DPCs Ant-129-1 polymer was modified with 5× molar excess Dig-$PEG_{12}$-NHS and 8× weight excess $PEG_{24}$-FCit. Aha1 siRNA or GFP siRNA was attached to the modified polymer at a 4:1 polymer:siRNA weight ratio. DPCs were purified on a Sephadex G50 spin column to remove unbound reagents. Dig-DPCs were complexed with equimolar amount of IGF1R-Dig bsAb or CD33-Dig bsAb or no bsAb in sterile PBS at least 30 minutes prior to injections Animals containing HT29 tumor cells (human colorectal adenocarcinoma; ATCC Number HTB-38) were injected with the DPCs. HT29 cells overexpress the insulin-like growth factor-1 receptor protein (IGF1R), and can bind and internalize an IGF1R-Dig bispecific antibody. Animals (n=3) received DPCs (320 µg polymer). Injections were repeated after 24 hours. Serum and tissue samples were collected 48 hours after the second dose. Knockdown of human Aha1 in tumor cells was 26-38% (Table 6). Compared to CDM-DPCs, FCit-DPCs showed less off target liver Aha1 knockdown (78-83% compared to 24-36%). FCit-DPCs also showed diminished liver accumulation compared to CDM-DPCs.

TABLE 6

Aha1 knockdown in HT29 colorectal adenocarcinoma metastatic liver tumor by dipeptide cleavable Aha1 siRNA DPC.

| | Ant-129-1 polymer Dig-$PEG_{12}$-NHS + $PEG_{24}$-FCit masking agent | | |
|---|---|---|---|
| | IGF1R-Dig bsAb | | |
| | control siRNA | Aha1 siRNA | CD33-Dig bsAb |
| human Aha1 levels (tumor) | 100 ± 4.9 | 72.3 ± 6.1 | 73.7 ± 3.2 | 62.0 ± 9.0 |
| mouse Aha1 levels (liver) | 100.0 ± 11 | 64.0 ± 5.0 | 75.7 ± 11 | 66.6 ± 5.8 |

Example 17

Polymer Ant 41658-111 was modified as indicated with either disubstituted maleic anhydride (CDM) masking agents or a combination of disubstituted maleic anhydride masking agents and Phenylalanine-Citrulline(FC) dipeptide masking agents. 150 µg modified polymer in 200 µL was then co-injected into ICR mice with 40 μg apoB siRNA conjugated to cholesterol (cholesterol-siRNA), also in 200 μL. As a positive control, disubstituted maleic anhydride modified polymer (150 μg polymer) conjugated 40 μg siRNA was used. 48 h after injection, ApoB was detected by ELISA.

TABLE 7

Knockdown of Apo B in mice treated with a) modified Ant 41658-111 polymer conjugated to ApoB siRNA or b) modified Ant 41658-111 polymer co-injected with cholesterol-ApoB siRNA.

| | Masking Agent (mg masking agent to mg polymer) | | | % ApoB knockdown |
|---|---|---|---|---|
| | CDM-PEG | FC-PEG | CDM-NAG | |
| polymer-siRNA conjugate | 4.7 | | 2.3 | 92 |
| polymer + cholesterol- siRNA | | 1 | 6 | 94 |
| | | 2 | 6 | 87 |
| | | 1 | 6 | 79 |
| | | 2 | 6 | 92 |
| | | 4 | 6 | 51 |

Example 18

Inhibition of Endogenous Gene Expression in In Vivo Following siRNA Delivery by Amphipathic Poly(Acrylate) Random Copolymers-siRNA Conjugates The poly(acrylate) polymers indicated in Tables 8-11 below were masked and conjugated to siRNAs as described above. The conjugates were then injected into rats and the effect on target gene expression was determined.

TABLE 8

The indicated polymer was modified with CDM-PEG and CDM-NAG. The reversibly masked polymer was then conjugated to 60 μg Factor VII siRNA and injected in 1.0 mL injection volume into Wistar Han rats. 48 h after injection, Factor VII knockdown was measured.

| | μg | CDM modification (mg masking agent to mg polymer) | | percent Factor VII |
|---|---|---|---|---|
| polymer | polymer | NAG | PEG | knockdown |
| LAU 41648-106 | 300 | 2.3 | 4.7 | 84 |
| | 3300 | 2.3 | 4.7 | 99 |
| NAR 41439-141B-fr1 | 300 | 2.3 | 4.7 | 81 |
| | 2400 | 2.3 | 4.7 | 97 |

TABLE 9

The indicated μg of CDM modified NAR 42020-117A-fr1 polymer was conjugated to 50 μg Factor VII siRNA and injected in 1.0 mL injection volume into Wistar Han rats. 48 h after injection, Factor VII knockdown was measured.

| μg polymer | CDM modification (mg masking agent to mg polymer) | | percent Factor VII knockdown |
|---|---|---|---|
| | NAG | PEG | |
| 300 | 2.3 | 4.7 | 90 |
| 2000 | 2.3 | 4.7 | 100 |

TABLE 10

The indicated polymer was modified with CDM-PEG and CDM-NAG. The reversibly masked polymer was then conjugated to 50 μg Factor VII siRNA and injected in 1.0 mL injection volume into Wistar Han rats. 48 h after injection, Factor VII knockdown was measured.

| | μg | CDM modification (mg masking agent to mg polymer) | | percent Factor VII |
|---|---|---|---|---|
| polymer | polymer | NAG | PEG | knockdown |
| Lau 41648-140-B-fr1 | 250 | 2.3 | 4.7 | 93 |
| | 1250 | 2.3 | 4.7 | 98 |
| | 2500 | 2.3 | 4.7 | 99 |
| Lau 42101-23-D-fr1 | 250 | 2.3 | 4.7 | 95 |
| | 2000 | 2.3 | 4.7 | 99.8 |
| Lau 24 | 250 | 2.3 | 4.7 | 87 |
| | 2000 | 2.3 | 4.7 | 99 |
| Lau 41305-38-17-19 | 250 | 2.3 | 4.7 | 88 |
| | 2000 | 2.3 | 4.7 | 97 |

TABLE 11

The indicated μg of CDM modified NAR 41439-71B-fr1 (NAR 41439-117AB-fr1) polymer was conjugated to Factor VII siRNA and injected in 1.0 mL injection volume into Wistar Han rats. 48 h after injection, Factor VII knockdown was measured.

| μg polymer | μg siRNA | CDM modification (mg masking agent to mg polymer) | | percent Factor VII knockdown |
|---|---|---|---|---|
| | | NAG | PEG | |
| 300 | 60 | 2.3 | 4.7 | 87 |
| 200 | 50 | 2.3 | 4.7 | 70 |
| 2000 | 50 | 2.3 | 4.7 | 100 |

Example 19

Inhibition of Endogenous Gene Expression in In Vivo Following Co-Administration of Cholesterol-siRNA and Masked Amphipathic Poly(Acrylate) Random Copolymers The poly(acrylate) polymers indicated in Tables 12-13 below were masked as described above.

The masked polymers were then co-injected with cholesterol-siRNA into mice and the effect on target gene expression was determined.

TABLE 12

The indicated polymer was modified with CDM-PEG and CDM-NAG. The reversibly masked polymer was then co-injected with 20 μg cholestol-ApoB siRNA in 0.2 mL injection volume into C57BL/6 or ICR mice. 48 h after injection, ApoB knockdown was measured.

| | μg | CDM modification (mg masking agent to mg polymer) | | percent ApoB |
|---|---|---|---|---|
| polymer | polymer | NAG | PEG | knockdown |
| Lau 41305-38 13-15 | 300 | 2.3 | 4.7 | 49 |
| Lau 41305-38 15-17 | 300 | 2.3 | 4.7 | 82 |
| Lau 41305-38 17-19 | 300 | 2.3 | 4.7 | 91 |
| Lau 41305-38 19-21 | 300 | 2.3 | 4.7 | 83 |

TABLE 13

The indicated polymer was modified with CDM-PEG and CDM-NAG. The reversibly masked polymer was then co-injected with 40 μg cholestol-ApoB siRNA in 0.2 mL injection volume into C57BL/6 or ICR mice. 48-72 h after injection, ApoB knockdown was measured.

| polymer | μg polymer | CDM modification (mg masking agent to mg polymer) | | percent ApoB knockdown |
|---|---|---|---|---|
| | | NAG | PEG | |
| Lau 41648-140-B-fr1 | 300 | 2.3 | 4.7 | 89 |
| | 300 | 2.3 | 4.7 | 93 |
| | 150 | 2.3 | 4.7 | 59 |
| Lau 41648-140-B-fr2 | 300 | 2.3 | 4.7 | 83 |
| Lau 42101-23-D-fr1 | 150 | 2.3 | 4.7 | 95 |
| Lau 24 | 150 | 2.3 | 4.7 | 57 |
| Lau 41648-106 | 300 | 2.3 | 4.7 | 95 |
| Lau-41648-102 | 300 | 2.3 | 4.7 | 90 |
| Lau 42101-43A-1 | 150 | 2.3 | 4.7 | 41 |
| Lau 42101-43B-1 | 150 | 2.3 | 4.7 | 58 |
| Lau 42101-43C-1 | 150 | 2.3 | 4.7 | 78 |
| Lau 42101-43D-1 | 150 | 2.3 | 4.7 | 85 |
| Lau 42101-44A-1 | 150 | 2.3 | 4.7 | 95 |
| Lau 42101-44B-1 | 150 | 2.3 | 4.7 | 87 |
| Lau 42101-44C-1 | 150 | 2.3 | 4.7 | 90 |
| Lau 42101-44D-1 | 150 | 2.3 | 4.7 | 95 |
| NAR 41439-141B-fr1 | 300 | 2.3 | 4.7 | 95 |
| NAR 41439-71B-fr1 (NAR 41439-117AB-fr1) | 300 | 2.3 | 4.7 | 95 |
| Ant 41658-111 | 150 | 2.3 | 4.7 | 89 |
| | 100 | 2.3 | 4.7 | 64 |
| | 150 | 2.3 | 4.7 | 61 |
| | 200 | 2.3 | 4.7 | 92 |
| | 250 | 2.3 | 4.7 | 95 |
| | 300 | 2.3 | 4.7 | 97 |

Example 20

Amphipathic Poly(Acrylate) Random Copolymers

Various amphipathic poly(acrylate) random copolymers were synthesized as described above having the compositions listed in FIG. 14. The poly(acrylate) polymers listed in FIG. 15 were masked and conjugated to siRNAs as described above. The conjugates were then injected into the indicated animals and the effect on target gene expression was determined (FIG. 15). The poly(acrylate) polymers listed in FIG. 16 were masked as described above. The masked polymers were then co-injected with cholesterol-siRNA into animals and the effect on target gene expression was determined (FIG. 16).

The invention claimed is:

1. A membrane active poly(acrylate) random copolymer having the structure represented by:

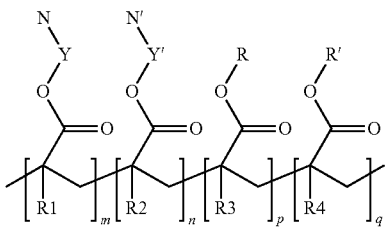

wherein:
N is —NH$_2$ or —N—CO—O—C—(CH$_3$)$_3$,
Y is —(CH$_2$)$_a$— or —(CH$_2$—CH$_2$—O)$_b$—(CH$_2$)$_c$— wherein a, b, and c are independently 1, 2, 3, 4, 5, or 6,
N' is —NR$^5$H, —NR$^5$R$^6$, —NR$^5$R$^6$R$^7$, nitrogen heterocycle, aldimine, hydrazide, hydrazone, or imidazole, wherein R$^5$, R$^6$, and R$^7$ are independently selected from —CH$_3$ and —CH$_2$—CH$_3$,
Y' is an uncharged linker group containing 1-12 carbon atoms, one or more of which may be substituted for heteroatoms,
R is a hydrophobic group having 2-6 carbon atoms or an alkoxy ethyl group,
R' is a hydrophobic group having 12-20 carbon atoms,
R1, R2, R3, and R4 are independently selected from hydrogen (—H) and methyl (—CH$_3$),
m and p are independently integers greater than zero (0),
n and q are independently integers greater than or equal to zero (0),
the ratio (m+n)/(p+q) is 0.67-5.7,
the ratio (m+n+p)/(q) is greater than or equal to 19 when q is an integer greater than or equal to 1, and
the polydispersity of the poly(acrylate) random copolymer is less than 1.5.

2. The poly(acrylate) random copolymer of claim 1 wherein R1 is a hydrogen.

3. The poly(acrylate) random copolymer of claim 2 wherein Y is —(CH$_2$)$_a$— wherein a is 2, 3, or 4.

4. The poly(acrylate) random copolymer of claim 2 wherein Y is —CH$_2$—CH$_2$—O—(CH$_2$)$_2$—.

5. The poly(acrylate) random copolymer of claim 2 wherein R is selected from the group consisting of:
—(CH$_2$)$_k$—CH$_3$ wherein k is 1, 2, or 3,
—CH(CH$_3$)—CH$_2$—CH$_3$, and
—(CH$_2$)$_l$—CH$_2$—CH$_3$ wherein and l is 2, 3, or 4.

6. The poly(acrylate) random copolymer of claim 5 wherein R is —CH$_2$—CH$_2$—O—CH$_2$—CH$_3$.

7. The poly(acrylate) random copolymer of claim 2 wherein n is zero.

8. The poly(acrylate) random copolymer of claim 7 wherein q is zero.

9. The poly(acrylate) random copolymer of claim 2 wherein R3 is hydrogen.

10. The poly(acrylate) random copolymer of claim 9 wherein (m+n)/(p+q) is 1-1.86.

11. The poly(acrylate) random copolymer of claim 2 wherein R3 is methyl.

12. The poly(acrylate) random copolymer of claim 9 wherein (m+n)/(p+q) is 1.86-3.

13. The poly(acrylate) random copolymer of claim 1 wherein:
Y is —(CH$_2$—CH$_2$—O)—CH$_2$—CH$_2$—,
R is —CH$_2$—CH$_2$—CH$_3$,
R1 is hydrogen
R3 is methyl,
n and q are both zero,
and m/p is 2.2-3.

14. The poly(acrylate) random copolymer of claim 1 wherein:
Y is —(CH$_2$—CH$_2$—O)—CH$_2$—CH$_2$—,
R is —CH$_2$—CH$_2$—CH$_3$,
R1 and R3 are both hydrogen
n and q are both zero,
and m/p is 1-1.86.

15. The poly(acrylate) random copolymer of claim 1 wherein:
Y is —(CH$_2$—CH$_2$—O)—CH$_2$—CH$_2$—,
R is —CH$_2$—CH$_2$—CH$_2$—CH$_3$,
R1 and R3 are both hydrogen
n and q are both zero,
and m/p is 1-1.86.

16. The poly(acrylate) random copolymer of claim 1 wherein the polymer is conjugated to an RNA interference polynucleotide.

17. The poly(acrylate) random copolymer of claim 1 wherein greater than 50% of N are reversibly modified by reaction with disubstituted maleic anhydride masking agents, dipeptide-amidobenzyl-carbonate masking agents, or a combination of disubstituted maleic anhydride masking agents and dipeptide-amidobenzyl-carbonate masking agents.

18. A composition for inhibiting gene expression in vivo comprising the poly(acrylate) random copolymer of claim 17 and an RNA interference polynucleotide in a pharmaceutically acceptable carrier.

19. The composition of claim 18 wherein the RNA interference polynucleotide is covalently linked to the poly(acrylate) random copolymer.

20. The composition of claim 18 wherein the RNA interference polynucleotide is conjugated to a hydrophobic group containing at least 20 carbon atoms.

* * * * *